United States Patent
Flores et al.

(10) Patent No.: US 7,842,668 B1
(45) Date of Patent: Nov. 30, 2010

(54) APO-2 LIGAND/TRAIL FORMULATIONS

(75) Inventors: Heather Flores, Hayward, CA (US);
Tanya P. Lin, Bronx, NY (US);
Timothy C. Matthews, San Francisco, CA (US); Roger Pai, Los Altos, CA (US); Zahra Shahrokh, Weston, MA (US)

(73) Assignee: Genentech, Inc., South San Francisco, CA (US)

( * ) Notice: Subject to any disclaimer, the term of this patent is extended or adjusted under 35 U.S.C. 154(b) by 763 days.

(21) Appl. No.: 11/541,344

(22) Filed: Sep. 29, 2006

Related U.S. Application Data

(63) Continuation-in-part of application No. 10/771,254, filed on Feb. 3, 2004, now abandoned, which is a continuation-in-part of application No. PCT/US02/36251, filed on Nov. 12, 2002.

(60) Provisional application No. 60/338,249, filed on Nov. 13, 2001.

(51) Int. Cl.
*A61K 38/00* (2006.01)

(52) U.S. Cl. .............................. 514/12; 514/2
(58) Field of Classification Search ................ None
See application file for complete search history.

(56) References Cited

U.S. PATENT DOCUMENTS

| | | | |
|---|---|---|---|
| 5,763,223 | A | 6/1998 | Wiley et al. |
| 6,030,945 | A | 2/2000 | Ashkenazi |
| 6,284,236 | B1 | 9/2001 | Wiley et al. |
| 6,541,606 | B2 | 4/2003 | Margolin et al. |

FOREIGN PATENT DOCUMENTS

| | | |
|---|---|---|
| EP | 0 417 563 | 3/1991 |
| EP | 0 870 827 B1 | 3/2004 |
| JP | S62-283932 | 12/1987 |
| JP | H10-182481 | 7/1998 |
| WO | WO 97/01633 | 1/1997 |
| WO | WO 97/25428 | 7/1997 |
| WO | WO 98/28426 | 2/1998 |
| WO | WO 98/18921 | 5/1998 |
| WO | WO 98/32856 | 7/1998 |
| WO | WO 98/35986 | 8/1998 |
| WO | WO 98/41629 | 9/1998 |
| WO | WO 98/46643 | 10/1998 |
| WO | WO 98/46751 | 10/1998 |
| WO | 98/51793 | 11/1998 |
| WO | WO 99/02653 | 1/1999 |
| WO | WO 99/09165 | 2/1999 |

(Continued)

OTHER PUBLICATIONS

Gueffroy, Ed. Buffers: A guide for the preparation and use of buffers in biological systems. Behring Diagnostics. Hoechst Corporation. 1975, pp. 10-11.*

(Continued)

*Primary Examiner*—Cherie M Woodward
(74) *Attorney, Agent, or Firm*—Diane L. Marschang

(57) ABSTRACT

The inventions include Apo2L/TRAIL formulations and methods of using such formulations. Lyophilized and crystal formulations of Apo-2L/TRAIL which are stable and have improved Apo2L/TRAIL trimer formation are provided. Methods of making Apo-2L/TRAIL formulations, as well as devices and kits containing such formulations are also provided.

14 Claims, 23 Drawing Sheets

FOREIGN PATENT DOCUMENTS

| WO | 99/06673 | 3/1999 |
| --- | --- | --- |
| WO | WO 99/11791 | 3/1999 |
| WO | 99/01039 | 7/1999 |
| WO | WO 00/75191 A2 | 12/2000 |
| WO | 00/17579 | 1/2001 |
| WO | WO 01/00832 | 1/2001 |
| WO | WO 0124814 A1 * | 4/2001 |
| WO | WO 01/24814 | 12/2001 |
| WO | WO 02/09755 A2 | 2/2002 |

OTHER PUBLICATIONS

Hymowitz et al., (Biochemistry, Jan. 4, 2000; 39:633-640; cited in Applicant's IDS of May 27, 2007).*

Armitage et al., "Molecular and Biological Characterization of a Murine Ligand for CD40" *Nature* 357(6373):80-82 (1992).

Ashkenazi et al., "Safety and antitumor activity of recombinant soluble Apo2 ligand" *Journal of Clinical Investigation* 104(2):155-162 (1999).

Banner et al., "Crystal Structure of the Soluble Human 55 kd TNF Receptor-Human TNFβ Complex: Implications for TNF Receptor Activation" *Cell* 73:431-445 (1993).

Bodmer et al., "Cysteine 230 Is Essential for the Structure and Activity of the Cytotoxic Ligand TRAIL" *Journal of Biological Chemistry* 275:20632-20637 (2000).

Brockhaus et al., "Identification of Two Types of Tumor Necrosis Factor Receptors on Human Cell Lines by Monoclonal Antibodies." *Proc. Natl. Acad. Sci. USA* 87:3127-3131 (1990).

Browning et al., "Lymphotoxin β, a Novel Member of the TNF Family That Forms a Heteromeric Complex with Lymphotoxin on the Cell Surface" *Cell* 72:847-856 (1993).

Cha et al., "2.8 A Resolution Crystal Structure of Human TRAIL, a Cytokine with Selective Antitumor Activity" *Immunity* 11:253-261 (1999).

Chicheportiche et al., "TWEAK, A New Secreted Ligand in the Tumor Necrosis Factor Family that Weakly Induces Apoptosis" *Journal of Biological Chemistry* 272(51):32401-32410 (1997).

Chinnaiyan et al., "Combined effect of tumor necrosis factor-related apoptosis-inducing ligand and ionizing radiation in breast cancer therapy" *Proc. Natl. Acad. Sci.* 97:1754-1759 (2000).

Craft et al. *Clin Chem* (Abstract only) 34(1):44-8 (Jan. 1988).

Darby and Creighton, "Disulfide Bonds in Protein Folding and Stability" *Methods in Enzymology*, B.A. Shirley, Totowa, NJ:Human Press Inc, Chapter 10, vol. 40:219-252 (1995).

Dealtry et al., "DNA Fragmentation and Cytotoxicity Caused by Tumor Necrosis Factor is Enhanced by Interferon-γ" *European Journal of Immunology* 17:689-693 (1987).

Degli-Esposti et al., "Cloning and Characterization of TRAIL-R3, a Novel Member of the Emerging TRAIL Receptor Family" *Journal of Experimental Medicine* 186(7):1165-1170 (1997).

Degli-Esposti et al., "The Novel Receptor TRAIL-R4 Induces NF-κB and Protects against TRAIL-Mediated Apoptosis, yet Retains an Incomplete Death Domain" *Immunity* 7:813-820 (1997).

Gazitt, Y., "TRAIL is a potent inducer of apoptosis in myeloma cells derived from multiple myeloma patients and is not cytotoxic to hematopoietic stem cells" *Leukemia* 13:1817-1824 (1999).

Gliniak and Le, "Tumor Necrosis Factor-related Apoptosis-inducing Ligand's Antitumor Activity in Vivo Is Enhanced by the Chemoptherapeutic Agent CPT-11" *Cancer Research* 59:6153-6158 (1999).

Goodwin et al., "Molecular Cloning and Expression of the Type 1 and Type 2 Murine Receptors for Tumor Necrosis Factor." *Mol. Cell. Bio.* 11:3020-3026 (1991).

Griffith et al., "Monocyte-mediated Tumoricidial Activity via the Tumor Necrosis Factor-related Cytokine, TRAIL" *Journal of Experimental Medicine* 189:1343-1353 (1999).

Gruss and Dower, "Tumor Necrosis Factor Ligand Superfamily: Involvement in the Pathology of Malignant Lymphomas" *Blood* 85:3378-3404 (1995).

Hahne et al., "APRIL, A New Ligand of the Tumor Necrosis Factor Family, Stimulates Tumor Cell Growth" *J Exp Med.* 188(6):1185-1190 (Sep. 21, 1998).

Hale et al., "Demonstration of in Vitro and in Vivo Efficacy of Two Biologically Active Human Soluble TNF Receptors Expressed in *E. coli*." *J. Cell. Biochem.* (abstract only, suppl. 15F; P 424) p. 113 (1991).

Hohmann et al., "Two Different Cell Types Have Different Major Receptors for Human Tumor Necrosis Facotr (TNFα)" *Journal of Biological Chemistry* 264:14927-14934 (1989).

Hymowitz et al., "A unique zinc-binding site revealed by the high-resolution X-ray structure of homotrimeric Apo2L/TRAIL" *Biochemistry* 39(4):633-640 (2000).

Hymowitz et al., "Triggering Cell Death: The Crystal Structure of Apo2L/TRAIL in a Complex with Death Receptor 5" *Molecular Cell* 4(4):563-571 (1999).

*Information Hyperlinked Over Proteins (IHOP)*, TNFSF10.

Itoh et al., "The Polypeptide Encoded by the cDNA for Human Cell Surface Antigen Fas Can Mediate Apoptosis." *Cell.* 66:233-243 (1991).

Jeremias et al., "TRAIL/Apo-2-ligand-induced apoptosis in human T cells" *European Journal of Immunology* 28:143-152 (1998).

Jo et al., "Apoptosis induced in normal human hepatocytes by tumor necrosis factor-related apoptosis-inducing ligand" *Nature Medicine* 6(5):564-567 (2000).

Johnsen et al., "Regulation of Apo-2 Ligand/TRAIL Expression in NK cells-Involvement in NK Cell-Mediated Cytotoxicity" *Cytokine* 11:664-672 (1999).

Johnson et al., "Expression and Structure of the Human NGF Receptor" *Cell* 47:545-554 (1986).

Katsikis et al., "Interleukin-1β Converting Enzyme-like Protease Involvement in Fas-induced and Ativation-induced Peripheral Blood T Cell Apoptosis in HIV Infection. TNF-related Apoptotsis-inducing Ligand Can Mediate ACtivation-induced T Cell Death in HIV Infection" *Journal of Experimental Medicine*.

Keane, et al., "Chemotherapy Augments TRAIL-induced Apoptosis in Breast Cell Lines" *Cancer Research* 59:734-741 (Feb. 1, 1999).

Kohno et al., "A Second Tumor Necrosis Factor Receptor Gene Product Can Shed a Naturally Occurring Tumor Necrosis Factor Inhibitor." *Proc. Natl. Acad. Sci. USA* 87:8331-8335 (1990).

Lawrence et al., "Differential hepatocyte toxicity of recombinant Apo2L/TRAIL versions" *Nature Medicine* 7(4):383-385 (Apr. 2001).

Lewis et al., "Cloning and Expression of cDNAs for Two Distinct Murine Tumor Necrosis Factor Receptors Demonstrate One Receptor is Species Specific." *PNAS USA.* 88:2830-2834 (1991).

Loetscher et al., "Molecular cloning and Expression of the Human 55 kd Tumor Necrosis Factor Receptor" *Cell* 61:351-359 (1990).

MacFarlane et al., "Identification and Molecular Cloning of Two Novel Receptors for the Cytotoxic Ligand TRAIL" *Journal of Biological Chemistry* 272(41):25417-25420 (1997).

Mallet et al., "Characterization of the MRC OX40 Antigen of Activated CD4 Positive T Lymphocytes—A Molecule Related to Nerve Growth Factor Receptor." *EMBO Journal* 9(4):1063-1068 (1990).

Mariani et al., "Interleukin 1β-converting Enzyme Related Proteases/Caspases Are Involved in TRAIL-induced Apoptosis of Myeloma and Leukemia Cells" *Journal of Cell Biology* 137:221-229 (1997).

Marsters et al., "A Novel Receptor for Apo2L/TRAIL Contains a Truncated Death Domain" *Current Biology* 7:1003-1006 (1997).

Marsters et al., "Identification of a Ligand for the Death-Domain-Containing Receptor Apo3" *Current Biology* 8(9):525-528 (1998).

Meyer et al. *Pharm Biotechnol* (Abstract only) 13:85-107 (2002).

Miura et al., "Critical Contribution of Tumor Necrosis Factor-related to Apoptosis-inducing Ligand (TRAIL) to Apoptosis of Human CD4 T Cells in HIV-1-infected hu-PBL-NOD-SCID Mice" *Journal of Experimental Medicine* 193:651-660 (2001).

Mizutani et al., "Synergistic Cytotoxicity and Apoptosis by Apo-2 Ligand and Adriamycin against Bladder Cancer Cells" *Clin. Cancer Research* 5:2605-2612 (1999).

Mongkolsapaya et al., "Cutting Edge: Lymphocyte Inhibitor of TRAIL (TNF-Related Apoptosis-Inducing Ligand): A New Receptor Protecting Lymphocytes From the Death Ligand TRAIL" *J. Immunol.* 160(1):3-6 (1998).

Moore et al., "BLyS: Member of the Tumor Necrosis Factor Family and B Lymphocyte Stimulator" *Science* 285(5425):260-263 (1999).

Mukhopadhyay et al., "Identification and Characterization of a Novel Cytokine, THANK, a TNF Homologue That Activates Apoptosis, Nuclear Factor-κB, and c-Jun $NH_2$-Terminal Kinase" *J. Bio. Chem.* 274:15978-15981 (1999).

Nagata, S., "Steering anti-cancer drugs away from the TRAIL" *Nature Medicine* 6(5):502-503 (May 2000).

Nophar et al., "Soluble Forms of Tumor Necrosis Factor Receptors (TNF-Rs). The cDNA for the Type I TNF-R, Cloned Using Amino Acid Sequence Data of its Soluble Form, Encodes Both the Cell Surface and a Soluble Form of the Receptor." *Embo Journal.* 9:3269-3278 (1990).

Page et al. *J. Pharm Pharmacol* 52(1):19-26 (Jan. 2000).

Pan et al., "An Antagonist Decoy Receptor and a Death-Domain Containing Receptor for TRAIL" *Science* 277:815-818 (Aug. 1997).

Pan et al., "The Receptor for the Cytotoxic Ligand TRAIL" *Science* 276:111-113 (Apr. 4, 1997).

Pan et al., "TRUNDD, A New Member of the TRAIL Receptor Family That Antagonizes TRAIL Signalling" *FEBS Letters* 424(1-2):41-45 (1998).

Pitti et al., "Genomic Amplification of a Decoy Receptor for Fas Ligand in Lung and Colon Cancer" *Nature* 396(6712):699-703 (Dec. 17, 1998).

Pitti et al., "Induction of Apoptosis by Apo-2 Ligand, a New Member of the Tumor Necrosis Factor Cytokine Family" *Journal of Biological Chemistry* 271:12687-12690 (1996).

Qin et al., "Avoiding premature apoptosis of normal epidermal cells" *Nature Medicine* 7(4):385-386 (Apr. 2001).

Radeke et al., "Gene Transfer and Molecular Cloning of the Rat Nerve Growth Factor Receptor." *Nature.* 325:593-597 (1987).

Rieger et al, "APO2 ligand: a novel lethal weapon against malignant glioma?" *FEBS Letters* 427:124-128 (1998).

Roth et al., "Locoregional Apo2L/TRAIL Eradicates Intracranial Human Malignant Glioma Xenografts in Athymic Mice in the Absence of Neurotoxicity" *Biochem. Biophys. Res. Comm* 265:479-483 (1999).

Schall et al., "Molecular Cloning and Expression of a Receptor for Human Tumor Necrosis Factor" *Cell* 61:361-370 (1990).

Schmid et al., "DNA Fragmentation: Manifestation of Target Cell Destruct. Mediated by Cytotoxic T-cell Lines, Lymphotoxin-Secreting Helper T-cell Clones, and Cell-Free Lymphotoxin-Containing Supernatant" *Proc. Natl. Acad. Sci. USA* 83:1881-1885 (1986).

Schneider et al., "BAFF, A Novel Ligand of the Tumor Necrosis Factor Family, Stimulates B Cell Growth" *Journal of Experimental Medicine* 189:1747-1756 (1999).

Schneider et al., "Characterization of Two Receptors for TRAIL" *FEBS Letters* 416:329-334 (1997).

Screaton et al., "TRICK2, A New Alternatively Spliced Receptor that Transduces the Cytotoxic Signal From TRAIL" *Current Biology* 7:693-696 (1997).

Sheridan et al., "Control of TRAIL-Induced Apoptosis by a Family of Signaling and Decoy Receptors" *Science* 277:818-821 (1997).

Shu et al., "TALL-1 is a Novel Member of the TNF Family that is Down-Regulated by Mitogens" *J. Leukocyte Biol.* 65:680-683 (1999).

Smith et al., "A Receptor for Tumor Necrosis Factor Defines an Unusual Family of Cellular and Viral Proteins" *Science* 248:1019-1023 (1990).

Smith et al., "T2 Open Reading Frame From the Shope Fibroma Virus Encodes a Soluble Form of the TNF Receptor." *Biochem. & Biophys. Res. Comm.* 176:335-342 (1991).

Song et al., "Tumor Necrosis Factor-related Apoptosis-inducing Ligand (TRAIL) Is an Inhibitor of Autoimmune Inflammation and Cell Cycle Progression" *Journal of Experimental Medicine* 191(7):1095-1103 (2000).

Stamenkovic et al., "A B-Lymphocyte Activation Molecule Related to the Nerve Growth Factor Receptor and Induced by Cytokines in Carcinomas." *EMBO Journal.* 8(5):1403-1410 (1989).

Thomas and Hersey, "TNF-Related Apoptosis-Inducing Ligand (TRAIL) Induces Apoptosis in Fas Ligand-Resistant Melanoma Cells and Mediates CD4 T Cell Killing of Target Cells" *J. Immunol.* 161:2195-2200 (1998).

Upton et al., "Myxoma Virus Expresses a Secreted Protein with Homology to the Tumor Necrosis Factor Receptor Gene Family that Contributes to Viral Virulence." *Virology.* 184:370-382 (1991).

Upton et al., "Tumorigenic Poxviruses: Genomic Organization and DNA Sequence of the Telomeric Region of the Shope Fibroma Virus Genome." *Virology.* 160:20-30 (1987).

Walczak et al., "TRAIL-R2: A Novel Apoptosis-Mediating Receptor for TRAIL" *EMBO Journal* 16(17):5386-5397 (1997).

Walczak et al., "Tumoricidal activity of tumor necrosis factor-related apoptosis-inducing ligand in vivo" *Nature Med.* 5:157-163 (1999).

Wiley et al., "Identification and Characterization of a New Member of the TNF Family that Induces Apoptosis" *Immunity* 3:673-682 (1995).

Wu et al., "KILLER/DR5 is a DNA Damage-Inducible p53-Regulated Death Receptor Gene" *Nature Genetics* 17:141-143 (1997).

Yu et al., "Tumor Necrosis Factor-related Apoptosis-inducing Ligand-mediated Apoptosis in Androgen-independent Prostate Cancer Cells" *Cancer Research* 60:2384-2389 (2000).

Cromwell et al., "Self-Association of Therapeutic Proteins" *Misbehaving Proteins*, Springer Science+Business Media, LLC pp. 313-330 (2006).

\* cited by examiner

FIG._1

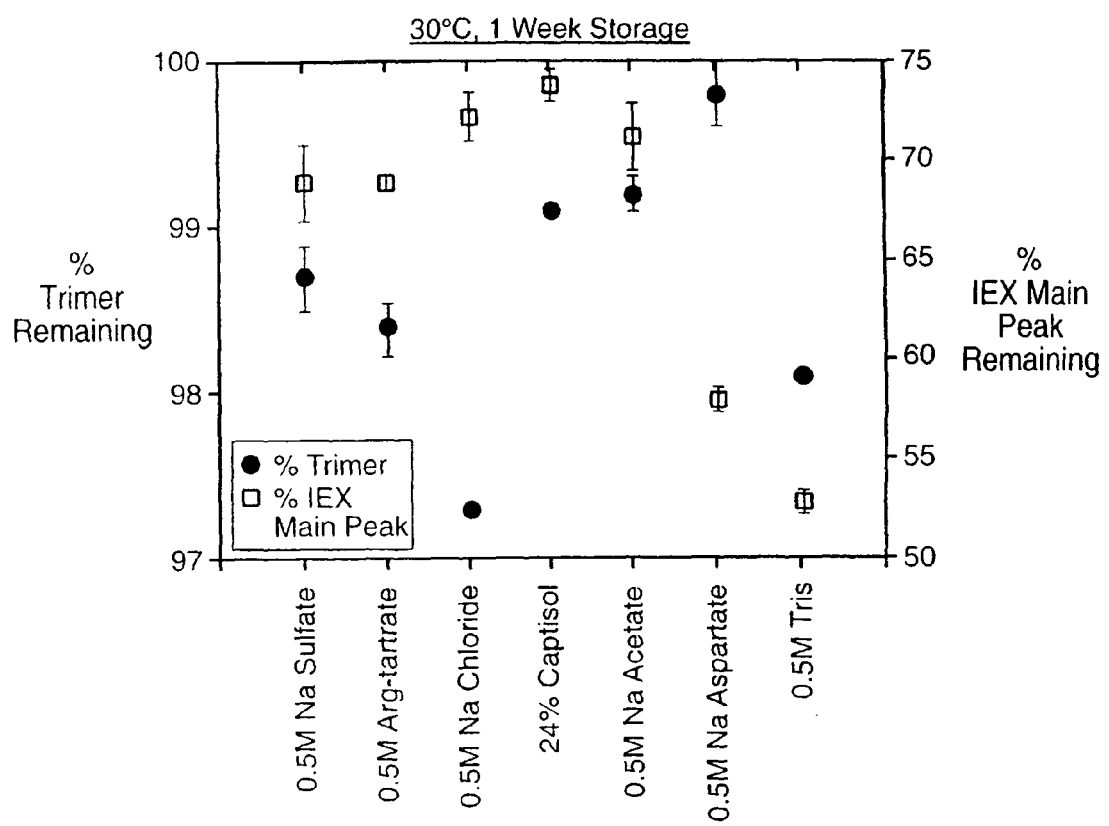
FIG._2

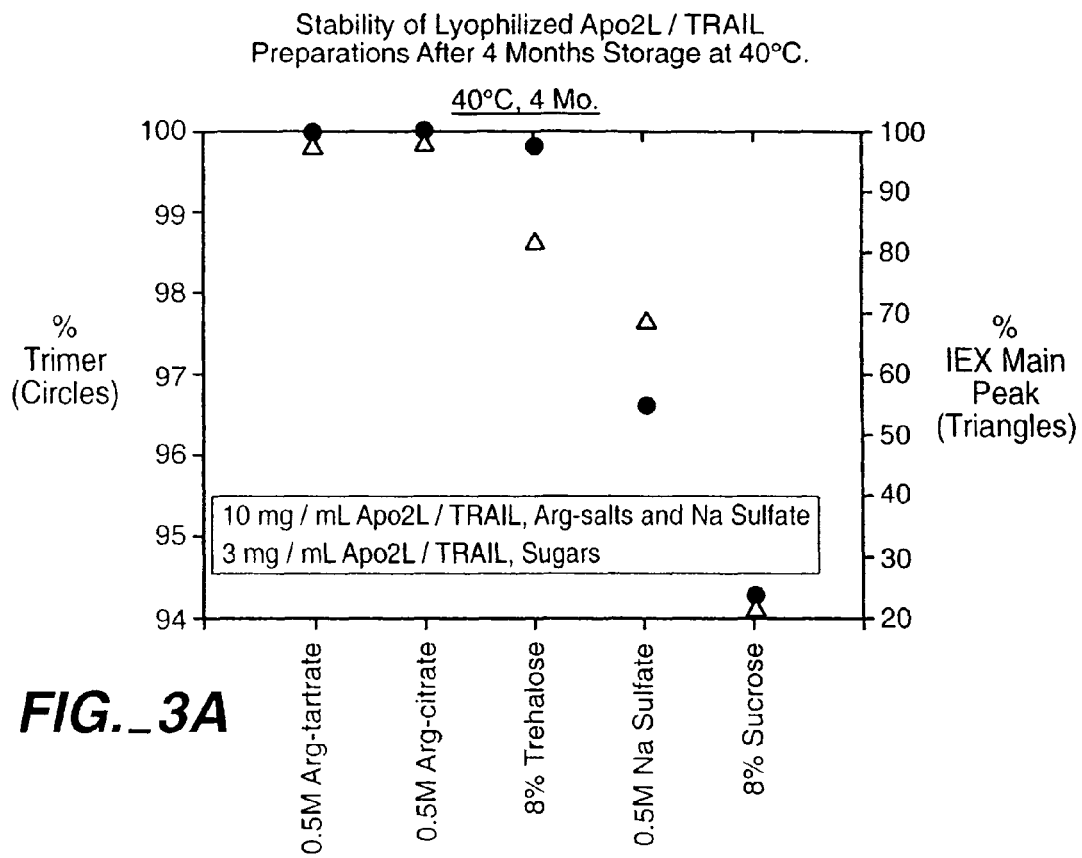
*FIG._3A*
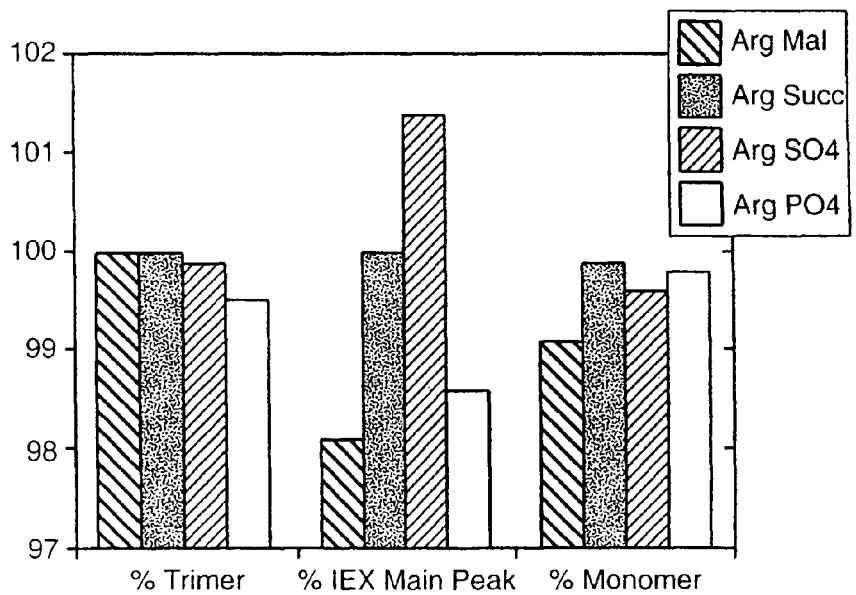
*FIG._3B*

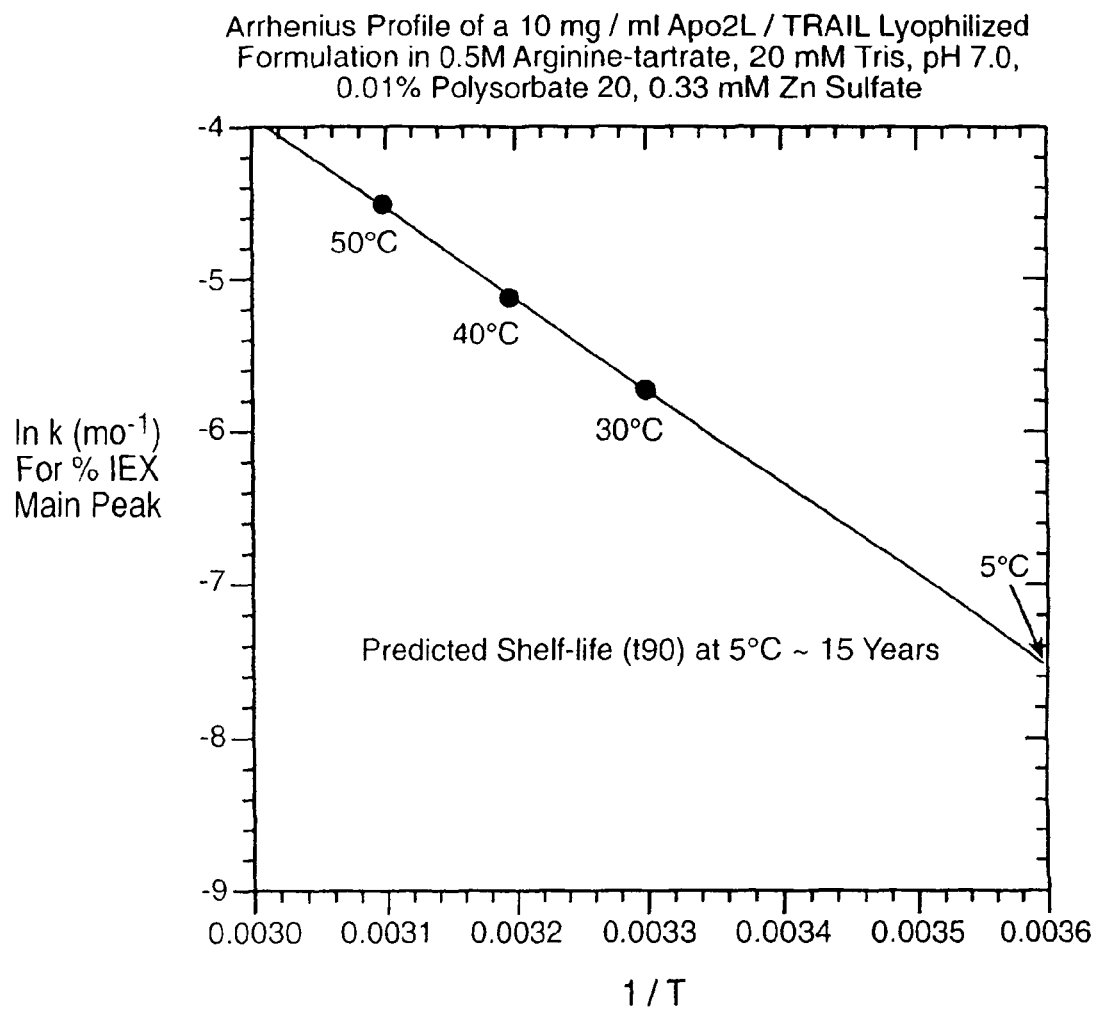
FIG._3C

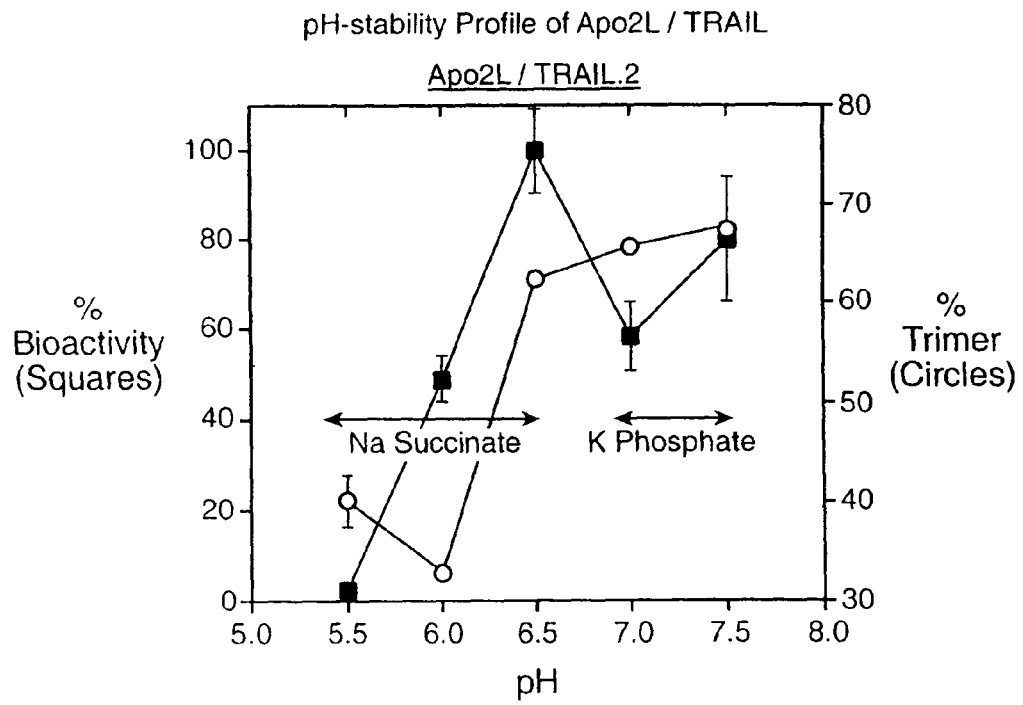
FIG._4A
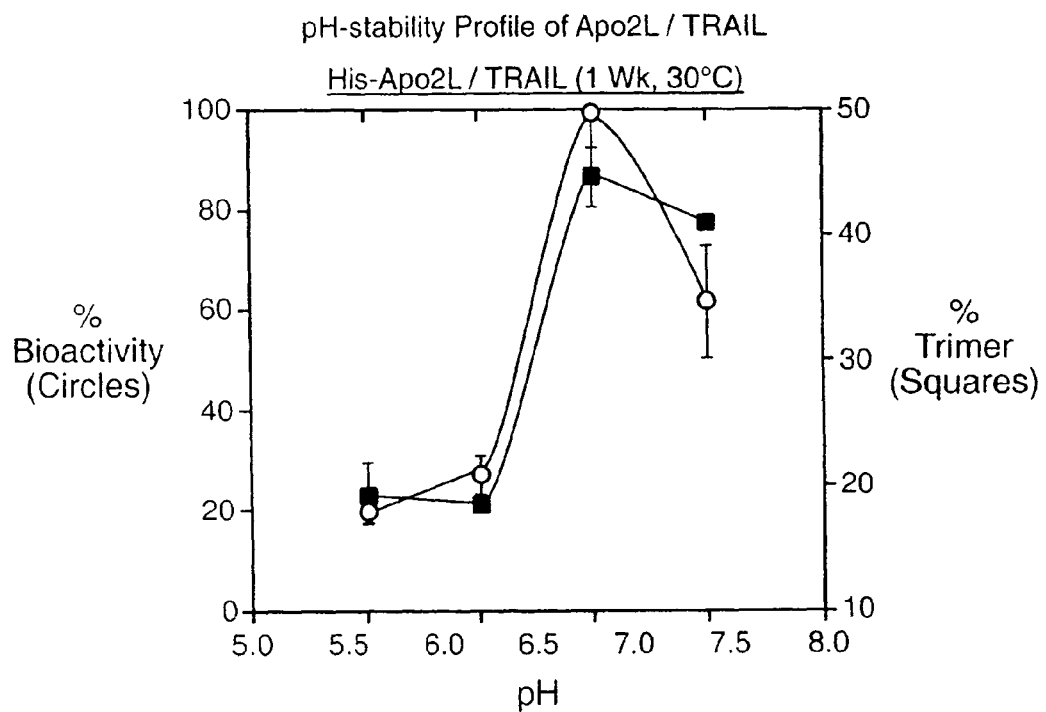
FIG._4B

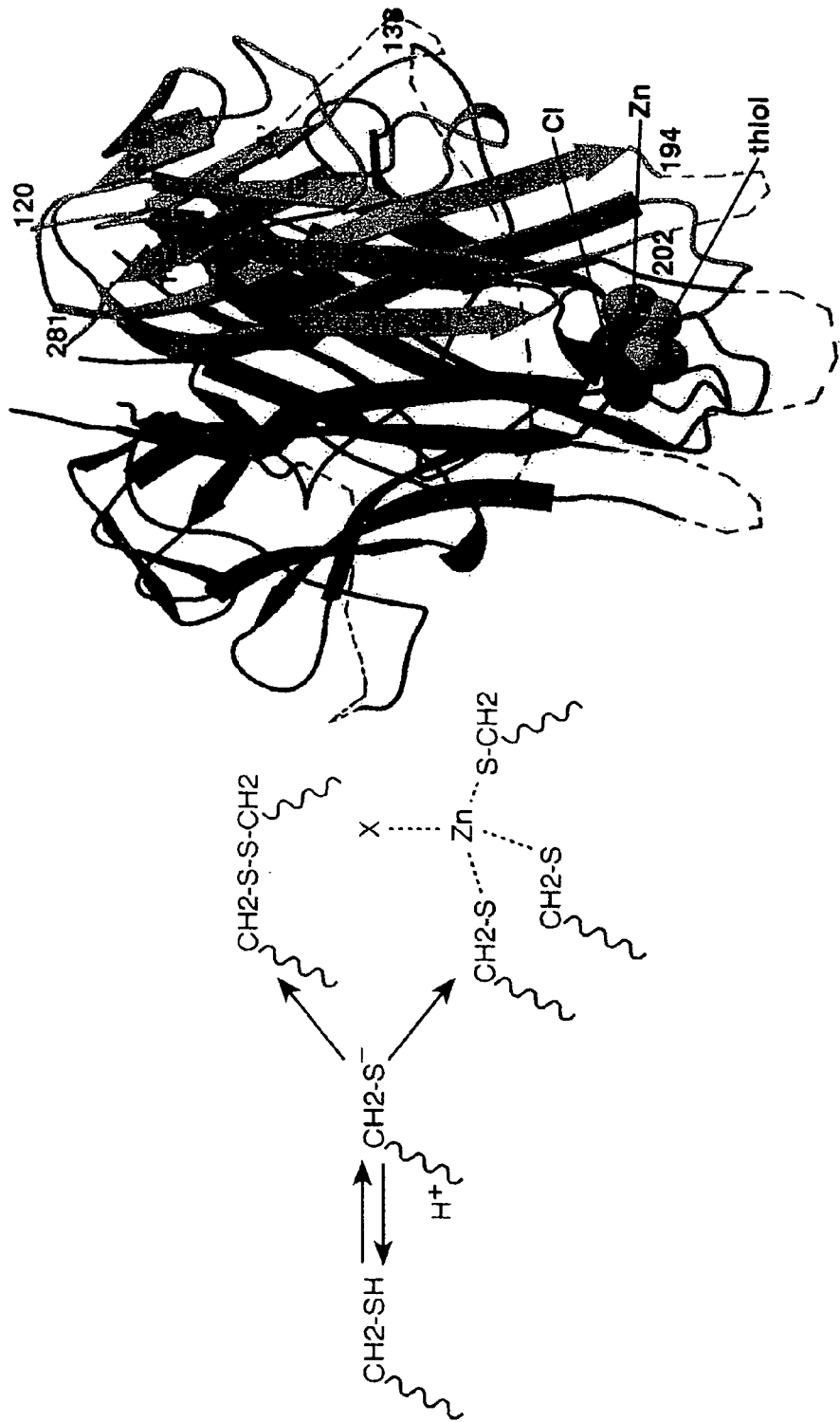
FIG._5

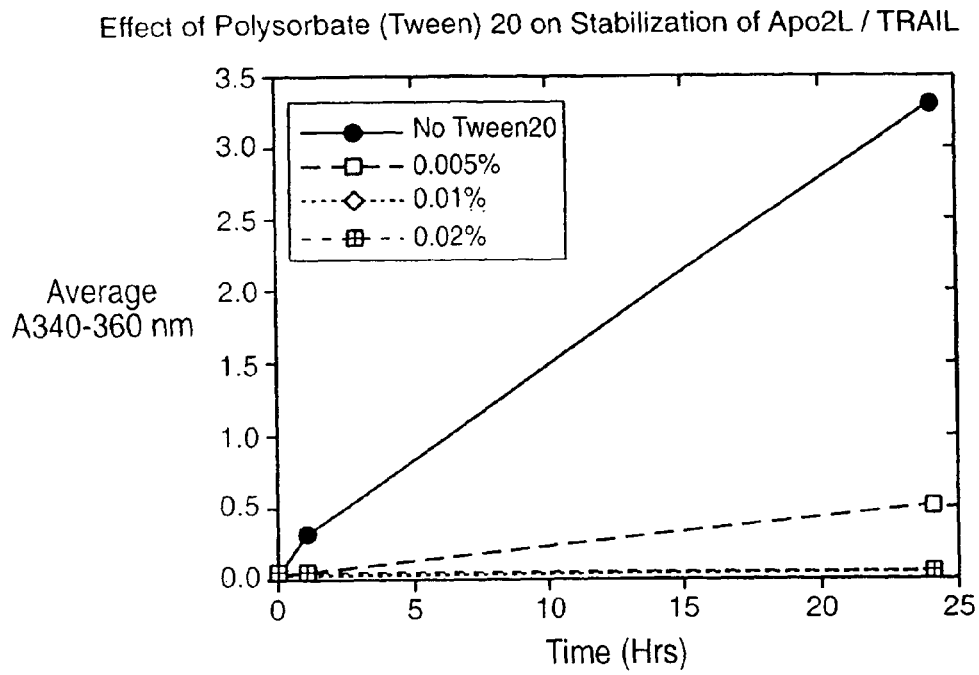
FIG._6
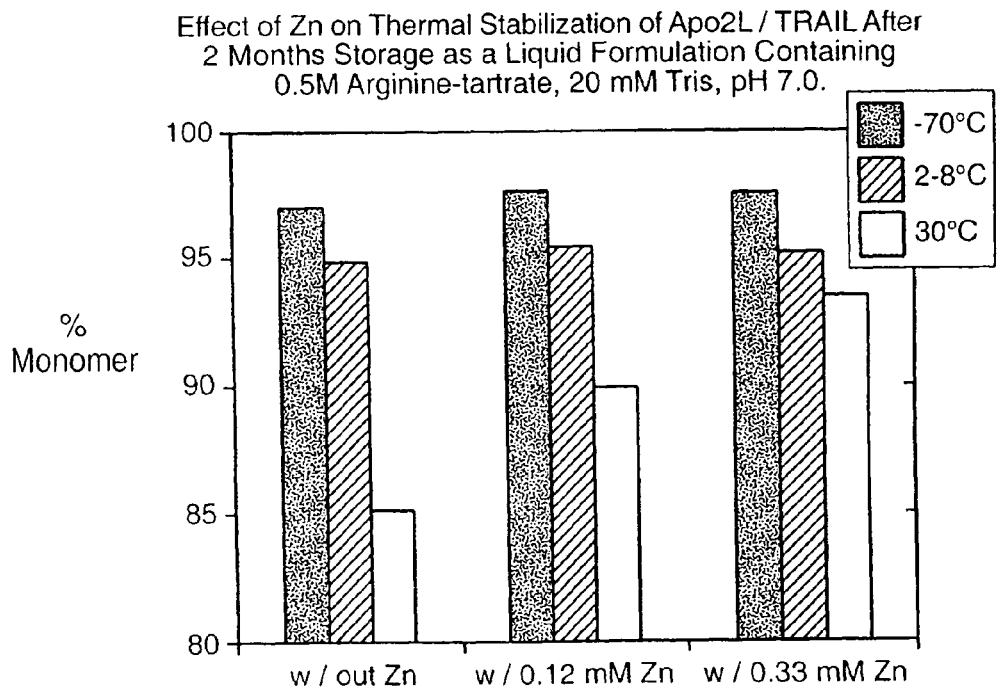
FIG._7

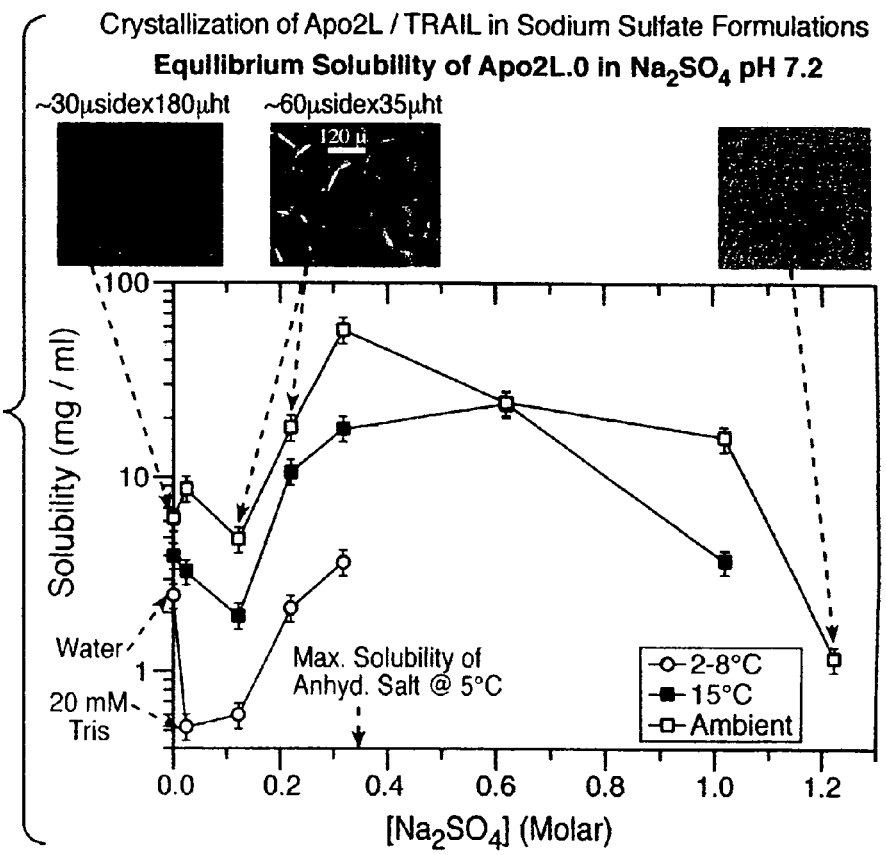
FIG._8
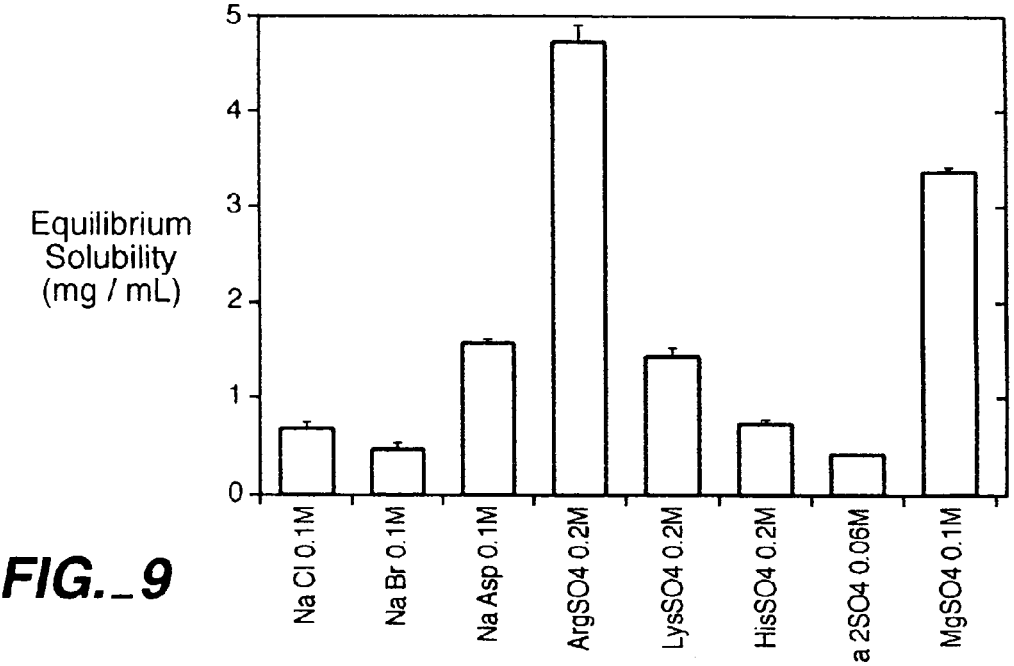
FIG._9

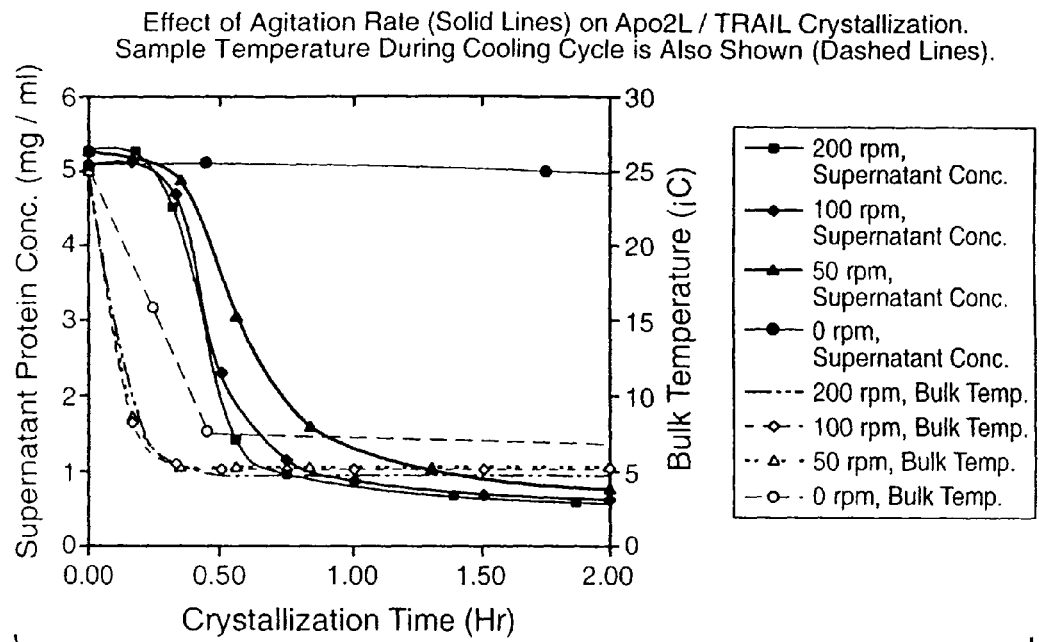
FIG._10A
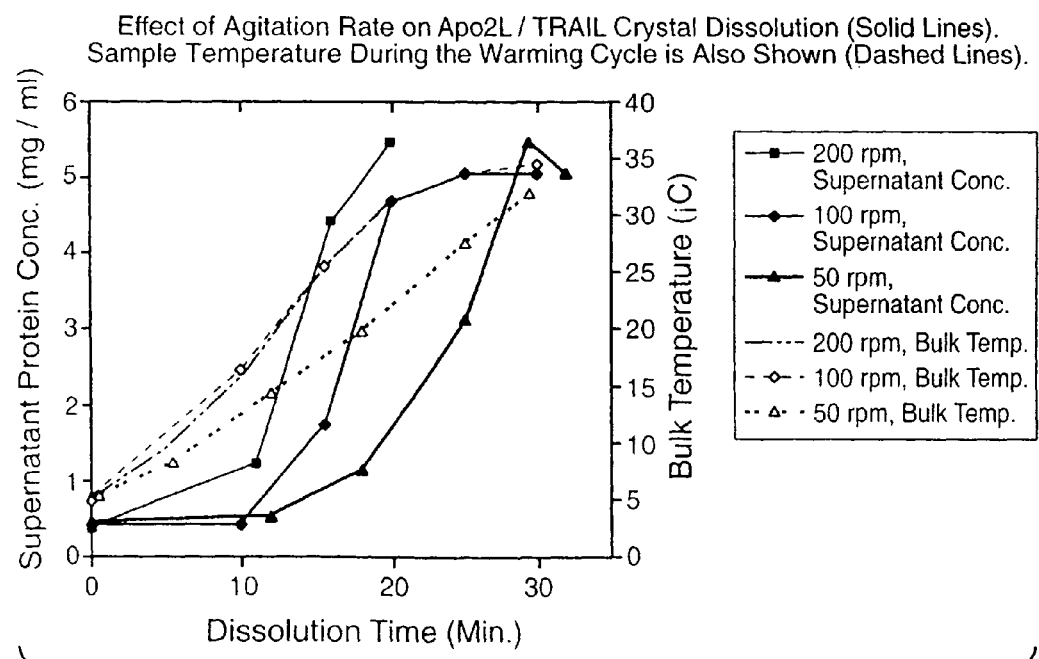
FIG._10B

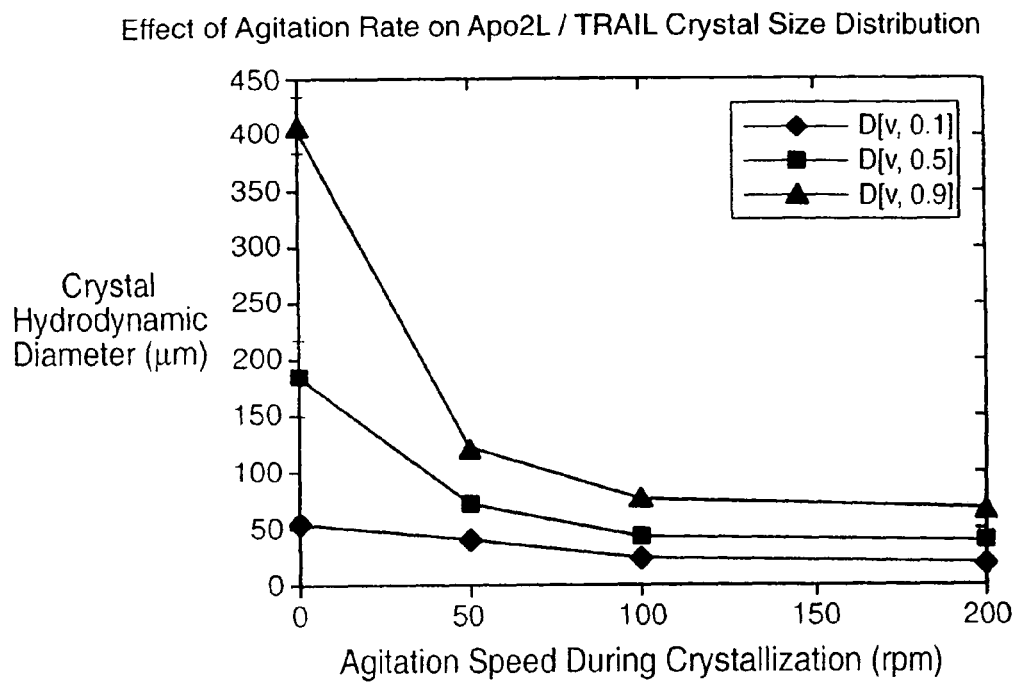
FIG._10C
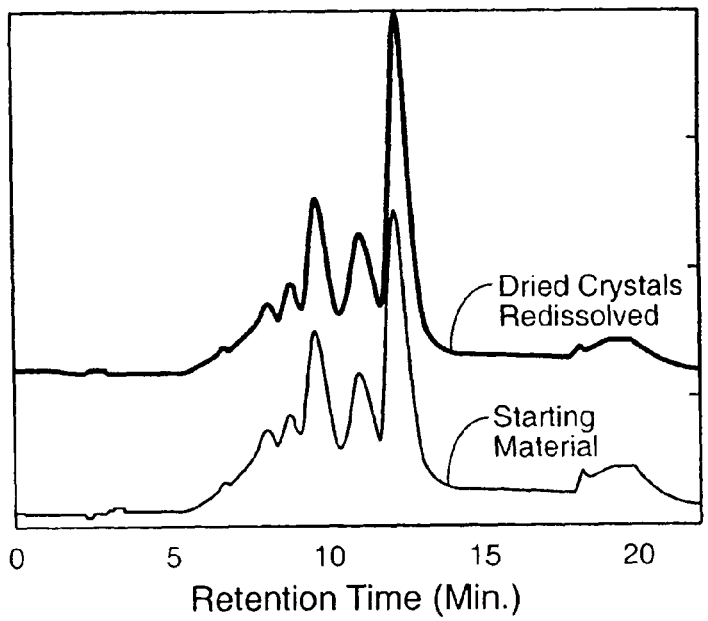
FIG._11A

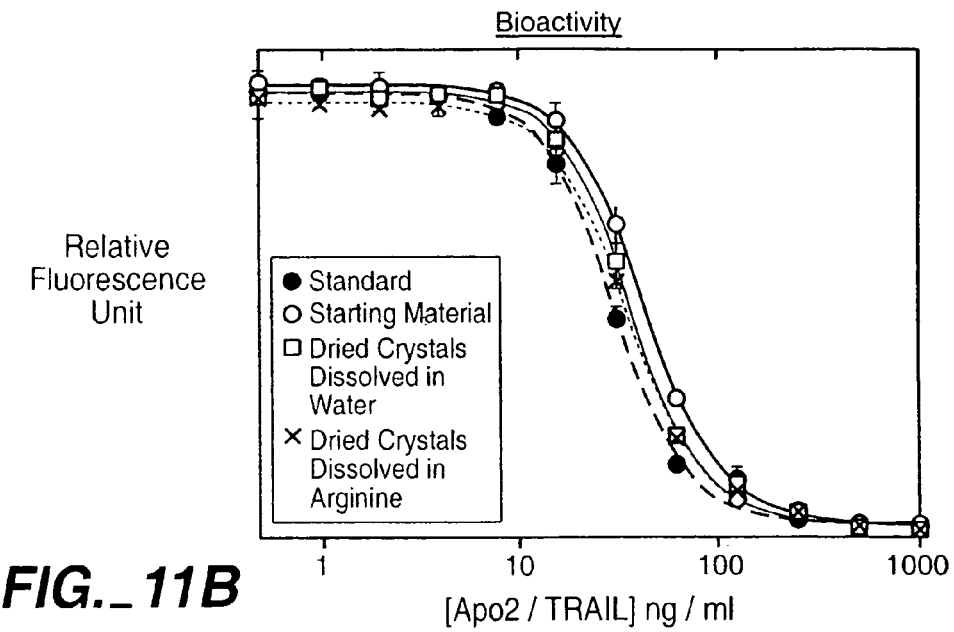
FIG._11B
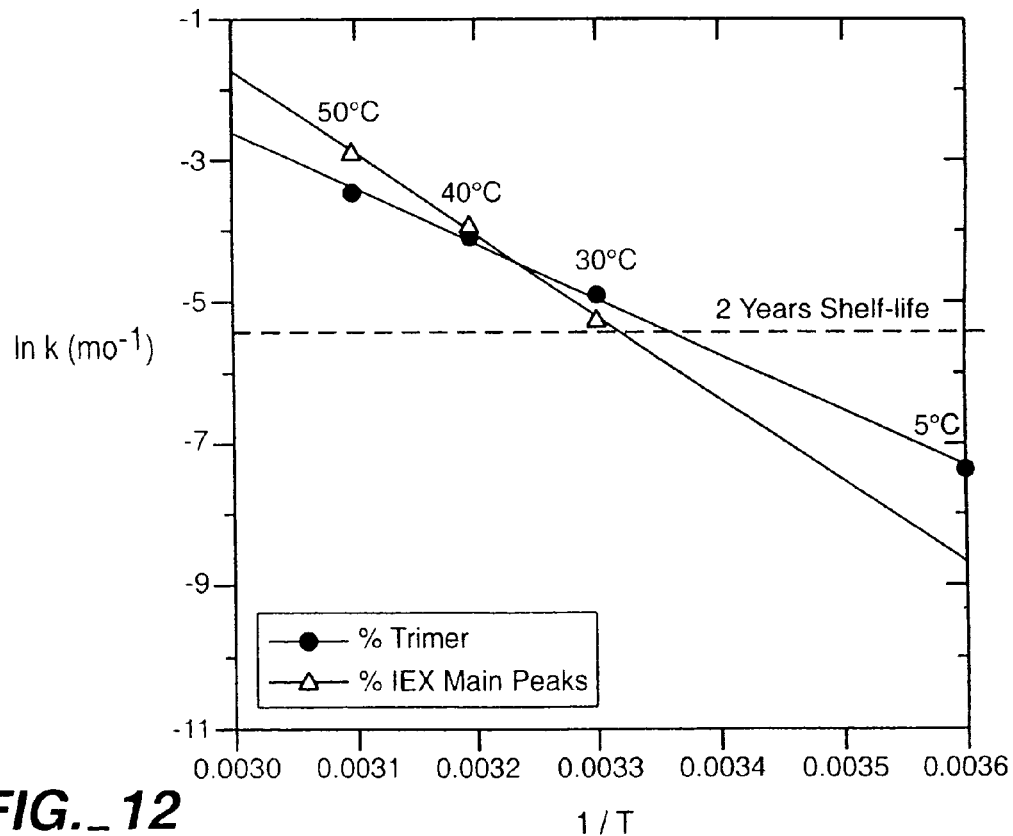
FIG._12

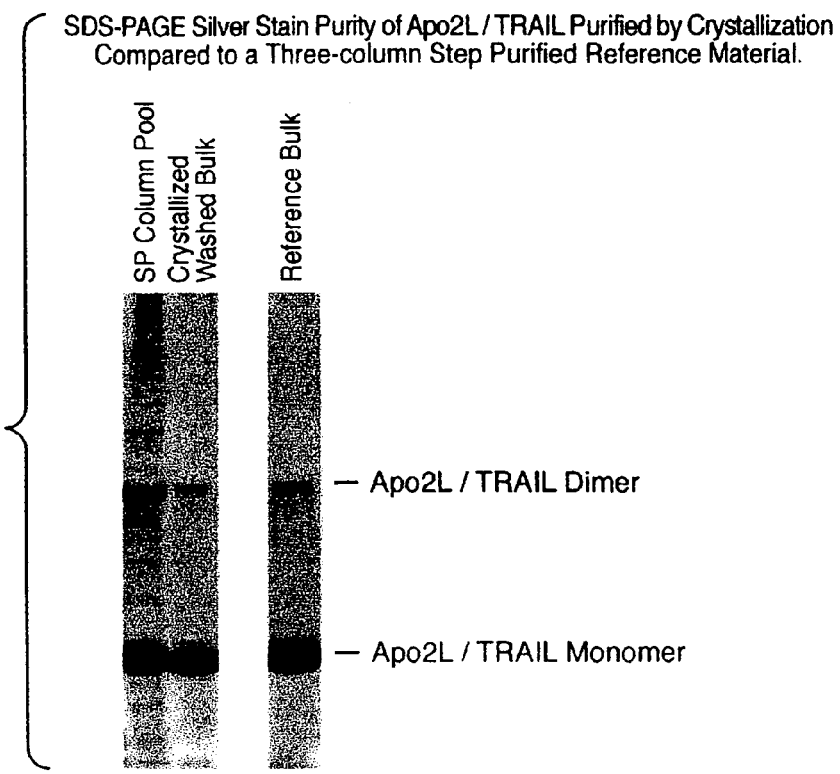

FIG._13 SDS-PAGE Silver Stain Purity of Apo2L / TRAIL Purified by Crystallization Compared to a Three-column Step Purified Reference Material.

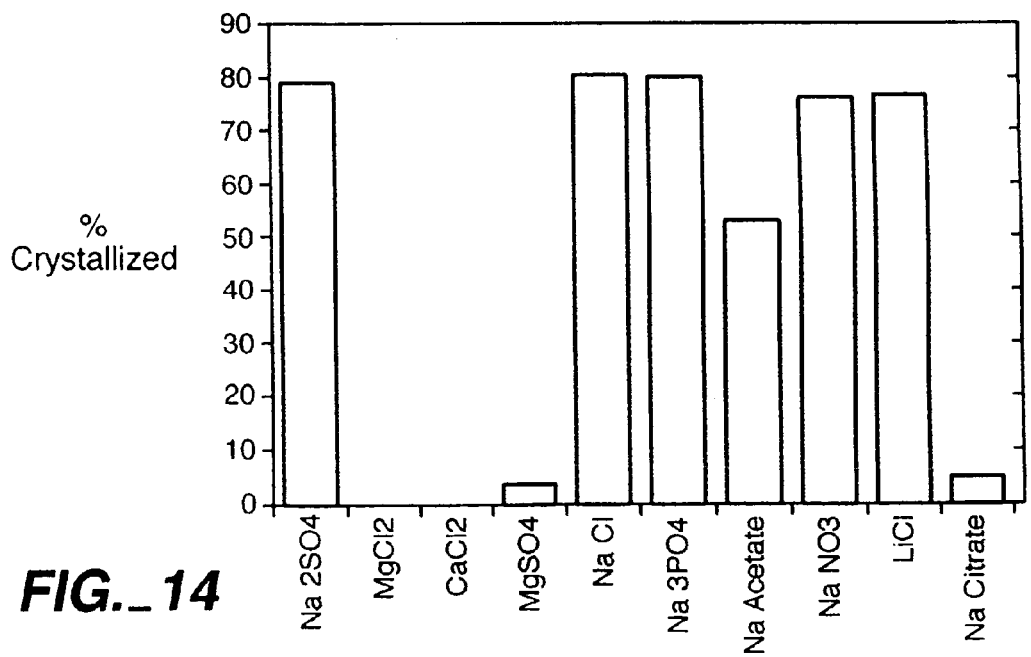

FIG._14 Effect of Salt Type on Crystallization of Partially Purified Apo2L / TRAIL. After Partial Purification of E. Coli Clarified Lysates on Sp-sepharose Cation Exchange Column, the Protein Was Eluted At 5-10 mg / ml in 20 mM Tris, pH 8 and 0.2M of One of the Salts Shown. The Samples Were Stored At 2-8°C For 3-7 Days. An Aliquot was Then Filtered and the Soluble Protein Concentration was Measured by UV Spec Scan.

SEQUENCE LISTING

<160> NUMBER OF SEQ ID NOS: 2

<210> SEQ ID NO 1
<211> LENGTH: 281
<212> TYPE: PRT
<213> ORGANISM: Homo sapiens

<400> SEQUENCE: 1

Met Ala Met Met Glu Val Gln Gly Gly Pro Ser Leu Gly Gln Thr
 1               5                  10                  15

Cys Val Leu Ile Val Ile Phe Thr Val Leu Leu Gln Ser Leu Cys
                20                  25                  30

Val Ala Val Thr Tyr Val Tyr Phe Thr Asn Glu Leu Lys Gln Met
                35                  40                  45

Gln Asp Lys Tyr Ser Lys Ser Gly Ile Ala Cys Phe Leu Lys Glu
                50                  55                  60

Asp Asp Ser Tyr Trp Asp Pro Asn Asp Glu Glu Ser Met Asn Ser
                65                  70                  75

Pro Cys Trp Gln Val Lys Trp Gln Leu Arg Gln Leu Val Arg Lys
                80                  85                  90

Met Ile Leu Arg Thr Ser Glu Glu Thr Ile Ser Thr Val Gln Glu
                95                 100                 105

Lys Gln Gln Asn Ile Ser Pro Leu Val Arg Glu Arg Gly Pro Gln
               110                 115                 120

Arg Val Ala Ala His Ile Thr Gly Thr Arg Gly Arg Ser Asn Thr
               125                 130                 135

Leu Ser Ser Pro Asn Ser Lys Asn Glu Lys Ala Leu Gly Arg Lys
               140                 145                 150

Ile Asn Ser Trp Glu Ser Ser Arg Ser Gly His Ser Phe Leu Ser
               155                 160                 165

Asn Leu His Leu Arg Asn Gly Glu Leu Val Ile His Glu Lys Gly
               170                 175                 180

Phe Tyr Tyr Ile Tyr Ser Gln Thr Tyr Phe Arg Phe Gln Glu Glu
               185                 190                 195

Ile Lys Glu Asn Thr Lys Asn Asp Lys Gln Met Val Gln Tyr Ile
               200                 205                 210

Tyr Lys Tyr Thr Ser Tyr Pro Asp Pro Ile Leu Leu Met Lys Ser
               215                 220                 225

Ala Arg Asn Ser Cys Trp Ser Lys Asp Ala Glu Tyr Gly Leu Tyr
               230                 235                 240

Ser Ile Tyr Gln Gly Gly Ile Phe Glu Leu Lys Glu Asn Asp Arg
               245                 250                 255

Ile Phe Val Ser Val Thr Asn Glu His Leu Ile Asp Met Asp His
               260                 265                 270

Glu Ala Ser Phe Phe Gly Ala Phe Leu Val Gly
               275                 280

<210> SEQ ID NO 2
<211> LENGTH: 1042
<212> TYPE: DNA
<213> ORGANISM: Homo sapiens
<220> FEATURE:
<221> NAME/KEY: unsure
<222> LOCATION: 447
<223> OTHER INFORMATION: unknown base

```
<400> SEQUENCE: 2
tttcctcact gactataaaa gaatagagaa ggaagggctt cagtgaccgg        50
ctgcctggct gacttacagc agtcagactc tgacaggatc atggctatga       100
tggaggtcca gggggaccc  agcctgggac agacctgcgt gctgatcgtg       150
atcttcacag tgctcctgca gtctctctgt gtggctgtaa cttacgtgta       200
ctttaccaac gagctgaagc agatgcagga caagtactcc aaaagtggca       250
ttgcttgttt cttaaaagaa gatgacagtt attgggaccc caatgacgaa       300
gagagtatga acagcccctg ctggcaagtc aagtggcaac tccgtcagct       350
cgttagaaag atgattttga gaacctctga ggaaaccatt tctacagttc       400
aagaaaagca acaaaatatt tctcccctag tgagagaaag aggtccncag       450
agagtagcag ctcacataac tgggaccaga ggaagaagca acacattgtc       500
ttctccaaac tccaagaatg aaaaggctct gggccgcaaa ataaactcct       550
gggaatcatc aaggagtggg cattcattcc tgagcaactt gcacttgagg       600
aatggtgaac tggtcatcca tgaaaaaggg ttttactaca tctattccca       650
aacatacttt cgatttcagg aggaaataaa agaaaacaca aagaacgaca       700
aacaaatggt ccaatatatt tacaaataca caagttatcc tgaccctata       750
ttgttgatga aaagtgctag aaatagttgt tggtctaaag atgcagaata       800
tggactctat tccatctatc aagggggaat atttgagctt aaggaaaatg       850
acagaatttt tgtttctgta acaaatgagc acttgataga catggaccat       900
gaagccagtt ttttcggggc cttttttagtt ggctaactga cctggaaaga       950
aaaagcaata acctcaaagt gactattcag ttttcaggat gatacactat      1000
gaagatgttt caaaaaatct gaccaaaaca aacaaacaga aa              1042
```

APO-2 LIGAND/TRAIL FORMULATIONS

RELATED APPLICATIONS

This application is a continuation of application Ser. No. 10/771,254 filed Feb. 3, 2004 (now abandoned), which is a continuation-in-part application of international application PCT/US02/36251 (designating the US) filed Nov. 12, 2002, which claims benefit of U.S. provisional application No. 60/338,249 filed Nov. 13, 2001 (now abandoned), the contents of which are hereby incorporated by reference.

FIELD OF THE INVENTION

The present invention relates generally to Apo2L/TRAIL formulations. In particular, such Apo2L/TRAIL formulations include lyophilized and crystal compositions.

BACKGROUND OF THE INVENTION

Various molecules, such as tumor necrosis factor-alpha ("TNF-alpha"), tumor necrosis factor-beta ("TNF-beta" or "lymphotoxin-alpha"), lymphotoxin-beta ("LT-beta"), CD30 ligand, CD27 CD40 ligand, OX-40 ligand, 4-1BB ligand, Apo-1 ligand (also referred to as Fas ligand or CD95 ligand), Apo-2 ligand (also referred to as Apo2L or TRAIL), Apo-3 ligand (also referred to as TWEAK), APRIL, OPG ligand (also referred to as RANK ligand, ODF, or TRANCE), and TALL-1 (also referred to as BlyS, BAFF or THANK) have been identified as members of the tumor necrosis factor ("TNF") family of cytokines [See, e.g., Gruss and Dower, *Blood*, 85:3378-3404 (1995); Schmid et al., *Proc. Natl. Acad. Sci.*, 83:1881 (1986); Dealtry et al., *Eur. J. Immunol.*, 17:689 (1987); Pitti et al., *J. Biol. Chem.*, 271:12687-12690 (1996); Wiley et al., *Immunity*, 3:673-682 (1995); Browning et al., *Cell*, 72:847-856 (1993); Armitage et al. *Nature*, 357:80-82 (1992), WO 97/01633 published Jan. 16, 1997; WO 97/25428 published Jul. 17, 1997; Marsters et al., *Curr. Biol.*, 8:525-528 (1998); Chicheportiche et al., *Biol. Chem.*, 272:32401-32410 (1997); Hahne et al., *J. Exp. Med.*, 188:1185-1190 (1998); WO98/28426 published Jul. 2, 1998; WO98/46751 published Oct. 22, 1998; WO/98/18921 published May 7, 1998; Moore et al., *Science*, 285:260-263 (1999); Shu et al., *J. Leukocyte Biol.*, 65:680 (1999); Schneider et al., *J. Exp. Med.*, 189: 1747-1756 (1999); Mukhopadhyay et al., *J. Biol. Chem.*, 274:15978-15981 (1999)]. Among these molecules, TNF-alpha, TNF-beta, CD30 ligand, 4-1BB ligand, Apo-1 ligand, Apo-2 ligand (Apo2L/TRAIL) and Apo-3 ligand (TWEAK) have been reported to be involved in apoptotic cell death.

Apo2L/TRAIL was identified several years ago as a member of the TNF family of cytokines. [see, e.g., Wiley et al., *Immunity*, 3:673-682 (1995); Pitti et al., *J. Biol. Chem.*, 271: 12697-12690 (1996)] The full-length human Apo2L/TRAIL polypeptide is a 281 amino acid long, Type II transmembrane protein. Some cells can produce a natural soluble form of the polypeptide, through enzymatic cleavage of the polypeptide's extracellular region [Mariani et al., *J. Cell. Biol.*, 137: 221-229 (1997)]. Crystallographic studies of soluble forms of Apo2L/TRAIL reveal a homotrimeric structure similar to the structures of TNF and other related proteins [Hymowitz et al., *Molec. Cell*, 4:563-571 (1999); Hymowitz et al., *Biochemistry*, 39:633-644 (2000)]. Apo2L/TRAIL, unlike other TNF family members however, was found to have a unique structural feature in that three cysteine residues (at position 230 of each subunit in the homotrimer) together coordinate a zinc atom, and that the zinc binding is important for trimer stability and biological activity. [Hymowitz et al., supra; Bodmer et al., *J. Biol. Chem.*, 275:20632-20637 (2000)]

It has been reported in the literature that Apo2L/TRAIL may play a role in immune system modulation, including autoimmune diseases such as rheumatoid arthritis, and in the treatment of HIV [see, e.g., Thomas et al., *J. Immunol.*, 161: 2195-2200 (1998); Johnsen et al., *Cytokine*, 11:664-672 (1999); Griffith et al., *J. Exp. Med.*, 189:1343-1353 (1999); Song et al., *J. Exp. Med.*, 191:1095-1103 (2000); Jeremias et al., *Eur. J. Immunol.*, 28:143-152 (1998); Katsikis et al., *J. Exp. Med.*, 186:1365-1372 (1997); Miura et al., *J. Exp. Med.*, 193:651-660 (2001)].

Soluble forms of Apo2L/TRAIL have also been reported to induce apoptosis in a variety of cancer cells in vitro, including colon, lung, breast, prostate, bladder, kidney, ovarian and brain tumors, as well as melanoma, leukemia, and multiple myeloma [see, e.g., Wiley et al., supra; Pitti et al., supra; Rieger et al., *FEBS Letters*, 427:124-128 (1998); Ashkenazi et al., *J. Clin. Invest.*, 104:155-162 (1999); Walczak et al., *Nature Med.*, 5:157-163 (1999); Keane et al., *Cancer Research*, 59:734-741 (1999); Mizutani et al., *Clin. Cancer Res.*, 5:2605-2612 (1999); Gazitt, *Leukemia*, 13:1817-1824 (1999); Yu et al., *Cancer Res.*, 60:2384-2389 (2000); Chinnaiyan et al., *Proc. Natl. Acad. Sci.*, 97:1754-1759 (2000)]. In vivo studies in murine tumor models further suggest that Apo2L/TRAIL, alone or in combination with chemotherapy or radiation therapy, can exert substantial anti-tumor effects [see, e.g., Ashkenazi et al., supra; Walzcak et al., supra; Gliniak et al., *Cancer Res.*, 59:6153-6158 (1999); Chinnaiyan et al., supra; Roth et al., *Biochem. Biophys. Res. Comm.*, 265: 1999 (1999)]. In contrast to many types of cancer cells, most normal human cell types appear to be resistant to apoptosis induction by certain recombinant forms of Apo2L/TRAIL [Ashkenazi et al., supra; Walzcak et al., supra]. Jo et al. has reported that a polyhistidine-tagged soluble form of Apo2L/TRAIL induced apoptosis in vitro in normal isolated human, but not non-human, hepatocytes [Jo et al., *Nature Med.*, 6:564-567 (2000); see also, Nagata, *Nature Med.*, 6:502-503 (2000)]. It is believed that certain recombinant Apo2L/TRAIL preparations may vary in terms of biochemical properties and biological activities on diseased versus normal cells, depending, for example, on the presence or absence of a tag molecule, zinc content, and % trimer content [See, Lawrence et al., *Nature Med., Letter to the Editor*, 7:383-385 (2001); Qin et al., *Nature Med., Letter to the Editor*, 7:385-386 (2001)].

Induction of various cellular responses mediated by such TNF family cytokines is believed to be initiated by their binding to specific cell receptors. Previously, two distinct TNF receptors of approximately 55-kDa (TNFR1) and 75-kDa (TNFR2) were identified [Hohman et al., *J. Biol. Chem.*, 264:14927-14934 (1989); Brockhaus et al., *Proc. Natl. Acad. Sci.*, 87:3127-3131 (1990); EP 417,563, published Mar. 20, 1991; Loetscher et al., *Cell*, 61:351 (1990); Schall et al., *Cell*, 61:361 (1990); Smith et al., *Science*, 248: 1019-1023 (1990); Lewis et al., *Proc. Natl. Acad. Sci.*, 88:2830-2834 (1991); Goodwin et al., *Mol. Cell. Biol.*, 11:3020-3026 (1991)]. Those TNFRs were found to share the typical structure of cell surface receptors including extracellular, transmembrane and intracellular regions. The extracellular portions of both receptors were found naturally also as soluble TNF-binding proteins [Nophar, Y. et al., *EMBO J.*, 9:3269 (1990); and Kohno, T. et al., *Proc. Natl. Acad. Sci. U.S.A.*, 87:8331 (1990); Hale et al., *J. Cell. Biochem. Supplement* 15F, 1991, p. 113 (P424)].

The extracellular portion of type 1 and type 2 TNFRs (TNFR1 and TNFR2) contains a repetitive amino acid sequence pattern of four cysteine-rich domains (CRDs) designated 1 through 4, starting from the $NH_2$-terminus. [Schall et al., supra; Loetscher et al., supra; Smith et al., supra; Nophar et al., supra; Kohno et al., supra; Banner et al., *Cell*, 73:431-435 (1993)]. A similar repetitive pattern of CRDs exists in several other cell-surface proteins, including the p75 nerve growth factor receptor (NGFR) [Johnson et al., *Cell*, 47:545 (1986); Radeke et al., *Nature*, 325:593 (1987)], the B cell antigen CD40 [Stamenkovic et al., *EMBO J.*, 8:1403 (1989)], the T cell antigen OX40 [Mallet et al., *EMBO J.*, 9:1063 (1990)] and the Fas antigen [Yonehara et al., supra and Itoh et al., *Cell*, 66:233-243 (1991)]. CRDs are also found in the soluble TNFR (sTNFR)-like T2 proteins of the Shope and myxoma poxviruses [Upton et al., *Virology*, 160:20-29 (1987); Smith et al., *Biochem. Biophys. Res. Commun.*, 176:335 (1991); Upton et al., *Virology*, 184:370 (1991)]. Optimal alignment of these sequences indicates that the positions of the cysteine residues are well conserved. These receptors are sometimes collectively referred to as members of the TNF/NGF receptor superfamily.

The TNF family ligands identified to date, with the exception of lymphotoxin-beta, are typically type II transmembrane proteins, whose C-terminus is extracellular. In contrast, most receptors in the TNF receptor (TNFR) family identified to date are typically type I transmembrane proteins. In both the TNF ligand and receptor families, however, homology identified between family members has been found mainly in the extracellular domain ("ECD"). Several of the TNF family cytokines, including TNF-alpha, Apo-1 ligand and CD40 ligand, are cleaved proteolytically at the cell surface; the resulting protein in each case typically forms a homotrimeric molecule that functions as a soluble cytokine. TNF receptor family proteins are also usually cleaved proteolytically to release soluble receptor ECDs that can function as inhibitors of the cognate cytokines.

Pan et al. have disclosed another TNF receptor family member referred to as "DR4" [Pan et al., *Science*, 276:111-113 (1997); see also WO98/32856 published Jul. 30, 1998]. The DR4 was reported to contain a cytoplasmic death domain capable of engaging the cell suicide apparatus. Pan et al. disclose that DR4 is believed to be a receptor for the ligand known as Apo2L/TRAIL.

In Sheridan et al., *Science*, 277:818-821 (1997) and Pan et al., *Science*, 277:815-818 (1997), another molecule believed to be a receptor for Apo2L/TRAIL is described [see also, WO98/51793 published Nov. 19, 1998; WO98/41629 published Sep. 24, 1998]. That molecule is referred to as DR5 (it has also been alternatively referred to as Apo-2; TRAIL-R, TR6, Tango-63, hAP08, TRICK2 or KILLER [Screaton et al., *Curr. Biol.*, 7:693-696 (1997); Walczak et al., *EMBO J.*, 16:5386-5387 (1997); Wu et al., *Nature Genetics*, 17:141-143 (1997); WO98/35986 published Aug. 20, 1998; EP870,827 published Oct. 14, 1998; WO98/46643 published Oct. 22, 1998; WO99/02653 published Jan. 21, 1999; WO99/09165 published Feb. 25, 1999; WO99/11791 published Mar. 11, 1999]. Like DR4, DR5 is reported to contain a cytoplasmic death domain and be capable of signaling apoptosis. The crystal structure of the complex formed between Apo-2L/TRAIL and DR5 is described in Hymowitz et al., *Molecular Cell*, 4:563-571 (1999).

A further group of recently identified receptors are referred to as "decoy receptors," which are believed to function as inhibitors, rather than transducers of signaling. This group includes DCR1 (also referred to as TRID, LIT or TRAIL-R3) [Pan et al., *Science*, 276:111-113 (1997); Sheridan et al., *Science*, 277:818-821 (1997); McFarlane et al., *J. Biol. Chem.*, 272:25417-25420 (1997); Schneider et al., *FEBS Letters*, 416:329-334 (1997); Degli-Esposti et al., *J. Exp. Med.*, 186:1165-1170 (1997); and Mongkolsapaya et al., *J. Immunol.*, 160:3-6 (1998)] and DCR2 (also called TRUNDD or TRAIL-R4) [Marsters et al., *Curr. Biol.*, 7:1003-1006 (1997); Pan et al., *FEBS Letters*, 424:41-45 (1998); Degli-Esposti et al., *Immunity*, 7:813-820 (1997)], both cell surface molecules, as well as OPG [Simonet et al., supra; Emery et al., infra] and DCR3 [Pitti et al., *Nature*, 396:699-703 (1998)], both of which are secreted, soluble proteins. Apo2L/TRAIL has been reported to bind those receptors referred to as DcR1, DcR2 and OPG.

Apo2L/TRAIL is believed to act through the cell surface "death receptors" DR4 and DR5 to activate caspases, or enzymes that carry out the cell death program. Upon ligand binding, both DR4 and DR5 can trigger apoptosis independently by recruiting and activating the apoptosis initiator, caspase-8, through the death-domain-containing adaptor molecule referred to as FADD/Mort1 [Kischkel et al., *Immunity*, 12:611-620 (2000); Sprick et al., *Immunity*, 12:599-609 (2000); Bodmer et al., *Nature Cell Biol.*, 2:241-243 (2000)]. In contrast to DR4 and DR5, the DcR1 and DcR2 receptors do not signal apoptosis.

For a review of the TNF family of cytokines and their receptors, see Ashkenazi and Dixit, *Science*, 281:1305-1308 (1998); Ashkenazi and Dixit, *Curr. Opin. Cell Biol.*, 11:255-260 (2000); Golstein, *Curr. Biol.*, 7:750-753 (1997); Gruss and Dower, supra; Nagata, *Cell*, 88:355-365 (1997); Locksley et al., *Cell*, 104:487-501 (2001).

SUMMARY OF THE INVENTION

Certain proteins, such as Apo2L/TRAIL and other members of the TNF family of cytokines, exhibit biological activity when the protein is in a trimer or trimeric form. Thus, for purposes of therapeutic or even diagnostic use, formulations of such proteins are desired wherein the protein is stable and remains biologically active, particularly stable in a trimeric form. Applicants have found that certain formulation components, or "excipients", can provide stability for such proteins like Apo2L/TRAIL and enhance solubility (i.e., to reduce aggregation or precipitation of the protein). Applicants also surprisingly found that, under certain conditions, Apo2L/TRAIL can readily crystallize. Such crystal forms of Apo2L/TRAIL may be useful in preparation of suspension formulations of Apo2L/TRAIL and/or provide an effective and efficient process for protein purification.

Accordingly, the present invention provides compositions or formulations comprising Apo2L/TRAIL and one or more excipients which provide sufficient ionic strength to enhance solubility and/or stability of the Apo2L/TRAIL, wherein the composition optionally has a pH of 6 (or about 6) to 9 (or about 9). Optionally, the excipient(s) providing sufficient ionic strength is salt, and may comprise an arginine salt or sulfate salt. In one embodiment, the compositions may further comprise a buffer. Optionally, the concentration of the Apo2L/TRAIL protein in the composition is about 1 to about 100 mg/ml, about 1 to about 20 mg/ml, about 10 to about 20 mg/ml, or about 20 mg/ml. The compositions of the invention may comprise liquid formulations or lyophilized formulations. The compositions may also comprise suspension formulations in which the Apo2L/TRAIL protein is in the form of crystals. Optionally, it may be desirable to include one or more surfactants or other excipients in the composition. Such surfactants may, for instance, comprise a polysorbate or poloxamer. Particularly desired formulations are those in which the excipient(s) provide for optimized Apo2L/TRAIL trimer content and minimize the amount of Apo2L/TRAIL dimer or aggregate formation. Optionally, the formulations contain no more than 10% Apo2L/TRAIL dimer or 5% Apo2L/TRAIL aggregates (of the total amount of Apo2L/TRAIL protein in the formulation).

In optional embodiments, the present invention provides compositions comprising about 1 to about 20 mg/ml of Apo2L/TRAIL and arginine salt, wherein the composition has a pH of about 6.5 to about 8.5. Optionally, the compositions further comprise a buffer such as Tris and a surfactant such as polysorbate. Optionally, the Apo2L/TRAIL protein does not include (i.e., is not linked or fused to) any epitope tag molecule(s) or leucine zipper molecule(s).

The present invention provides compositions comprising about 1 to about 20 mg/ml of Apo2L/TRAIL, about 0.4 to about 0.5M arginine salt, and buffer, wherein the compositions have a pH of about 7 to about 7.5. The Apo2L/TRAIL protein may be human Apo2L/TRAIL protein comprising amino acid residues 114 to 281 of FIG. 1. Optionally, the Apo2L/TRAIL protein is recombinantly expressed in host cells such as E. coli.

In addition, the invention provides methods for preparing the compositions described above. In the methods, the compositions are prepared by admixing or combining Apo2L/TRAIL and one or more excipients which provide sufficient ionic strength to enhance solubility and/or stability of the Apo2L/TRAIL, wherein the composition has a pH of 6 (or about 6) to 9 (or about 9). Optionally, the excipient(s) providing sufficient ionic strength is salt, and may comprise an arginine salt or sulfate salt. A buffer may also be included to maintain the pH of the composition, and optionally to maintain the pH at about 6.5 to about 7.5. Optionally, the concentration of the Apo2L/TRAIL protein in the formulation is about 1 to about 100 mg/ml, about 1 to about 20 mg/ml, about 10 to about 20 mg/ml, or at least 20 mg/ml. In particularly desirable embodiments, the resulting compositions are pharmaceutically acceptable formulations.

In further embodiments, the invention provides compositions comprising Apo2L/TRAIL protein crystals. Preferably, the Apo2L/TRAIL protein crystal compositions contain 5% (or about 5%) to 10% (or about 10%) water. Optionally, the Apo2L/TRAIL protein crystal compositions may contain one or more excipients such as sucrose, trehalose, arginine, Tween 20, or Captisol™.

In still further embodiments, the invention provides methods of making compositions comprising Apo2L/TRAIL crystals.

In yet further embodiments, the invention provides methods of making and purifying Apo2L/TRAIL.

In additional embodiments, the invention provides kits comprising:
(a) a container comprising an Apo2L/TRAIL composition described herein and
(b) instructions for using the Apo2L/TRAIL composition; such as for using the composition to treat a disorder against which the composition is effective. Optionally, the disorder is cancer, and more particularly, is a breast, lung, or colon (or colorectal) cancer.

In still further aspects, the invention provides methods for treating a disorder, such as cancer or an immune related disorder, in a mammal comprising administering to the mammal, optionally by either injection or infusion, an effective amount of an Apo2L/TRAIL composition provided by the present invention.

In more particular embodiments of the invention the following are provided:

A stable formulation of Apo-2 ligand, comprising Apo-2 ligand and about 0.2M to about 0.5M salt, wherein said formulation has a pH of about 6 to about 9. Optionally, the salt is an arginine salt or sodium sulphate. Optionally, the concentration of the arginine salt in the formulation is about 0.4M to about 0.5 M. The arginine salt may include arginine succinate, arginine sulphate, arginine malate, arginine citrate, arginine tartrate, or arginine phosphate. The Apo-2 ligand may optionally comprise crystallized protein. The formulation may comprise a lyophilized or suspension formulation. Optionally, the pH of the formulation is about 6.5 to about 8.5, and optionally, about 7 to about 7.5. Optionally, the formulation further comprises surfactant, such as a polysorbate or poloxamer. Optionally, the concentration of the surfactant in the formulation is about 0.005% to about 0.2%. Optionally, the formulation further comprises buffer, such as Tris buffer or Hepes. Optionally, the formulation further comprises one or more divalent metal ions or a preservative. Optionally, the formulation is storage-stable for at least 12 months.

A stable, lyophilized formulation of Apo-2 ligand, comprising about 1 mg/ml to about 20 mg/ml Apo-2 ligand, about 0.2 M to about 0.5M arginine salt, buffer, and surfactant, wherein said formulation has a pH of about 6 to about 9. Optionally, the arginine salt is arginine succinate, and the concentration of the arginine succinate may be about 0.4M to about 0.5M. Optionally, the buffer is Tris buffer, and the surfactant is a polysorbate. Optionally, the formulation further comprises one or more divalent metal ions.

A stable formulation of Apo-2 ligand, comprising about 1 mg/ml to about 20 mg/ml Apo-2 ligand, about 0.2M to about 0.5 M salt, buffer, and surfactant, wherein said Apo-2 ligand comprises crystallized protein and said formulation has a pH of about 6 to about 9. Optionally, the salt is sodium sulphate, and the buffer is Tris buffer. Optionally, the surfactant is polysorbate, and the pH is about 7 to about 7.5.

A stable formulation of Apo-2 ligand, comprising about 0.1 mg/ml to about 2 mg/ml Apo-2 ligand, sugar, and surfactant, wherein said formulation has a pH of about 6 to about 9. Optionally, the sugar is trehalose, and the concentration of the sugar in the formulation may be about 1% to about 8%. Optionally, the formulation is lyophilized.

A stable Apo2L/TRAIL protein crystal composition, comprising about 5% to about 10% water. Optionally, the Apo2L/TRAIL protein crystal composition comprises one or more excipients such as sucrose, trehalose, arginine, Tween 20, or Captisol™.

A method of making a stable formulation of Apo-2 ligand, comprising steps of (a) providing about 1 mg/ml to about 20 mg/ml Apo-2 ligand, about 0.2 M to about 0.5M arginine salt, buffer, and surfactant, (b) combining or mixing the ingredients of step (a) to make a formulation, and (c) adjusting the pH of the formulation of step (b) to about 6 to about 9. Optionally, the arginine salt is arginine succinate, and the concentration of the arginine succinate is about 0.4M to about 0.5M. Optionally, the buffer is Tris buffer, and the surfactant is a polysorbate.

A method of making crystallized Apo-2 ligand, comprising steps of (a) providing Apo-2 ligand, buffer, and monovalent cationic salt, (b) combining or mixing the ingredients of step (a) to make a formulation at a temperature of about 20° C. to about 30° C., and (c) lowering the temperature of the formulation of step (b) to about 2° C. to about 8° C.; wherein Apo-2 ligand crystallization occurs as the temperature of the formulation of step (b) is lowered. Optionally, the salt is sodium sulphate or sodium chloride. The concentration of the salt may be about 0.1M to about 0.15M. Optionally, the formulation of step (b) is agitated as the temperature is lowered in step (c). Optionally, the method further comprises a step (d) in which the Apo-2 ligand crystals are dried. Optionally, prior to the step (d), the Apo-2 ligand crystals are washed.

A method of making Apo-2 ligand, comprising the steps of: (a) providing host cells comprising a vector containing DNA encoding Apo-2 ligand; (b) culturing the host cells in culture medium under conditions sufficient to express Apo-2 ligand; (c) obtaining said expressed Apo-2 ligand from the host cells and culture medium; (d) formulating said Apo-2 ligand into a solution containing sodium chloride or sodium sulphate to make a formulation at a temperature of about 20° C. to about 30° C., and (e) lowering the temperature of said formulation of step (d) to about 2° C. to about 8° C., wherein Apo-2 ligand crystals form when the temperature of step (e) is lowered. Optionally, prior to step (d), the Apo-2 ligand protein is concentrated, and the protein may be concentrated by centrifugation, column chromatography or ultrafiltration. Optionally, step (d) is conducted by applying the Apo-2 ligand to a chromatographic column (such as a cation exchange column) and eluting the Apo-2 ligand into a sodium chloride or sodium sulphate containing buffer. Optionally, step (d) is further conducted by including polyethelene glycol to the pool as the chromatography is performed. Optionally, the cation exchange column comprises SP-Sepharose fast flow, CM-Sepharose fast flow, or Macro-prep ceramic HS, and the buffer solution contains 50 mM Hepes, 50 mM Tris, 50 mM triethanolamine, 0.05% Triton X 100, 1 mM DTT, pH 7.5-8.0. Optionally, the formulation is agitated during step (e). Optionally, the pH of the formulation in step (d) is about 6.5 to about 8.5. Optionally, the host cells are prokaryote cells, such as E. coli.

A device for administering a formulation of Apo-2 ligand to a mammal, comprising a container holding at least one dosage unit of the Apo-2 ligand formulations described herein. Optionally, the device is a pen injector device, and the container is a cartridge.

An article of manufacture, comprising a container which includes an Apo2L/TRAIL formulation described herein, and printed instructions for use of the Apo-2L/TRAIL formulation. Optionally, the container is a bottle, vial, syringe, or test tube. Optionally, the article of manufacture comprises a second container which includes water-for-injection, saline, Ringer's solution, or dextrose solution.

A method of inducing apoptosis in mammalian cells, comprising exposing mammalian cells to an effective amount of an Apo-2 ligand formulation described herein. The mammalian cells may be cancer cells.

A method of treating cancer in a mammal, comprising administering to a mammal diagnosed as having cancer an effective amount of an Apo-2 ligand formulation described herein.

BRIEF DESCRIPTION OF THE DRAWINGS

FIG. 1 shows the nucleotide sequence of human Apo-2L/TRAIL cDNA (SEQ ID NO:2) and its derived amino acid sequence (SEQ ID NO:1). The "N" at nucleotide position 447 (in SEQ ID NO:2) is used to indicate the nucleotide base may be a "T" or "G".

FIG. 2 shows data (% trimer remaining and % IEX main peak remaining) for various Apo2L/TRAIL formulations after 1 week storage at 30° C.

FIG. 3A shows data (% trimer remaining and % IEX main peak remaining) for various Apo2L/TRAIL formulations after 4 months storage at 40° C.

FIG. 3B shows data (% trimer remaining, % monomer, and % IEX main peak remaining) for various Apo2L/TRAIL formulations after 1 month storage at 50° C.

FIG. 3C shows an Arrhenius plot predictive of shelf-life for the described Apo2L/TRAIL formulation.

FIGS. 4A-4B show graphs of % bioactivity and % trimer of two different formulations at varying pH.

FIG. 5 illustrates the structure of Apo2L/TRAIL and coordination of the structure by an intrinsic zinc molecule.

FIG. 6 shows the effects of varying concentrations of polysorbate on stability of an Apo2L/TRAIL formulation.

FIG. 7 shows the effects of varying concentrations of zinc on stability of an Apo2L/TRAIL formulation.

FIG. 8 shows the equilibrium solubility and crystallization of Apo2L/TRAIL in a sodium sulphate formulation.

FIG. 9 shows the equilibrium solubility and crystallization of Apo2L/TRAIL in various salt concentrations.

FIG. 10A shows the effects of agitation rates on crystallization of Apo2L/TRAIL.

FIG. 10B shows the dissolution profile of Apo2L/TRAIL crystals under agitation.

FIG. 10C shows the effects of agitation rate on Apo2L/TRAIL crystal size distribution.

FIG. 11A shows the IEX profile of the Apo2L/TRAIL after reconstitution of vacuum dried crystals.

FIG. 11B shows the bioactivity of the Apo2L/TRAIL after reconstitution of the vacuum dried crystals.

FIG. 12 shows an Arrhenius plot predictive of shelf-life for the described Apo2L/TRAIL formulation.

FIG. 13 shows a SDS-PAGE silver stain gel illustrating purity of the described Apo2L/TRAIL preparations.

FIG. 14 shows the effects of various salts on crystallization of Apo2L/TRAIL.

DETAILED DESCRIPTION OF THE INVENTION

A. Definitions

Figure 15A:
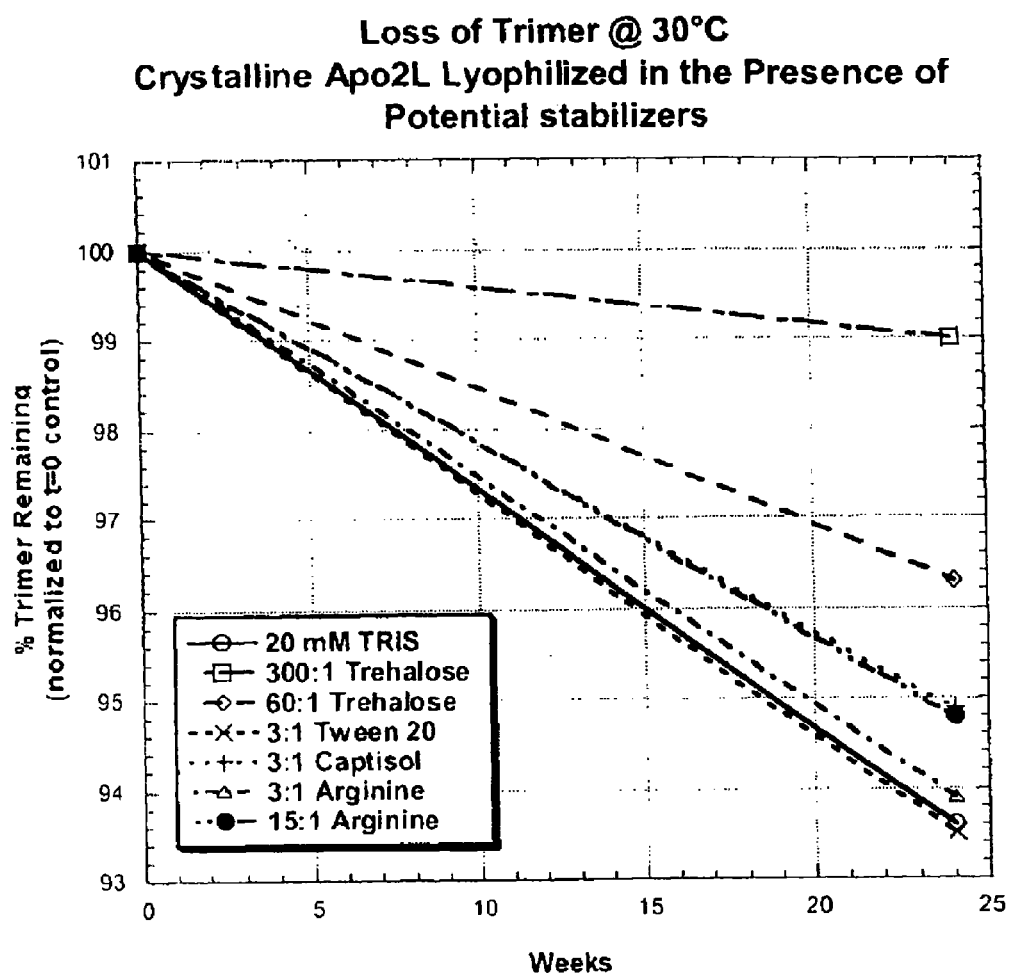
FIGS. 15A-15C show the effects of various excipients on the stability of lyophilized Apo2L/TRAIL crystals.

"TNF family member" is used in a broad sense to refer to various polypeptides that share some similarity to tumor necrosis factor (TNF) with respect to structure or function. Certain structural and functional characteristics associated with the TNF family of polypeptides are known in the art and described, for example, in the above Background of the Invention. Such polypeptides include but are not limited to those polypeptides referred to in the art as TNF-alpha, TNF-beta, CD40 ligand, CD30 ligand, CD27 ligand, OX-40 ligand, 4-1BB ligand, Apo-1 ligand (also referred to as Fas ligand or CD95 ligand), Apo-2L/TRAIL (also referred to as TRAIL), Apo-3 ligand (also referred to as TWEAK), APRIL, OPG ligand (also referred to as RANK ligand, ODF, or TRANCE), and TALL-1 (also referred to as BlyS, BAFF or THANK) (See, e.g., Gruss and Dower, Blood 1995, 85:3378-3404; Pitti et al., J. Biol. Chem. 1996, 271:12687-12690; Wiley et al., Immunity 1995, 3:673-682; Browning et al., Cell 1993, 72:847-856; Armitage et al. Nature 1992, 357:80-82, PCT Publication Nos. WO 97/01633; and WO 97/25428; Marsters et al., Curr. Biol. 1998, 8:525-528; Chicheportiche et al., Biol. Chem. 1997, 272:32401-32410; Hahne et al., J. Exp. Med. 1998, 188:1185-1190; PCT Publication Nos. WO98/28426; WO98/46751; and WO/98/18921; Moore et al., Science 1999, 285:260-263; Shu et al., *J. Leukocyte Biol.* 1999, 65:680; Schneider et al., *J. Exp. Med.* 1999, 189:1747-1756; Mukhopadhyay et al., *J. Biol. Chem.* 1999, 274:15978-15981).

The terms "Apo2L/TRAIL", "Apo2L", "Apo-2 ligand" and "TRAIL" are used herein to refer to a polypeptide sequence which includes amino acid residues 114-281, inclusive, 95-281, inclusive, residues 92-281, inclusive, residues 91-281, inclusive, residues 41-281, inclusive, residues 15-281, inclusive, or residues 1-281, inclusive, of the amino acid sequence shown in FIG. 1 (SEQ ID NO:1), as well as biologically active fragments, deletional, insertional, or substitutional variants of the above sequences. In one embodiment, the polypeptide sequence comprises residues 114-281 of FIG. 1 (SEQ ID NO:1), and optionally, consists of residues 114-281 of FIG. 1 (SEQ ID NO:1). Optionally, the polypeptide sequence comprises residues 92-281 or residues 91-281 of FIG. 1 (SEQ ID NO:1). The Apo-2L polypeptides may be encoded by the native nucleotide sequence shown in FIG. 1 (SEQ ID NO:2). Optionally, the codon which encodes residue Pro119 (FIG. 1; SEQ ID NO:2) may be "CCT" or "CCG". In other embodiments, the fragments or variants are biologically active and have at least about 80% amino acid sequence identity, more preferably at least about 90% sequence identity, and even more preferably, at least 95%, 96%, 97%, 98%, or 99% sequence identity with any one of the above recited Apo2L/TRAIL sequences. Optionally, the Apo2L/TRAIL polypeptide is encoded by a nucleotide sequence which hybridizes under stringent conditions with the encoding polynucleotide sequence provided in FIG. 1 (SEQ ID NO:2). The definition encompasses substitutional variants of Apo2L/TRAIL in which at least one of its native amino acids are substituted by an alanine residue. Particular substitutional variants of the Apo2L/TRAIL include those in which at least one amino acid is substituted by an alanine residue. These substitutional variants include those identified, for example, as "D203A"; "D218A" and "D269A." This nomenclature is used to identify Apo2L/TRAIL variants wherein the aspartic acid residues at positions 203, 218, and/or 269 (using the numbering shown in FIG. 1 (SEQ ID NO:1)) are substituted by alanine residues. Optionally, the Apo2L variants may comprise one or more of the alanine substitutions which are recited in Table I of published PCT application WO 01/00832. Substitutional variants include one or more of the residue substitutions identified in Table I of WO 01/00832 published Jan. 4, 2001. The definition also encompasses a native sequence Apo2L/TRAIL isolated from an Apo2L/TRAIL source or prepared by recombinant or synthetic methods. The Apo2L/TRAIL of the invention includes the polypeptides referred to as Apo2L/TRAIL or TRAIL disclosed in PCT Publication Nos. WO97/01633 and WO97/25428. The terms "Apo2L/TRAIL" or "Apo2L" are used to refer generally to forms of the Apo2L/TRAIL which include monomer, dimer or trimer forms of the polypeptide. All numbering of amino acid residues referred to in the Apo2L sequence use the numbering according to FIG. 1 (SEQ ID NO:1), unless specifically stated otherwise. For instance, "D203" or "Asp203" refers to the aspartic acid residue at position 203 in the sequence provided in FIG. 1 (SEQ ID NO:1).

The term "Apo2L/TRAIL extracellular domain" or "Apo2L/TRAIL ECD" refers to a form of Apo2L/TRAIL which is essentially free of transmembrane and cytoplasmic domains. Ordinarily, the ECD will have less than 1% of such transmembrane and cytoplasmic domains, and preferably, will have less than 0.5% of such domains. It will be understood that any transmembrane domain(s) identified for the polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified. In preferred embodiments, the ECD will consist of a soluble, extracellular domain sequence of the polypeptide which is free of the transmembrane and cytoplasmic or intracellular domains (and is not membrane bound). Particular extracellular domain sequences of Apo-2L/TRAIL are described in PCT Publication Nos. WO97/01633 and WO97/25428.

The term "Apo2L/TRAIL monomer" or "Apo2L monomer" refers to a covalent chain of an extracellular domain sequence of Apo2L.

The term "Apo2L/TRAIL dimer" or "Apo2L dimer" refers to two Apo-2L monomers joined in a covalent linkage via a disulfide bond. The term as used herein includes free standing Apo2L dimers and Apo2L dimers that are within trimeric forms of Apo2L (i.e., associated with another, third Apo2L monomer).

The term "Apo2L/TRAIL trimer" or "Apo2L trimer" refers to three Apo2L monomers that are non-covalently associated.

The term "Apo2L/TRAIL aggregate" is used to refer to self-associated higher oligomeric forms of Apo2L/TRAIL, such as Apo2L/TRAIL trimers, which form, for instance, hexameric and nanomeric forms of Apo2L/TRAIL.

Determination of the presence and quantity of Apo2L/TRAIL monomer, dimer, or trimer (or other aggregates) may be made using methods and assays known in the art (and using commercially available materials), such as native size exclusion HPLC ("SEC"), denaturing size exclusion using sodium dodecyl sulphate ("SDS-SEC"), reverse phase HPLC, capillary electrophoresis, and including those methods described in further detail in the Examples below.

The term "tagged" when used herein refers to a chimeric polypeptide comprising Apo2L/TRAIL, or a portion thereof, fused to a "tag polypeptide". The tag polypeptide has enough residues to provide an epitope against which an antibody can be made or to provide some other function, such as metal ion chelation, yet is short enough such that it generally does not interfere with activity of the TNF family cytokine. The tag polypeptide preferably also is fairly unique so that a tag-specific antibody does not substantially cross-react with other epitopes. Suitable tag polypeptides generally have at least six amino acid residues and usually between about 8 to about 50 amino acid residues (preferably, between about 10 to about 20 residues).

The term "divalent metal ion" refers to a metal ion having two positive charges. Examples of divalent metal ions include but are not limited to zinc, cobalt, nickel, cadmium, magnesium, and manganese. Particular forms of such metals that may be employed include salt forms (e.g., pharmaceutically acceptable salt forms), such as chloride, acetate, carbonate, citrate and sulfate forms of the above mentioned divalent metal ions. Optionally, a divalent metal ion for use in the present invention is zinc, and preferably, the salt form, zinc sulfate or zinc chloride.

"Isolated," when used to describe the various proteins disclosed herein, means protein that has been identified and separated and/or recovered from a component of its natural environment. Contaminant components of its natural environment are materials that would typically interfere with diagnostic or therapeutic uses for the protein, and may include enzymes, hormones, and other proteinaceous or non-proteinaceous solutes. In preferred embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain, or (3) to homogeneity by mass spectroscopic or peptide mapping techniques. Isolated protein includes protein in situ within recombinant cells, since at least one component of the Apo2L/TRAIL natural environment will not be present. Ordinarily, however, isolated protein will be prepared by at least one purification step.

An "isolated" Apo2L/TRAIL nucleic acid molecule is a nucleic acid molecule that is identified and separated from at least one contaminant nucleic acid molecule with which it is ordinarily associated in the natural source of the Apo2L/TRAIL nucleic acid. An isolated Apo2L/TRAIL nucleic acid molecule is other than in the form or setting in which it is found in nature. Isolated Apo2L/TRAIL nucleic acid molecules therefore are distinguished from the Apo2L/TRAIL nucleic acid molecule as it exists in natural cells. However, an isolated Apo2L/TRAIL nucleic acid molecule includes Apo2L/TRAIL nucleic acid molecules contained in cells that ordinarily express Apo2L/TRAIL where, for example, the nucleic acid molecule is in a chromosomal location different from that of natural cells.

"Percent (%) amino acid sequence identity" with respect to the sequences identified herein is defined as the percentage of amino acid residues in a candidate sequence that are identical with the amino acid residues in the Apo2L/TRAIL sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art can determine appropriate parameters for measuring alignment, including assigning algorithms needed to achieve maximal alignment over the full-length sequences being compared. For purposes herein, percent amino acid identity values can be obtained using the sequence comparison computer program, ALIGN-2, which was authored by Genentech, Inc. and the source code of which has been filed with user documentation in the US Copyright Office, Washington, D.C., 20559, registered under the US Copyright Registration No. TXU510087. The ALIGN-2 program is publicly available through Genentech, Inc., South San Francisco, Calif. All sequence comparison parameters are set by the ALIGN-2 program and do not vary.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired identity between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"High stringency conditions", as defined herein, are identified by those that: (1) employ low ionic strength and high temperature for washing; 0.015 M sodium chloride/0.0015 M sodium citrate/0.1% sodium dodecyl sulfate at 50° C.; (2) employ during hybridization a denaturing agent; 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "storage-stable" is used to describe a formulation having a shelf-life acceptable for a product in the distribution chain of commerce, for instance, at least 12 months at a given temperature, and preferably, at least 24 months at a given temperature. Optionally, such a storage-stable formulation contains no more than 5% aggregates, no more than 10% dimers, and/or minimal changes in charge heterogeneity or biological activity. Degradation pathways for proteins can involve chemical instability (i.e. any process which involves modification of the protein by bond formation or cleavage resulting in a new chemical entity) or physical instability (i.e. changes in the higher order structure of the protein). Chemical instability can result from, for example, deamidation, racemization, hydrolysis, oxidation, beta elimination or disulfide exchange. Physical instability can result from, for example, denaturation, aggregation, precipitation or adsorption. The three most common protein degradation pathways are protein aggregation, deamidation and oxidation. Cleland et al. *Critical Reviews in Therapeutic Drug Carrier Systems* 10(4): 307-377 (1993).

As used herein, "soluble" refers to polypeptides that, when in aqueous solutions, are completely dissolved, resulting in a clear to slightly opalescent solution with no visible particulates, as assessed by visual inspection. A further assay of the turbidity of the solution (or solubility of the protein) may be made by measuring UV absorbances at 340 nm to 360 nm with a 1 cm pathlength cell where turbidity at 20 mg/ml is less than 0.05 absorbance units.

An "osmolyte" refers to a tonicity modifier or osmotic adjuster that lends osmolality to a solution. Osmolality refers to the total osmotic activity contributed by ions and nonionized molecules to a solution. Examples include inorganic salts such as sodium chloride, polyethylene glycols (PEGs), polypropylene glycol, sugars such as sucrose or trehalose, glycerol, amino acids, and sugar alcohols such as mannitol known to the art that are generally regarded as safe (GRAS).

"Preservatives" can act to prevent bacteria, viruses, and fungi from proliferating in the formulation, and anti-oxidants, or other compounds can function in various ways to preserve the stability of the formulation. Examples include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of compounds include aromatic alcohols such as phenol and benzyl alcohol, alkyl parabens such as methyl or propyl paraben, and m-cresol. Optionally, such compound is phenol or benzyl alcohol. The preservative or other compound will optionally be included in a liquid or aqueous form of the Apo2L/TRAIL formulation, but not usually in a lyophilized form of the formulation. In the latter case, the preservative or other compound will typically be present in the water for injection (WFI) or bacteriostatic water for injection (BWFI) used for reconstitution.

A "surfactant" can act to decrease turbidity or denaturation of a protein in a formulation. Examples of surfactants include non-ionic surfactant such as a polysorbate, e.g., polysorbates 20, 60, or 80, a poloxamer, e.g., poloxamer 184 or 188, Pluronic polyols, ethylene/propylene block polymers or any others known to the art that are GRAS. Optionally, the surfactant is a polysorbate or poloxamer.

A "buffer" as used herein is any suitable buffer that is GRAS and generally confers a pH from about 6 to about 9, optionally from about 6.5 to about 8.5, and optionally at about 7 to about 7.5, if the polypeptide is Apo2L/TRAIL. Examples include Tris, Hepes, triethanolamine, histidine, or any others known to the art to have the desired effect.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors; platelet-growth factor; transforming growth factors (TGFs) such as TGF-α and TGF-β; insulin-like growth factor-I and -II; erythropoietin (EPO); osteoinductive factors; interferons such as interferon-α, -β, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-2, IL-3, IL-4, IL-5, IL-6, IL-7, IL-8, IL-9, IL-11, IL-12; and other polypeptide factors including LIF and kit ligand (KL). As used herein, the term cytokine includes proteins from natural sources or from recombinant cell culture and biologically active equivalents of the native sequence cytokines.

The term, "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gamma1I and calicheamicin phiI1, see, Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antiobiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (Adriamycin™) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK®; razoxane; rhizoxin; sizofuran; spirogermanium; tenuazonic acid; triaziquone; 2, 2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTER®, Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine (Navelbine™); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included in this definition are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); aromatase inhibitors that inhibit the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™) and anastrozole (Arimidex™); and anti-androgens such as flutamide, nilutamide, bicalutamide, leuprolide, and goserelin; and pharmaceutically acceptable salts, acids or derivatives of any of the above.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al., (WB Saunders: Philadelphia, 1995), especially p. 13.

"Biologically active" or "biological activity" for the purposes herein means (a) having the ability to induce or stimulate apoptosis in at least one type of mammalian cancer cell or virally-infected cell in vivo or ex vivo, either alone as a single agent or in combination with a chemotherapeutic agent (b) capable of raising an antibody, i.e., immunogenic; (c) capable of binding and/or stimulating a receptor for Apo2L/TRAIL (such receptors may include the DR4 receptor, DR5 receptor, OPG, DcR1 receptor, and DcR2 receptor); or (d) retaining the activity of a native or naturally-occurring Apo2L/TRAIL polypeptide. Assays for determining biological activity of the Apo2L/TRAIL can be conducted using methods known in the art, such as DNA fragmentation (see, e.g., Marsters et al., Curr. Biology, 6: 1669 (1996)), caspase inactivation, DR4 binding, DR5 binding (see, e.g., WO 98/51793, published Nov. 19, 1998), DcR1 binding (see, e.g., WO 98/58062, published Dec. 23, 1998), DcR2 binding (see, e.g., WO 99/10484, published Mar. 4, 1999) as well as the assays described in PCT Publication Nos. WO97/01633, WO97/25428, WO 01/00832, and WO 01/22987.

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays (such as Alamar blue assays or MTT assays), FACS analysis, caspase activation, DNA fragmentation (see, for example, Nicoletti et al., *J. Immunol. Methods,* 139:271-279 (1991), and poly-ADP ribose polymerase, "PARP", cleavage assays known in the art.

As used herein, the term "disorder" in general refers to any condition that would benefit from treatment with the compositions described herein, including any disease or disorder that can be treated by effective amounts of polypeptides such as Apo2L/TRAIL. This includes chronic and acute disorders, as well as those pathological conditions which predispose the mammal to the disorder in question. Non-limiting examples of disorders to be treated herein include benign and malignant cancers; inflammatory, angiogenic, and immunologic disorders, autoimmune disorders, arthritis (including rheumatoid arthritis), multiple sclerosis, and HIV/AIDS.

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, gastrointestinal cancer, renal cancer, ovarian cancer, liver cancer, lymphoblastic leukemia, lymphocytic leukemia, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer. Optionally, the cancer cells express DR4 and/or DR5 receptor(s).

The terms "treating", "treatment" and "therapy" as used herein refer to curative therapy, prophylactic therapy, and preventative therapy. Consecutive treatment or administration refers to treatment on at least a daily basis without interruption in treatment by one or more days. Intermittent treatment or administration, or treatment or administration in an intermittent fashion, refers to treatment that is not consecutive, but rather cyclic in nature.

The term "mammal" as used herein refers to any mammal classified as a mammal, including humans, cows, horses, dogs and cats. In a preferred embodiment of the invention, the mammal is a human.

B. Exemplary Methods and Materials for Carrying Out the Invention

The present invention provides various formulations, and methods for making such formulations, of Apo2L/TRAIL. Various formulation excipients can enhance solubility of Apo2L/TRAIL in formulations, for instance, which are acceptable for pharmaceutical uses and/or enhance stability of the Apo2L/TRAIL protein in a form (e.g., trimer form) which has biological activity. For example, Applicants have found that the presence of various excipients (for instance, arginine salts) in such formulations can markedly increase the solubility and stability of Apo2L/TRAIL.

The unexpected finding of the readily reversible crystallization of Apo2L/TRAIL further provides basis for purification methods and stable formulations of Apo2L/TRAIL. In particular, forming crystals and subsequently drying the material by various methods (including lyophilization) may provide long term stability of bulk preparations of the protein. Further, lyophilized crystal compositions are expected to retain stability through a range of temperatures. Applicants have found that a preferred water content of the dried crystals (useful for optimizing trimer stability) is at least about 5% water, and preferably about 5% to about 10% water. Particularly, Applicants found that for storage at temperatures greater than 30° C., reducing the water content of the dried crystals to below about 5% water may adversely affect the storage-stability of the Apo2L/TRAIL protein crystals. Addition of one or more excipients, such as sucrose, trehalose, arginine, or Captisol™ to the protein crystal compositions may impove or enhance storage-stability of the protein crystals.

Dried crystals can also be employed in suspension formulations suitable for, e.g., subcutaneous or intramuscular administration. As described in the Examples, sodium salts, particularly sodium sulfate ($Na_2SO_4$), provided ready and reversible crystallization, with retention of biological activity upon re-dissolution of the protein. The protein crystals then readily re-dissolved in water or an aqueous buffer, e.g. a carboxylic acid salt of an amino acid, or can be suspended in non-aqueous media without loss in physicochemical properties that can be important for the protein's biological activity.

Generally, the formulations are prepared using Apo2L/TRAIL polypeptides (proteins), at the desired degree of purity, and various excipients or components, described below.

Production of Apo2L/TRAIL

The description below relates to methods of producing Apo2L/TRAIL by culturing host cells transformed or transfected with a vector containing Apo2L/TRAIL encoding nucleic acid and recovering the polypeptide from the cell culture.

The DNA encoding Apo2L/TRAIL may be obtained from any cDNA library prepared from tissue believed to possess the Apo2L/TRAIL mRNA and to express it at a detectable level. Accordingly, human Apo2L/TRAIL DNA can be conveniently obtained from a cDNA library prepared from human tissues, such as the bacteriophage library of human placental cDNA as described in PCT Publication WO97/25428. The Apo2L/TRAIL-encoding gene may also be obtained from a genomic library or by oligonucleotide synthesis.

Libraries can be screened with probes (such as antibodies to the Apo2L/TRAIL or oligonucleotides of at least about 20-80 bases) designed to identify the gene of interest or the protein encoded by it. Screening the cDNA or genomic library with the selected probe may be conducted using standard procedures (Sambrook et al., *Molecular Cloning: A Laboratory Manual*; New York: Cold Spring Harbor Laboratory Press, 1989). An alternative means to isolate the gene encoding Apo2L/TRAIL is to use PCR methodology (Sambrook et al., supra; Dieffenbach et al., *PCR Primer: A Laboratory Manual*, Cold Spring Harbor Laboratory Press, 1995).

Amino acid sequence fragments or variants of Apo2L/TRAIL can be prepared by introducing appropriate nucleotide changes into the Apo2L/TRAIL DNA, or by synthesis of the desired Apo2L/TRAIL polypeptide. Such fragments or variants represent insertions, substitutions, and/or deletions of residues within or at one or both of the ends of the intracellular region, the transmembrane region, or the extracellular region, or of the amino acid sequence shown for the full-length Apo2L/TRAIL in FIG. 1 (SEQ ID NO:1). Any combination of insertion, substitution, and/or deletion can be made to arrive at the final construct, provided that the final construct possesses, for instance, a desired biological activity or apoptotic activity as defined herein. In a preferred embodiment, the fragments or variants have at least about 80% amino acid sequence identity, more preferably, at least about 90% sequence identity, and even more preferably, at least 95%, 96%, 97%, 98% or 99% sequence identity with, for example, the sequences identified herein for the intracellular, transmembrane, or extracellular domains of Apo2L/TRAIL, or the full-length sequence for Apo-2L/TRAIL. The amino acid changes also may alter post-translational processes of the Apo-2L/TRAIL, such as changing the number or position of glycosylation sites or altering the membrane anchoring characteristics.

Variations in the Apo2L/TRAIL sequence as described above can be made using any of the techniques and guidelines for conservative and non-conservative mutations set forth in U.S. Pat. No. 5,364,934. These include oligonucleotide-mediated (site-directed) mutagenesis, alanine scanning, and PCR mutagenesis.

Scanning amino acid analysis can be employed to identify one or more amino acids along a contiguous sequence. Among the preferred scanning amino acids are relatively small, neutral amino acids. Such amino acids include alanine, glycine, serine and cysteine. Alanine is typically a preferred scanning amino acid among this group because it eliminates the side-chain beyond the beta-carbon and is less likely to alter the main-chain conformation of the variant. (Cunningham et al., *Science* 1989, 244:1081). Alanine is also typically preferred because it is the most common amino acid. Further, it is frequently found in both buried and exposed positions (Creighton, *The Proteins*, (W.H. Freeman & Co., NY); Chothia, J. Mol. Biol. 1976, 150:1).

Particular Apo2L/TRAIL variants of the present invention include those Apo2L/TRAIL polypeptides which include one or more of the recited alanine substitutions provided in TABLE I of published PCT application WO 01/00832. Such Apo2L/TRAIL variants will typically comprise a non-naturally occurring amino acid sequence which differs from a native Apo2L/TRAIL amino acid sequence (such as provided in FIG. 1; SEQ ID NO:1, for a full length or mature form of Apo2L/TRAIL or an extracellular domain sequence thereof) in at least one or more amino acids. Optionally, the one or more amino acids which differ in the Apo2L/TRAIL variant as compared to a native Apo2L/TRAIL will comprise amino acid substitution(s) such as those indicated in Table I of WO 01/00832. Apo2L/TRAIL variants of the invention include soluble Apo2L/TRAIL variants comprising residues 91-281, 92-281, 95-281 or 114-281 of FIG. 1 (SEQ ID NO:1) and having one or more amino acid substitutions. Preferred Apo2L/TRAIL variants will include those variants comprising residues 91-281, 92-281, 95-281 or 114-281 of FIG. 1 (SEQ ID NO:1) and having one or more amino acid substitutions which enhance biological activity, such as receptor binding. A particularly preferred variant comprises residues 114-281 of FIG. 1 (SEQ ID NO:1). In a specific embodiment, Apo-2L/TRAIL consists of residues 114-281 of FIG. 1 (SEQ ID NO:1).

As described in WO 01/00832 published Jan. 4, 2001, the x-ray crystal structure of the extracellular domain of Apo2L/TRAIL was identified, and alanine-scanning mutagenesis was performed to provide the mapping of its receptor contact regions. The structure obtained for Apo2L/TRAIL revealed a homotrimeric protein which contains a novel divalent metal ion (zinc) binding site that coordinates the interaction of the Apo2L/TRAIL trimer molecule's three subunits. Like other members of the TNF family, Apo2L/TRAIL appears to comprise a compact trimer formed of three jelly roll monomers which bury approximately 5100 Angstrom$^2$ (1700 Angstrom$^2$ per monomer) to form the globular trimer. The position of the core beta-strands was well conserved compared to the other structurally characterized members of the TNF family, TNF-alpha, TNF-beta, and CD40L when compared to the core strands of TNF-alpha or TNF-beta.

Variations in the Apo2L/TRAIL sequence also included within the scope of the invention relate to amino-terminal derivatives or modified forms. Such Apo2L/TRAIL sequences may include any of the Apo2L/TRAIL polypeptides described herein having a methionine or modified methionine (such as formyl methionyl or other blocked methionyl species) at the N-terminus of the polypeptide sequence.

The nucleic acid (e.g., cDNA or genomic DNA) encoding native or variant Apo2L/TRAIL may be inserted into a replicable vector for further cloning (amplification of the DNA) or for expression. Various vectors are publicly available. The vector components generally include, but are not limited to, one or more of the following: a signal sequence, an origin of replication, one or more marker genes, an enhancer element, a promoter, and a transcription termination sequence, each of which is described below. Optional signal sequences, origins of replication, marker genes, enhancer elements and transcription terminator sequences that may be employed are known in the art and described in further detail in PCT Publication WO97/25428.

Expression and cloning vectors usually contain a promoter that is recognized by the host organism and is operably linked to the Apo2L/TRAIL nucleic acid sequence. Promoters are untranslated sequences located upstream (5') to the start codon of a structural gene (generally within about 100 to 1000 bp) that control the transcription and translation of a particular nucleic acid sequence, such as the Apo2L/TRAIL nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to Apo2L/TRAIL encoding DNA by removing the promoter from the source DNA by restriction enzyme digestion and inserting the isolated promoter sequence into the vector. Both the native Apo2L/TRAIL promoter sequence and many heterologous promoters may be used to direct amplification and/or expression of the Apo2L/TRAIL DNA.

Promoters suitable for use with prokaryotic and eukaryotic hosts are known in the art, and are described in further detail in PCT Publication No. WO97/25428.

Preferred methods for the production of soluble Apo2L/TRAIL in *E. coli* employ an inducible promoter for the regulation of product expression. The use of a controllable, inducible promoter allows for culture growth to the desirable cell density before induction of product expression and accumulation of significant amounts of product which may not be well tolerated by the host.

Three inducible promoter systems (T7 polymerase, trp and alkaline phosphatase (AP)) have been evaluated by Applicants for the expression of Apo2L/TRAIL (amino acids 114-281). The use of each of these three promoters resulted in significant amounts of soluble, biologically active Apo2L/TRAIL trimer being recovered from the harvested cell paste. The AP promoter is preferred among these three inducible promoter systems tested because of tighter promoter control and the higher cell density and titers reached in harvested cell paste.

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures can be used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced using standard techniques known in the art. (See, e.g., Messing et al., Nucleic Acids Res. 1981, 9:309; Maxam et al., Methods in Enzymology 1980, 65:499).

Expression vectors that provide for the transient expression in mammalian cells of DNA encoding Apo2L/TRAIL may be employed. In general, transient expression involves the use of an expression vector that is able to replicate efficiently in a host cell, such that the host cell accumulates many copies of the expression vector and, in turn, synthesizes high levels of a desired polypeptide encoded by the expression vector (Sambrook et al., supra). Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of Apo2L/TRAIL that are biologically active Apo2L/TRAIL.

Other methods, vectors, and host cells suitable for adaptation to the synthesis of Apo2L/TRAIL in recombinant vertebrate cell culture are described in Gething et al., Nature 1981, 293:620-625; Mantei et al., Nature 1979, 281:40-46; EP 117,060; and EP 117,058.

Suitable host cells for cloning or expressing the DNA in the vectors herein include prokaryote, yeast, or higher eukaryote cells. Suitable prokaryotes for this purpose include but are not limited to eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989),

*Pseudomonas* such as *P. aeruginosa*, and *Streptomyces*. Preferably, the host cell should secrete minimal amounts of proteolytic enzymes.

*E. coli* is the preferred host cell for use in the present invention. *E. coli* is particularly well suited for the expression of Apo2L/TRAIL (comprising amino acids 114-281 of FIG. 1), a polypeptide of under 20 kd in size with no glycosylation requirement. As a production host, *E. coli* can be cultured to relatively high cell density and is capable of producing relatively high levels of heterologous proteins.

In addition to prokaryotes, eukaryotic microbes such as filamentous fungi or yeast are suitable cloning or expression hosts for Apo2L/TRAIL-encoding vectors. Suitable host cells for the expression of glycosylated Apo2L/TRAIL are derived from multicellular organisms. Examples of all such host cells, including CHO cells, are described further in PCT Publication No. WO97/25428.

Host cells are transfected and preferably transformed with the above-described expression or cloning vectors for Apo2L/TRAIL production and cultured in nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described (Shaw et al., Gene 1983, 23:315 and PCT Publication No. WO 89/05859). In addition, plants may be transfected using ultrasound treatment, PCT Publication No. WO 91/00358 published 10 Jan. 1991.

For mammalian cells without such cell walls, the calcium phosphate precipitation method (Graham and van der Eb, Virology 1978, 52:456-457) may be employed. General aspects of mammalian cell host system transformations have been described in U.S. Pat. No. 4,399,216. Transformations into yeast are typically carried out according to the method of Van Solingen et al., J. Bact. 1977, 130:946 and Hsiao et al. Proc. Natl. Acad. Sci. USA 1979, 76:3829. However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al. Methods in Enzymology 1990, 185:527-537 and Mansour et al. Nature 1988, 336:348-352.

Prokaryotic cells used to produce Apo2L/TRAIL may be cultured in suitable culture media as described generally in Sambrook et al., supra. Particular forms of culture media that may be employed for culturing *E. coli* are described further in PCT application WO 01/00832. Mammalian host cells used to produce Apo2L/TRAIL may be cultured in a variety of culture media.

Examples of commercially available culture media include Ham's F10 (Sigma), Minimal Essential Medium ("MEM", Sigma), RPMI-1640 (Sigma), and Dulbecco's Modified Eagle's Medium ("DMEM", Sigma). Any such media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: A Practical Approach*, M. Butler, ed. (IRL Press, 1991).

Expression of the Apo2L/TRAIL may be measured in a sample directly, for example, by conventional Southern blotting, Northern blotting to quantitate the transcription of mRNA (Thomas, Proc. Natl. Acad. Sci. USA 1980, 77:5201-5205), dot blotting (DNA analysis), or in situ hybridization, using an appropriately labeled probe, based on the sequences provided herein. Various labels may be employed, most commonly radioisotopes, and particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionucleotides, fluorescers or enzymes. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like.

Antibodies useful for immunohistochemical staining and/or assay of sample fluids may be either monoclonal or polyclonal, and may be prepared in any mammal. Conveniently, the antibodies may be prepared against a native Apo2L/TRAIL polypeptide or against a synthetic peptide based on the DNA sequences provided herein or against exogenous sequence fused to Apo2L/TRAIL DNA and encoding a specific antibody epitope.

Apo2L/TRAIL preferably is recovered from the culture medium as a secreted polypeptide, although it also may be recovered from host cell lysates when directly produced without a secretory signal. If the Apo2L/TRAIL is membrane-bound, it can be released from the membrane using a suitable detergent solution (e.g., Triton-X 100) or its extracellular region may be released by enzymatic cleavage.

When Apo2L/TRAIL is produced in a recombinant cell other than one of human origin, the Apo2L/TRAIL is free of proteins or polypeptides of human origin. However, it is usually necessary to recover or purify Apo2L/TRAIL from recombinant cell proteins or polypeptides to obtain preparations that are substantially homogeneous as to Apo2L/TRAIL. As a first step, the culture medium or lysate may be centrifuged to remove particulate cell debris. Apo2L/TRAIL thereafter is purified from contaminant soluble proteins and polypeptides, with the following procedures being exemplary of suitable purification procedures: by fractionation on an ion-exchange column such as SP-sepharose or CM-sepharose; hydroxyapatite; hydrophobic interaction chromatography; ethanol precipitation; chromatofocusing; ammonium sulfate precipitation; gel filtration using, for example, Sephadex G-75; and diafiltration.

The Apo2L/TRAIL can be isolated by affinity chromatography. Apo2L/TRAIL fragments or variants in which residues have been deleted, inserted, or substituted are recovered in the same fashion as native Apo2L/TRAIL, taking account of any substantial changes in properties occasioned by the variation. For example, preparation of an Apo2L/TRAIL fusion with another protein or polypeptide, e.g., a bacterial or viral antigen, facilitates purification; an immunoaffinity column-containing antibody to the antigen can be used to adsorb the fusion polypeptide.

A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native Apo2L/TRAIL may require modification to account for changes in the character of Apo2L/TRAIL or its variants upon expression in recombinant cell culture.

During any such purification steps, it may be desirable to expose the recovered Apo2L/TRAIL to a divalent metal ion-containing solution or to purification material (such as a chromatography medium or support) containing one or more divalent metal ions. The divalent metal ions and/or reducing agent may be used during recovery or purification of the Apo2L/TRAIL. Optionally, both divalent metal ions and reducing agent, such as DTT or BME, may be used during recovery or purification of the Apo2L/TRAIL. It is believed that use of divalent metal ions during recovery or purification will assist in providing stability of Apo2L/TRAIL trimer or preserve Apo2L/TRAIL trimer formed during the cell culturing step.

Preparation of Formulations

In the preparation of the formulations herein, it is noted that the recommended quality or "grade" of the components employed will depend on the ultimate use of the formulation. For therapeutic uses, it is preferred that the component(s) are of an allowable grade (such as "GRAS") as an additive to pharmaceutical products.

In certain embodiments, there are provided compositions comprising Apo2L/TRAIL and one or more excipients which provide sufficient ionic strength to enhance solubility and/or stability of the Apo2L/TRAIL, wherein the composition has a pH of 6 (or about 6) to 9 (or about 9). The Apo2L/TRAIL protein may be prepared by any suitable method to achieve the desired purity of the protein, for example, according to the above methods. In preferred embodiments, the Apo2L/TRAIL protein comprises amino acids 114-281 of FIG. 1, and more preferably, the Apo2L/TRAIL protein is recombinantly expressed in *E. coli* host cells. The concentration of the Apo2L/TRAIL protein in the formulation may vary depending, for instance, on the intended use of the formulation. Those skilled in the art can determine without undue experimentation the desired concentration of the Apo2L/TRAIL protein. For therapeutic uses, the concentration of the Apo2L/TRAIL protein in the formulation is optionally about 0.1 to about 100 mg/ml, about 1 to about 20 mg/ml, about 10 to about 20 mg/ml, or about 20 mg/ml.

The one or more excipients in the formulations which provide sufficient ionic strength to enhance solubility and/or stability of the Apo2L/TRAIL is optionally a polyionic organic or inorganic acid, aspartate, sodium sulfate, sodium succinate, sodium acetate, sodium chloride, Captisol™, Tris, arginine salt or other amino acids, sugars and polyols such as trehalose and sucrose. Preferably the one or more excipients in the formulations which provide sufficient ionic strength is a salt. Salts which may be employed include but are not limited to sodium salts and arginine salts. The type of salt employed and the concentration of the salt is preferably such that the formulation has a relatively high ionic strength which allows the Apo2L/TRAIL in the formulation to be stable (i.e., reduce precipitation and enhance trimer content) and/or which allows the soluble protein concentration to exceed 2 mg/ml, more preferably, exceed 5 mg/ml, even more preferably exceed 10 mg/ml, and most preferably to achieve a concentration of at least about 20 mg/ml. Optionally, the salt is present in the formulation at a concentration of about 20 mM to about 0.5 M. In more preferred embodiments, the salt is an arginine salt or sodium sulfate. Optionally, the arginine salt may comprise arginine citrate, arginine tartrate, arginine malate, arginine succinate, arginine phosphate, and arginine sulfate. More preferably, the arginine salt is present in a concentration of about 0.2 M to about 0.5 M. It is noted that while arginine tartrate is useful as an excipient in the formulations described herein, the use of tartaric acid as a vehicle at higher concentrations (such as hundreds of mM) may not be desirable for parenteral administration or human clinical applications. Applicants have observed in an in vivo animal study that vehicle concentrations of 0.5M arginine neutralized with 0.25M tartrate administered intravenously at greater than 5 ml/kg/hr can have a deleterious effect on renal tissue. Accordingly, there may be an upper threshold concentration of tartaric acid beyond which one skilled in the art would not select for clinical, therapeutic uses.

If relatively lower concentrations of Apo2L/TRAIL protein are desired in the formulation, for instance, less than about 5 mg/ml, or less than about 2 mg/ml, or about 0.1 to about 2 mg/ml, the excipient providing stability to the formulation may be a sugar, such as trehalose, sucrose, glucose, lactitol, or lactose. Optionally, the sugar may be employed in the formulations at a concentration of about 1% to about 8%. The excipient may also be an arginine salt, as described above.

The composition preferably has a pH of 6 (or about 6) to 9 (or about 9), more preferably about 6.5 to about 8.5, and even more preferably about 7 to about 7.5. In a preferred aspect of this embodiment, the composition will further comprise a buffer to maintain the pH of the composition at least about 6 to about 8. Examples of buffers which may be employed include but are not limited to Tris, HEPES, and histidine. When employing Tris, the pH may optionally be adjusted to about 7 to 8.5. When employing Hepes or histidine, the pH may optionally be adjusted to about 6.5 to 7. Optionally, the buffer is employed at a concentration of about 5 mM to about 50 mM in the formulation, and preferably at a concentration of about 10 mM to about 20 mM.

Particularly for liquid formulations (or reconstituted lyophilized formulations), it may be desirable to include one or more surfactants in the composition. Such surfactants may, for instance, comprise a non-ionic surfactant like TWEEN™ or PLURONICS™ (e.g., polysorbate or poloxamer). Preferably, the surfactant comprises polysorbate 20 ("Tween 20"). The surfactant will optionally be employed at a concentration of about 0.005% to about 0.2%.

Preferred formulations are those in which the excipient(s) provide for optimized Apo2L/TRAIL trimer content and minimize the amount of Apo2L/TRAIL dimer formation (or aggregate formation) or changes in charge distribution. Optionally, the formulation contains no more than 5% Apo2L/TRAIL aggregates, no more than 10% Apo2L/TRAIL disulfide linked dimer (of the total amount of Apo2L/TRAIL protein in the formulation), and/or no more than 10% change in the initial charge distribution.

In preferred embodiments, the present invention provides compositions comprising about 0.1 mg/ml to about 20 mg/ml of Apo2L/TRAIL and an arginine salt, wherein the composition has a pH of about 6.5 to about 8.5 (optionally, 6.8 to 7.5). Optionally, the compositions further comprise a buffer such as Tris and/or a surfactant such as polysorbate 20. Preferably, the Apo2L/TRAIL protein does not include (i.e., is not linked or fused to) any epitope tag molecule(s) or leucine zipper molecule(s).

In even more preferred embodiments, the present invention provides compositions comprising about 2 to about 20 mg/ml of Apo2L/TRAIL, about 0.4 to about 0.5M arginine salt, and buffer, wherein the composition has a pH of about 6.5 to about 7.5.

Optionally, a divalent metal ion may be included in the formulations. The divalent metal ion may be a zinc molecule, such as zinc sulfate, zinc chloride, or zinc acetate. The divalent metal ion can optionally be included in the formulation at a concentration of about 50 micromolar to about 400 micromolar.

The formulations of the present invention may include, in addition to Apo2L/TRAIL and those components described above, further various other excipients or components. Optionally, the formulation may contain, for parenteral administration, a pharmaceutically or parenterally acceptable carrier, i.e., one that is non-toxic to recipients at the dosages and concentrations employed and is compatible with other ingredients of the formulation. Optionally, the carrier is a parenteral carrier, such as a solution that is isotonic with the blood of the recipient. Examples of such carrier vehicles include water, saline or a buffered solution such as phosphate-buffered saline (PBS), Ringer's solution, and dextrose solution. Various optional pharmaceutically acceptable carriers, excipients, or stabilizers are described further in *Remington's Pharmaceutical Sciences*, 16th edition, Osol, A. ed. (1980).

The formulations herein also may contain one or more preservatives. Examples include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols, alkyl parabens such as methyl or propyl paraben, and m-cresol. Antioxidants include ascorbic acid and methionine; preservatives (such as octadecyldimethylbenzyl ammonium chloride; hexamethonium chloride; benzalkonium chloride, benzethonium chloride; butyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; sugars such as sucrose, mannitol, trehalose or sorbitol; or polyethylene glycol (PEG).

Additional examples of such carriers include lecithin, serum proteins, such as human serum albumin, buffer substances such as glycine, sorbic acid, potassium sorbate, partial glyceride mixtures of saturated vegetable fatty acids, water, salts, or electrolytes such as protamine sulfate, sodium chloride, polyvinyl pyrrolidone, and cellulose-based substances. Carriers for gel-based forms include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. Conventional depot forms include, for example, microcapsules, nano-capsules, liposomes, plasters, inhalation forms, nose sprays, and sustained-release preparations.

The compositions of the invention may comprise liquid formulations (liquid solutions or liquid suspensions), and lyophilized formulations, as well as suspension formulations in which the Apo2L/TRAIL protein is in the form of crystals or amorphous precipitate.

The final formulation, if a liquid, is preferably stored frozen at $\leq 20°$ C. Alternatively, the formulation can be lyophilized and provided as a powder for reconstitution with water for injection that optionally may be stored at 2-30° C.

The formulation to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

The composition ordinarily will be stored in single unit or multi-dose containers, for example, sealed ampules or vials, as an aqueous solution or as a lyophilized formulation for reconstitution. The containers may any available containers in the art and filled using conventional methods. Optionally, the formulation may be included in an injection pen device (or a cartridge which fits into a pen device), such as those available in the art (see, e.g., U.S. Pat. No. 5,370,629), which are suitable for therapeutic delivery of the formulation. As an example of a lyophilized formulation, 10 mL vials are filled with 5.5 mL of sterile-filtered 2% (w/v) aqueous Apo2L/TRAIL solution, and the resulting mixture is lyophilized. An injection solution can be prepared by reconstituting the lyophilized Apo2L/TRAIL formulation using, for example, Water-for-Injection.

In further more particular embodiments of the formulations, there are provided compositions which include Apo2L/TRAIL crystals. For instance, the composition may comprise a suspension formulation comprising Apo2L/TRAIL crystals. Applicants surprisingly found that the solid state of Apo2L/TRAIL protein at 5° C. is crystalline at moderate to low ionic conditions, unlike many other proteins known in the art that are soluble or form amorphous precipitates under similar conditions. Further, it was found that the solid state of the Apo2L/TRAIL crystals reversibly solubilizes when brought to ambient temperature (i.e., room temperature) without a loss in protein biological activity or adverse effect on the biochemical properties of the protein. This observation was quite different from the denaturation or irreversible precipitation observed for other proteins known in the art.

Optionally, the Apo2L/TRAIL crystals are prepared by cooling a super-saturated solution of Apo-2L/TRAIL protein from about 20 to about 30° C. to below about 15° C., preferably about 2 to 8° C., and more preferably, below about 2-8° C. Crystallization can be carried out in batch or semi-batch mode at a large range of scale, from a few milliliters to hundreds of liters of solution. The crystallization rate can be controlled by programmed cooling and agitation. The equipment may include, but is not limited to, agitated or static tanks with surface and/or internal temperature control. Internal baffles and draft tubes may also be used to enhance mixing in agitated tanks. Crystal nucleation can also be controlled by seeding [Moore, AIChE Practical Engineering Perspectives, Distillation and Other Industrial Separations, pp. 239-245]. The degree of super-saturation, salt composition, cooling rate, agitation rate, and seeding can affect crystal formation rate, crystal size distribution, and crystal yield.

The Apo2L/TRAIL crystal slurry may be washed to remove the salts. Optionally, the crystal slurry may be washed with water. Alternatively, the crystal slurry may be equilibrated to a low ionic strength. Subsequently, the material may be dried for storage or preparation for parenteral formulations. The crystal drying methods may include but are not limited to static vacuum drying, vacuum drying with vibration, rotation, or agitation motion facilitated by dry air/N2 flow, lyophilization, spray drying and fluidized bed drying.

Applicants have found that it may be desirable to achieve a water content of at least about 5%, and preferably about 5% to about 10% in the dried crystals. It will be within the ordinary skill in the art for the artisan to control the water content of the crystal composition using known techniques, such as by stopping the drying (e.g., lyophilization) process(s) at designated time points or by drying the crystal compositon completely (or until minimal water is present) and then adding back controlled amounts of water to achieve the desired amount of re-hydration to the protein crystals.

Optionally, to prepare the crystals, the solution of Apo-2L/TRAIL protein contains sodium sulphate or sodium chloride. Optionally, the salt concentration is about 25 mM to about 150 mM and optionally the pH is about 6 to about 9 (preferably, pH of about 6.5 to about 8.5).

Optionally, other excipients, such as sucrose, trehalose, glucose, lactitol, lactose, arginine, or Captisol™, may be included in the crystal preparation. Optionally, the molar ratio of such excipient to Apo2L/TRAIL trimer is about 1 millimole to about 300 moles excipient to moles of Apo2L/TRAIL trimer. Optionally, the sugar may be employed in the crystal preparation at a concentration of about 0.001% (w/w) to about 65% (w/w). Such excipients may optionally be added to the wet crystal slurry (prior to drying) so that the excipient(s) can diffuse into the crystalline composition.

The Apo2L/TRAIL crystals can be reconstituted to a liquid formulation and sterilized for parenteral injection. Alternatively, the dried crystals can be suspended in a high viscosity biocompatible medium for subcutaneous or intramuscular administration. The suspending medium may be aqueous or non-aqueous. Examples of aqueous suspensions include cellulose-based systems such as carboxymethyl cellulose, hydroxyethylcellulose, or polymer-based systems like polylactic acid-glycolic acid (PGLA). An example of non-aqueous medium is sucrose acetate isobutyrate (SAIB) predissolved in solvents such as ethanol, propylene carbonate, or N-methylpyrrolidone. A suspension of uniform size distribution can be prepared by homogenizing the dried crystals in the viscous medium using, by way of example, a probe homogenizer or a microfluidizer.

Methods of Use and Other Applications

In one embodiment of the invention, there is provided an improved method for purifying and storing Apo2L/TRAIL protein. More particularly, the methods of purification employ crystallization of Apo2L/TRAIL and the crystals can be dried for storage. The methods provide an effective, efficient, and cost saving alternative to, for instance, purification protocols requiring multiple column purifications. Drying the crystalline material can also provide a relatively low volume, effective way of bulk storage which avoids freezing the purified material in bulk containers and thawing the frozen bulk material.

In the methods, an Apo2L/TRAIL preparation, such as a cell paste containing recombinantly expressed Apo2L/TRAIL protein, is provided. Optionally, though not required, the cell paste may be processed (for instance, may be exposed to one or more reducing agents such as DTT or BME) or partially purified using any suitable methods known in the art, such as cation exchange chromatography methods. Cation exchange chromatography materials may optionally be SP-Sepharose, CM-Sepharose, or Macro-prep ceramic HS resin. Applicants have found that addition of polyethylene glycol to the pool being applied to such chromatography columns may assist in increasing yield of crystalline protein. Various polyethylene glycols are commercially available (such as from Nektar Corporation). Polyethelyene glycols of various molecular weights may be employed (such as from 100 to 10,000), preferably a PEG of approximately 400 D is employed at a concentration of about 5%. It is within the skill in the art to determine optimal PEG molecular weights and concentrations to increase protein crystal yield.

The processed or partially purified Apo2L/TRAIL in the preparation can be crystallized from, for instance, a super-saturated solution by decreasing temperature and agitation using the methods described herein. The crystals may then be collected, and washed with buffer (or water) (preferably a cold buffer at a temperature of about 2 to 8° C.). The washed crystals can be re-suspended or re-dissolved at ambient temperature.

Re-solubilized Apo2L/TRAIL can be further purified by hydrophobic interaction chromatography, recrystallized, washed and stored as wet crystalline bulk material. Alternatively, the hydrophobic interaction or other chromatography step may be omitted in favor of simply recrystallizing. The wet crystalline bulk material can be stored at −20° C. or dried for storage at ambient temperature (room temperature) or at 2-8° C. Preferably, the dried crystalline material is re-solubilized in an arginine succinate-containing formulation described above. Optionally, such a formulation can be sterile filtered and/or filled in individual dosage vials, and lyophilized for later reconstitution or suspension. Optionally, the dried crystalline formulation can be filled as a powder in vials and made into a solution or suspension. As described above, it may be desirable to achieve a water content of about 5% to about 10% in the dried Apo2L/TRAIL crystals.

The Apo2L/TRAIL formulations described herein can be employed in a variety of therapeutic and non-therapeutic applications. Among these applications are methods of treating disorders, such as cancer, immune related conditions, or viral conditions. Such therapeutic and non-therapeutic applications are further described, for instance, in WO97/25428, WO97/01633, and WO 01/22987.

In the methods of the invention for treating a disorder using a formulation disclosed herein, the formulation of Apo2L/TRAIL can be directly administered to the mammal by any suitable technique, including infusion or injection. The specific route of administration will depend, e.g., on the medical history of the patient, including any perceived or anticipated side effects using Apo2L/TRAIL and the particular disorder to be corrected. Examples of parenteral administration include subcutaneous, intramuscular, intravenous, intraarterial, and intraperitoneal administration of the composition. The formulations are preferably administered as repeated intravenous (i.v.), subcutaneous (s.c.), intramuscular (i.m.) injections or infusions, intracranial infusions or as aerosol formulations suitable for intranasal or intrapulmonary delivery (for intrapulmonary delivery see, e.g., EP 257,956).

It is noted that osmotic pressure of injections may be important in subcutaneous and intramuscular injection. Injectable solutions, when hypotonic or hypertonic, may cause pain to a patient upon infusion. Usually, for the therapeutic, injectable formulations herein, it is preferred that the relative osmolarity of the injectable solution be about 300 mosm to about 600 mosm.

Apo2L/TRAIL can also be administered in the form of sustained-release preparations. Suitable examples of sustained-release preparations include semipermeable matrices of solid hydrophobic polymers containing the protein, which matrices are in the form of shaped articles, e.g., films, or microcapsules. Examples of sustained-release matrices include cellulose derivatives (e.g., carboxymethylcellulose), sucrose-acetate isobutyrate (SABER™) in non-aqueous media, polyesters, hydrogels (e.g., poly(2-hydroxyethylmethacrylate) (Langer et al., *J. Biomed. Mater. Res.* 1981, 15: 167-277; Langer, Chem. Tech. 1982, 12: 98-105 or poly (vinylalcohol)), polylactides (U.S. Pat. No. 3,773,919, EP 58,481), copolymers of L-glutamic acid and gamma ethyl-L-glutamate (Sidman et al., Biopolymers 1983, 22: 547-556), non-degradable ethylene-vinyl acetate (Langer et al., supra), degradable lactic acid-glycolic acid copolymers such as the Lupron Depot (injectable microspheres composed of lactic acid-glycolic acid copolymer and leuprolide acetate), and poly-D-(-)-3-hydroxybutyric acid (EP 133,988). One optional method of delivery for systemic-acting drugs involves administration by continuous infusion (using, e.g., slow-release devices or minipumps such as osmotic pumps or skin patches), or by injection (using, e.g., intravenous or subcutaneous means, including single-bolus administration).

The composition to be used in the therapy will be formulated and dosed in a fashion consistent with good medical practice, taking into account the clinical condition of the individual patient, the site of delivery of the composition, the method of administration, the scheduling of administration, and other factors known to practitioners. The "effective amounts" of each component for purposes herein are thus determined by such considerations and are amounts that result in bioavailability of the Apo2L/TRAIL or other drugs to the mammal.

As a general proposition, the total pharmaceutically effective amount of the Apo2L/TRAIL polypeptides administered will be in the range of from about 1 mg/kg/day to about 20 mg/kg/day based on kg of patient body weight although, as noted above, this will be subject to therapeutic discretion.

Although injection is preferred, an infusion device may also be employed for continuous infusions. An intravenous bag solution may also be employed.

It is contemplated that yet additional therapies may be employed in the methods. The one or more other therapies may include but are not limited to, administration of radiation therapy, cytokine(s), growth inhibitory agent(s), chemotherapeutic agent(s), cytotoxic agent(s), tyrosine kinase inhibitors, ras farnesyl transferase inhibitors, angiogenesis inhibitors, and cyclin-dependent kinase inhibitors which are known in the art and defined further with particularity in Section I above. In addition, therapies based on therapeutic antibodies that target tumor antigens such as Rituxan™ or Herceptin™ as well as anti-angiogenic antibodies such as anti-VEGF, or antibodies that target Apo2L receptors, such as DR5 or DR4.

Preparation and dosing schedules for chemotherapeutic agents may be used according to manufacturers' instructions or as determined empirically by the skilled practitioner. Preparation and dosing schedules for such chemotherapy are also described in *Chemotherapy Service* Ed., M. C. Perry, Williams & Wilkins, Baltimore, Md. (1992).

It may be desirable to also administer antibodies against other antigens, such as antibodies which bind to CD20, CD11a, CD18, CD40, ErbB2, EGFR, ErbB3, ErbB4, vascular endothelial factor (VEGF), or other TNFR family members (such as DR4, DR5, OPG, TNFR1, TNFR2). Alternatively, or in addition, two or more antibodies binding the same or two or more different antigens disclosed herein may be co-administered to the patient. Sometimes, it may be beneficial to also administer one or more cytokines to the patient. In one embodiment, the Apo2L formulations are co-administered with a growth inhibitory agent.

The Apo2L/TRAIL formulation may be administered concurrently or sequentially with such other agents. For example, the Apo2L/TRAIL formulation or a chemotherapeutic agent may be administered as a pre-treatment (prior to administration of any such other agents), such as a pre-treatment of cancer cells which may otherwise be resistant to the apoptotic effects of Apo2L/TRAIL.

The invention also provides kits which include a formulation described herein. A typical kit will comprise a container, preferably a vial, for Apo2L/TRAIL in one or more excipients as described above; and instructions, such as a product insert or label, directing the user as to how to employ the Apo2L/TRAIL formulation. This would preferably provide a pharmaceutical formulation. Preferably, the pharmaceutical formulation is for treating cancer or an immune related condition. Suitable containers include, for example, bottles, vials, syringes, and test tubes. The containers may be formed from a variety of materials such as glass or plastic. The container holds an Apo2L/TRAIL formulation that is effective for diagnosing or treating the disorder and may have a sterile access port (for example, the container may be an intravenous solution bag or a vial having a stopper pierceable by a hypodermic injection needle). The label on, or associated with, the container indicates that the formulation is used for diagnosing or treating the disorder of choice. The article of manufacture may further comprise a second container comprising water-for-injection, a pharmaceutically-acceptable solution, saline, Ringer's solution, or dextrose solution. It may further include other materials desirable from a commercial and user standpoint, including other buffers, diluents, filters, needles, syringes, and package inserts with instructions for use.

All patents, patent applications, publications, product descriptions, and protocols are cited throughout this application, the disclosures of which are incorporated herein by reference in their entireties.

EXAMPLES

The following examples are offered for illustrative purposes only, and are not intended to limit the scope of the present invention in any way. Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Formulations were prepared and assays were conducted to identify Apo2L/TRAIL formulations having desirable characteristics from a therapeutic, diagnostic, and/or commercial standpoint. In particular, Applicants sought to identify formulation components and conditions that, among other things, may enhance solubility of biologically active Apo2L/TRAIL, particularly at concentrations up to at least 20 mg/ml, and may provide stability upon storage at 2-8° C. or at ambient temperature. Applicants also sought to identify Apo2L/TRAIL formulations for use in the clinic that may preserve the protein's native non-covalent trimer content, charge distribution, and/or biological activity during storage.

Example 1

Liquid Formulations of Apo2L/TRAIL with Enhanced Solubility and Stability

Apo2L/TRAIL protein consisting of amino acids 114-281 (see FIG. 1) was expressed in *E. coli* under the AP promoter control (preparation and expression described in Example 8 (Section A) of WO 01/00832 published Jan. 4, 2001), and purified from the *E. coli* cell lysates by three chromatographic steps consisting of cation exchange, hydroxyapatite, and hydrophobic interaction chromatography (WO 01/00832, Example 8, Section C). In the third chromatographic separation, the Apo2L/TRAIL protein was eluted in 600 mM Na sulfate or 400 mM ammonium sulfate, 50 mM Tris, pH 7.5. The protein was then buffer exchanged to the various formulation excipients listed in Table 1 by dialysis, and was next concentrated at ambient temperature using Centricon-10 filtration up to concentrations of 20 mg/mL. The samples were then filtered through 0.22 micron filters and stored at either 2-8° C. or 30° C. to assess solubility and stability.

As shown in Table 1, about 20 different excipients were examined. High purity NF, USP, or EP grade excipients were used from common commercial sources (Sigma, Mallindkrodt) unless otherwise indicated as follows: alpha,alpha trehalose dihydrate (Pfanstiehl or Senn), sucrose (Pfanstiehl), Captisol™ (Cydex), Arginine free base (Ajinomoto or Kyowa Hakko Kogyo). Criteria used for initial excipient screening included 1) solubility at 2-8° C. (the storage condition of bulk preparations prior to fill in vials), 2) solubility under manufacturing scale ultrafiltration and diafiltration steps, 3) short term liquid stability and freeze-thaw stability, and 4) lyophilized formulation physical stability. Solubility at 2-8° C. was evaluated by periodic visual assessment of precipitation for up to 1 month and confirmed by UV spectroscopy scan using an extinction coefficient of 1.53 at 278 nm.

Table 1 indicates that excipients having relatively high ionic strength conditions provided solubility at concentrations of Apo2L/TRAIL above 10 mg/ml at 2-8° C.

TABLE 1

| Excipient | Solubility At 2-8° C. |
| --- | --- |
| 8% Trehalose | <3 mg/ml |
| 8% Sucrose | <3 mg/ml |
| 16% Sucrose | <2 mg/ml |
| 6% Lactitol | <2 mg/ml |
| 4% Sucrose/4% Mannitol | <2 mg/ml |
| 5% PEG3350 | <5 mg/ml |
| 20% Glycerol | <5 mg/ml |
| 0.15 M NaCl | <5 mg/ml |
| 0.25 M Na phosphate | <5 mg/ml |
| 0.5 M Glycine | <12 mg/ml |
| 0.5 M Aspartate | 10-20 mg/ml |
| 0.5 M Na sulfate | 10-20 mg/ml |
| 0.5 M Na acetate | >20 mg/ml |
| 0.5 M Na chloride | >20 mg/ml |
| 24% Sulfobutylether beta-cyclodextrin (Captisol ™) | >20 mg/ml |
| 0.5 M Tris | >20 mg/ml |
| 0.5 M Arginine-tartrate | >20 mg/ml |

Short-term liquid stability (1 week storage time period at 30° C.) was then evaluated for several of those preparations shown in Table 1 that provided solubility of Apo2L/TRAIL at concentrations of about 20 mg/ml. The short-term stability was assessed by visual assessment of turbidity, size exclusion HPLC (SEC) to determine the amount of native trimer and aggregates in the preparations, and by ion exchange HPLC (IEX) to determine the charge distribution. SEC was conducted using a 1) Superose 12 column (Pharmacia) or 2) 4.6 mm wide by 300 mm long Toso Haas TSK Super SW2000 column (TosoHaas) and a 13 mM Na phosphate, 400 mM ammonium sulfate (pH 6.5) mobile phase run at a rate of 1) 0.6 ml/min ro 2) 0.15 mL/min. IEX was conducted using a ProPac WCX-10 column (Dionex) at 40° C. and a NaCl gradient run at a rate of 0.5 ml/min.

The results are shown in FIG. 2. The sodium sulfate, arginine tartrate, Captisol™, and sodium acetate preparations exhibited the greatest stability in one or both of the assays (FIG. 2).

Example 2

Lyophilized Apo2L/TRAIL Formulations Containing Arginine Salts

Applicants found that Apo2L/TRAIL formulations containing arginine salts could be readily concentrated to >20 mg/mL protein by ultrafiltration and diafiltration. Because of certain in vivo pharmacokinetic properties of the Apo2L/TRAIL 114-281 amino acid form of the protein (described in Example 1), Applicants particularly sought to identify a stable formulation having >20 mg/ml Apo2L/TRAIL protein.

To identify those arginine salts that provide pharmaceutically and commercially viable lyophilized products, the physical stability of vehicle formulations containing different arginine salts was evaluated. Arginine salts were prepared by titrating 0.5M Arginine free base with various acids (shown in Table 2) to give a pH 7 solution in 20 mM Tris. 2 ml preparations were filled in 5 cc glass vials and subjected to a conservative long freeze-drying (lyophilization) cycle (freezing at −50° C., primary drying at 0° C. and secondary drying at 42° C.). Osmolality of the solutions (prior to lyophilization) was also determined using vapor pressure depression methods to identify those preparations that may be suitable for IV administration in a clinical setting.

Table 2 indicates that the lyophilized preparations containing polyanionic organic or inorganic acids exhibited more desirable physical stability than those prepared using monoanionic acids. The lyophilized products of the polyanionic salts appeared as solid intact dried cakes (indicated in Table 2 as "yes"), rather than melted, gelled, collapsed, fenestrated, egg-shaped or fragmented shells (indicated in Table 2 as "no").

In addition, 0.5M arginine salts of polyanionic acids demonstrated an osmolality which may be suitable for IV administration (less than 2.5-fold hypertonic), unlike the monoionic arginine salts (e.g. 0.5M arginine-lactate gives a 3.1× hypertonic solution) and some of the other relatively high ionic strength preparations that exhibited good solubility and liquid stability (e.g., 0.5 M sodium acetate gives a 3.4 fold hypertonic solution).

TABLE 2

| Arginine salts | Acceptable lyo physical stability? | Osmolality of 0.5 M solution* |
|---|---|---|
| Arg-citrate | Yes | 505 |
| Arg-tartrate | Yes | 530 |
| Arg-malate | Yes | 573 |
| Arg-succinate | Yes | 630 |
| Arg-oxalate | Yes | ND |
| Arg-lactate | No | 927 |
| Arg-glycolate | No | ND |
| Arg-acetate | No | 978 |
| Arg-glutamate | No | 899 |
| Arg-phosphate | Yes | 465 |
| Arg-sulfate | Yes | 462 |
| Arg-nitrate | No | 774 |
| Arg-HCL | No | 830 |

*Values are mosmol/kg. Isotonic solutions have an osmolality of approximately 292-300. "ND" indicates value was not determined.

Based on the results obtained in the study reported in Table 2, several lyophilized Apo2L/TRAIL-containing formulations were then evaluated for biochemical stability of the protein after storage at various temperatures. Apo2L/TRAIL (residues 114-281; prepared as described in Example 1) was formulated by ultrafiltration/diafiltration to 10 mg/ml in 0.5M arginine-tartrate or arginine-citrate, or to 3 mg/ml in 8% sucrose or trehalose. All of these preparations contained 20 mM Tris, pH 7.0 and 0.01% polysorbate 20. The samples were then lyophilized as described above. Stability was assessed by measuring content of native trimer and aggregates using SEC (described in Example 1) and charge distribution using IEX (described in Example 1).

After 4 months storage at 40° C., the % trimer and % IEX main peak was determined relative to an unlyophilized control solution that was stored at −70° C. (see FIG. 3A). The data in FIG. 3A indicates that the arginine salt-containing lyophilized formulations exhibited greater stability as compared to the formulation preparations containing sucrose or trehalose.

To further examine the effects of arginine-salt type on the stability of Apo2L/TRAIL formulations, both the liquid and the lyophilized formulations of four different arginine salt-containing 20 mg/ml Apo2L/TRAIL formulations were monitored for biochemical stability of the protein. Liquid stability was monitored at 2-8° C. and at ambient temperatures for up to 1 month (Table 3) and lyophilized stability was monitored at 50° C. for one month (FIG. 3B).

In addition to conducting SEC and IEX assays described in Example 1, covalent dimer formation was monitored by SEC under denaturing conditions (SDS-SEC). The SDS-SEC assay was conducted using a TSK G2000SWXL column (TosoHaas) run at 0.6 ml/min in a mobile phase consisting of 25 mM sodium phosphate, 0.1% SDS, 200 mM NaCl. Samples were diluted to 1 mg/ml protein with a solution that gave 50 mM Tris (pH 7.0), 200 mM NaCl, 0.5% SDS, pH 9 and 5 mM iodoacetamide (Sigma). Samples were then incubated at 50° C. for 10 minutes prior to HPLC analysis.

Bioactivity of the Apo2L/TRAIL in the various formulations was also determined using SK-MES-1 cells and Alamar Blue staining for viable cell counts. In the assay, the Apo2L/TRAIL formulation (50 uL at 2 ug/mL) was added to assay medium (0.1% Bovine Serum Albumin, RPMI 1640) and 2-fold serial dilutions were made in 96-well plates. Then, 50 uL SK-MES-1 cells (human lung carcinoma cell line, ATCC HTB58) were added into the wells at 20000 cells/well density. The plates were incubated for 24 hours at 37° C., and Alamar Blue was added for the last 4 hours of the 24 hour incubation time. The staining intensity was determined on a fluorescence plate reader with excitation wavelength set at 530 nm and emission at 590 nm. A four-parameter fit to the data in the assay range of 0.1 to 1000 ng/ml gives the ED50, or the concentration of Apo2L/TRAIL that induces 50% killing of the cells. Cell killing potency increases with decreasing ED50.

As shown in Table 3, after 1 month storage of the liquid formulations at 2-8° C., the four arginine-salt containing formulations showed only small differences in Apo2L/TRAIL quality. The arginine-sulfate formulation exhibited the highest extent of aggregate formation. The arginine-malate formulation exhibited the highest extent of dimer formation, and the arginine-phosphate and arginine-malate formulations showed the largest change in the IEX % main peak area.

After 2 weeks storage at ambient temperature, the arginine-sulfate and arginine-succinate formulations retained the highest level of bioactivity (Table 3).

Overall, the arginine-succinate formulation demonstrated somewhat superior stability characteristics for Apo2L/TRAIL in the liquid state.

TABLE 3

| Formulations | % Trimer[1] | % IEX main peak remaining[1] (% of control) | % Monomer[1] | % bioactivity[2] |
|---|---|---|---|---|
| Arginine-malate | 96.2 | 105.1 | 93.4 | 77.0 |
| Arginine-succinate | 96.2 | 94.7 | 94.9 | 88.5 |
| Arginine-sulfate | 95.4 | 93.4 | 93.3 | 90.5 |
| Arginine-phophate | 96.0 | 91.0 | 91.8 | 74.3 |

[1]Data are for 1 month storage at 2-8° C.
[2]Data are for 2 weeks storage at ambient temperature.

The stability of the lyophilized formulations containing these arginine-salts after 1 month storage at 50° C. was also assessed by SEC, IEX and SDS-SEC (using the protocols described above). No changes in the physical-chemical properties were observed (see FIG. 3B), suggesting that significant stabilization of Apo2L/TRAIL may be achieved through lyophilization of Apo2L/TRAIL formulations containing arginine-salts. An Arrhenius profile using accelerated temperature stability of a lyophilized 10 mg/ml Apo2L/TRAIL formulation in 0.5M arginine-tartrate, 20 mM Tris, pH 7.0, 0.01% polysorbate 20, 0.33 mM Zn sulfate is shown in FIG. 3C, and predicts a relatively long shelf life at 2-8° C., and a >2 year shelf-life at ambient temper'ature. Applicants have found that a lyophilized formulation ("lyo") containing 20 mg/mL Apo2L/TRAIL in 20 mM Tris, pH 7.2, 0.5 M arginine-succinate and 0.02% polysorbate 20 was stable at temperatures as high as 50° C. for at least 12 months (Table 4). The kinetics of change in IEX % main peak predicts a significantly long (>7 year) shelf life at 2-8° C. (as well as at ambient temperature), as with the formulation described above in FIG. 3C.

TABLE 4

| Temperature | % Trimer | % IEX main peak | % Monomer |
| --- | --- | --- | --- |
| −70° C. liquid control | 97.4 | 46.1 | 99.0 |
| Lyo, 2-8° C., 12 mo | 97.5 | 46.5 | 99.0 |
| Lyo, 30° C., 12 mo | 97.3 | 45.4 | 98.8 |
| Lyo, 40° C., 12 mo | 97.4 | 44.6 | 98.8 |
| Lyo, 50° C., 12 mo | 97.3 | 42.5 | 98.7 |

Example 4

Effects of pH in Apo2L/TRAIL Formulations

As described in WO 01/00832 published Jan. 4, 2001 (see also, Hymowitz et al., *Biochemistry*, 39:633-640 (2000), Apo2L/TRAIL protein forms a homotrimer with a Zn-coordinated thiol at position cysteine 230 of each monomer, and the formation of an intramolecular disulfide bond at cysteine 230 results in loss of bioactivity of the protein. Cysteine-containing proteins are typically formulated at low pH, well below the pKa of the thiol groups, to prevent disulfide bond formation (see, e.g., N. Derby and T. Creighton, "Disulfide Bonds in Protein Folding and Stability," Methods in Enzymology, Vol 40 (Edited by B. A. Shirley; Humana Press Inc, Totowa, N.J.), Chapter 10 (1995)). Surprisingly, as the results discussed below reveal, the stability of native, non-covalent Apo2L/TRAIL trimer was found to decrease with decreasing pH.

Apo2L/TRAIL consisting of amino acids 94-281 (FIG. 1) (referred to herein and in FIG. 4 as "Apo2L/TRAIL.2") was prepared essentially as described in WO 01/00832, except that a Ni-chelating affinity chromatography, instead of HIC, was used as the third chromatographic step. Formulations were prepared by dialysis into 10 mM Na succinate (pH range 5.5 to 6.5) or 10 mM Na phosphate (pH range of 7 to 7.5). Liquid stability of these formulations was assessed by SEC and bioactivity assays according to procedures described in the Examples above.

Within one day storage at ambient temperature, the formulations having pH below about pH 6.5 lost trimer content and bioactivity (see FIG. 4A). This pH-stability profile was observed with other Apo2L/TRAIL protein variants. For example, a poly-histidine-tagged Apo2L/TRAIL formulation consisting of amino acids 114-281 (FIG. 1) (His-Apo2L/TRAIL; prepared essentially as described by Ashkenazi et al., "Safety and Antitumor Activity of Recombinant Soluble Apo2 ligand", *JCI*, 104:155-162 (1999) was prepared in 10 mM Na succinate (pH 5.5 to 6) or 10 mM Na phosphate buffers (pH 6.5 to 7). After storage at 30° C. for 1 week, the stability of trimer and bioactivity (determined as described above for the formulations of FIG. 4A) was found to be enhanced at pH ≧6.5 (see FIG. 4B).

Crystal structure analysis of Apo2L/TRAIL reveals that coordination of an intrinsic Zn atom to three free thiols of cysteine 230 is needed for proper folding and native structural stability of the protein (see WO 01/00832 and Hymowitz et al., supra). The unexpected pH-stability profile of Apo2L/TRAIL, although not fully understood, is believed to be associated with loss in Zn binding to the trimer as the thiol moiety becomes more protonated at lower pHs (see FIG. 5). It is believed that neutral pH in the range of about 6.5 to about 8.5 will be most preferred for maintaining the bioactivity and physical-chemical stability of Apo2L/TRAIL formulations.

Example 5

Effect of Surfactant on Stability of Apo2L/TRAIL

To examine the effect of surfactant on stability of Apo2L/TRAIL formulations, formulations containing 20 mg/ml Apo2L/TRAIL (114-281 protein (FIG. 1); prepared as described in Example 1) in 0.5 M arginine-succinate, 20 mM Tris, pH 7.2, and varying concentrations of Tween 20 (0.005%, 0.01%, 0.02%, or none (as control)) were prepared and agitated at 70 rpm and ambient temperature for up to 24 hours in glass vials positioned horizontally. Within 1 hour of agitation, an increase in light scattering (measured by absorbance in the range of 340-360 nm) was observed as the concentration of Tween 20 fell below 0.005% (FIG. 6).

It is therefore believed that it may be preferable to include non-ionic surfactant(s) such as Tween 20 in Apo2L/TRAIL formulations to enhance stabilization against agitation and handling that can denature the bulk protein at air-water interfaces.

Example 6

Effect of Zn Sulfate on Stability of Liquid Apo2L/TRAIL Formulations

A liquid formulation of Apo2L/TRAIL protein consisting of residues 114-281 (FIG. 1) (prepared as described in Example 1) was prepared using 20 mg/ml Apo2L/TRAIL, 0.5M arginine-tartrate, 20 mM Tris, pH 7.0, in the presence of zero, 117 uM, or 330 uM Zn sulfate. After storage at 30° C. or 2-8° for up to 2 months, stability was evaluated by SEC, IEX, and SDS-SEC (as described above in Examples 1 and 2) relative to −70° C. control samples.

As shown in FIG. 7, addition of Zn sulfate to the formulations provided increased stabilization against disulfide-linked intramolecular dimer formation. Though Zn sulfate did not affect the stability of Apo2L/TRAIL at 2-8° C., it improved stability towards dimer formation at higher temperatures (FIG. 7).

Example 7

Reversible Crystallization of Biologically Active Apo2L/TRAIL

Applicants have found that under conditions of low Apo2L/TRAIL solubility (for example, at moderate to low ionic strength), the protein can be crystallized. As described herein, the crystallization rate, particle size, and yield can be controlled to give useful industrial methods for purification, bulk storage, and controlled release suspension formulation of Apo2L/TRAIL.

Apo2L/TRAIL protein consisting of residues 114-281 (FIG. 1) (prepared as described in Example 1) was formulated at ambient temperature using NAPS column (Pharmacia) elution in 20 mM Tris, pH 7.2 and various concentrations of Na sulfate. After elution at ambient temperature, within hours, hexagonal shaped crystals of varying lengths were observed (see FIG. 8). Equilibrium solubility was reached when samples were continuously rotated for 3-4 days at a given temperature. There was a minimum in solubility at approximately 10-50 mM ionic strength. Solubility increased to a maximum at approximately 0.3 M Na sulfate and then decreased until limiting solubility of the salt was reached. The pattern was similar at higher temperatures, but solubility increased with increasing temperature. The observation of increasing protein solubility (hence decreased crystallization) with increasing salt concentration in the hundreds of millimolar salt range is unlike common understanding with respect to other proteins, where crystallization propensity tends to increase with increasing salt concentration (see, e.g., A. Ducruix and MM Reis-Kautt, "Solubility Diagram Analysis and the Relative Effectiveness of Different Ions on Protein Crystallization," METHODS: A Companion to Methods in Enzymology, Vol. 1, pp. 25-30 (1990)).

Monovalent cationic salts (such as sodium chloride) provided the greatest crystallization propensity as shown in FIG. 9, while divalent cationic salts (e.g. calcium chloride and magnesium chloride) significantly reduced crystallization. Crystallization also occurred in positively charged (lysine-salts and arginine-salts) and negatively charged (aspartic acid) amino acid solutions below 0.3 molar concentration (see FIG. 9), though arginine salts reduced crystallization propensity at the same ionic strength.

To identify various crystallization process parameters, a 0.5 L solution containing 5 mg/ml Apo2L/TRAIL (residues 114-281; prepared as described in Example 1), 0.1M $Na_2SO_4$ and 20 mM Tris at pH 7.2 was subjected to a single step cooling from room temperature to 5° C. Four experiments were performed with agitation rates ranging from 0 to 200 rpm. The supernatant concentration of Apo2L/TRAIL was measured in 10-minute intervals using UV spectroscopy to monitor the progress of crystallization.

FIG. 10A shows that crystallization was more than 90% complete within 2 hours when the bulk was agitated at 50 rpm or faster. Crystallization without agitation was much slower in comparison. Static crystallization did not reach 90% completion until 2 days after cooling began. Crystallization rate appeared to increase with increasing agitation speed.

FIG. 10B depicts the dissolution profile of Apo2L/TRAIL crystals under agitation. The crystal slurry was warmed from 5° C. to 30-35° C. with the same heating rate in each dissolution experiment. Apo2L/TRAIL concentration in the supernatant was measured in 5-minute intervals to monitor dissolution rate. The crystal dissolution rate increased when agitation speed was increased from 50 rpm to 200 rpm. Heat transfer rate between the tank jacket and the crystal slurry was also enhanced when agitation speed increased. At 100 rpm agitation rate, complete dissolution was achieved within a half hour when the sample temperature was at approximately 35° C.

FIG. 10C shows the crystal size distribution as a function of agitation speed during crystallization. Crystal size distribution was measured using a Malvern MasterSizerX Particle Size Analyzer. The mean diameter (D[v, 0.5]) decreased as agitation speed increased, and the crystal size distribution (D[v, 0.1] to D[v, 0.9]) became more uniform with faster agitation. Therefore, manipulating the agitation rate during crystallization appears to be effective in controlling the mean diameter of the Apo2L/TRIAL crystals as well as the crystal size distribution, which may be desirable for controlled release formulations.

Example 8

Drying of Apo2L/TRAIL Crystals

To assess the feasibility of drying Apo2L/TRAIL crystals for controlled release formulation or bulk storage, three different drying methods were evaluated.

The first drying method evaluated was static vacuum drying. Apo2L/TRAIL (amino acids 114-281; purified according to the method described in Example 1) was crystallized in 20 mM Tris, 0.1 M sodium sulfate, pH 7.2 and washed with cold water to remove excess salt. The crystal slurry was filled in open glass vials and dried under 29-30 inches of mercury vacuum at ambient temperature overnight. The dried crystals were dissolved to 2-3 mg/ml in either water or in 0.5 M arginine-salt, 20 mM Tris, pH 7.2.

The second drying method evaluated was vibrational vacuum drying (apparatus obtained from SWECO Co.) to allow better flow and decrease solid clumping. The crystal slurry was loaded on a 20 um filter to remove the bulk liquid, and the wet crystals were washed with cold Tris buffer (20 mM, pH 7.5) or ethanol-water mixture (50%, 63%, 75%, 100%, v/v). The washed crystals were dried by passing dehumidified nitrogen gas from the bottom of the filter. A slight vacuum (8-10 inches of mercury) from the top of the filter chamber facilitated the drying rate. Furthermore, the filter chamber containing the wet crystals vibrated at 1,800 rpm to break up the wet cake into fine powder during the drying process. The drying process was monitored using a relative humidity sensor. Dried product was recovered through a discharge port. The ethanol-water mixture washes produced finer and better flowing powder than crystals washed with Tris buffer, which in turn increased the process yield. These crystals were dissolved in a buffered 0.5M arginine salt, as described for the vacuum dried crystals.

The third drying method evaluated was lyophilization. In this method, the crystal slurry was washed with cold water and filled in glass vials. Excess bulk water was removed after the crystals settled. The slurry was then frozen to −50° C. Primary and secondary drying were carried out at −25° C. and 0° C., respectively. These crystals were better flowing powders and dissolved readily in buffered 0.5M arginine-salts.

The protein quality in the dissolved crystals was then assessed using SEC, SDS-SEC, IEX, and bioactivity assays as discussed in Examples 1 and 2. Table 5 and FIGS. 11A-11B show that Apo2L/TRAIL crystals dried with the different methods remained biochemically equivalent to the non-crystallized frozen liquid control preparation.

TABLE 5

| Drying method | % trimer by SEC | % monomer by SDS-SEC | % IEX main peak |
|---|---|---|---|
| Control (frozen starting material) | 98.0 | 96.8* | 53.6 |
| Vibrational vacuum drying - water wash | 97.4 | 98.1 | 54.9 |
| Vibrational vacuum drying - 50% ethanol wash | 97.7 | 97.5 | 53.7 |
| Vibrational vacuum drying - 62.5% ethanol wash | 97.9 | 97.5 | 53.4 |
| Vibrational vacuum drying - 75% ethanol wash | 97.7 | 97.7 | 52.8 |
| Vibrational vacuum drying - 100% ethanol wash | 97.8 | 98.0 | 53.3 |

*The apparent lower % monomer in control sample by SDS-SEC is due to impurities in the starting material which co-elute with Apo2L dimer on SDS-SEC.

The data suggest that crystallization of Apo2L/TRAIL and subsequent drying of the material does not adversely affect protein structure or function.

Example 9

Lyophilized Formulation of Crystalline-containing Apo2L/TRAIL in Sodium Sulfate

To assess storage stability of crystal-containing Apo2L/TRAIL, lyophilized formulations were prepared with crystalline Apo2L/TRAIL (residues 114-281) in 20 mM Tris, pH 7-7.5, 0.2-0.5M sodium sulfate, and 0.01-0.05% Tween 20. The samples were stored at various temperatures for up to 4 months. After reconstituting with sterile water, the formulations were tested for physical-chemical stability using SEC, IEX, and SDS-SEC assays described in Examples 1 and 2. Table 6 summarizes the data for a 20 mg/ml Apo2L/TRAIL formulation in 0.2 M Na sulfate, 20 mM Tris, pH 7.2, 0.01% Tween 20 after 3 months storage.

TABLE 6

| Temperature | % Trimer | % IEX main peak | % Monomer |
|---|---|---|---|
| −70° C. liquid control | 99.3 | 56.1 | 99.1 |
| Lyo, 2-8° C., 3 mo | 99.1 | 58.2 | 99.3 |
| Lyo, 30° C., 3 mo | 97.0 | 56.4 | 98.3 |
| Lyo, 40° C., 3 mo | 94.1 | 52.9 | 95.9 |
| Lyo, 50° C., 3 mo | 90.1 | 44.8 | 91.7 |

Assuming a pseudo-first order degradation kinetics, Arrhenius profiles predict significantly longer than 2 years shelf-life for this formulation at 2-8° C. (see FIG. 12). These preparations, though filled as clear liquid solutions of Apo2L/TRAIL, crystallize to varying degrees during the freezing portion of the lyophilization cycle, demonstrating that dried formulations containing crystallized Apo2L/TRAIL and sodium sulfate have long term storage stability.

Example 10

Apo2L/TRAIL Crystallization as a Method of Recovery and Purification

The propensity of crystallization of Apo2L/TRAIL in Na sulfate solutions was used as a means of purifying the Apo2L/TRAIL protein from *E. coli* extracts. The following protocol may be employed for recovery and purification of recombinant Apo2L/TRAIL without adverse effect on protein quality.

The harvested whole cell broth derived from *E. coli* (described in Example 1) was adjusted to pH 7.5 with 1.5 M Hepes (or 1.5M Tris) and then homogenized in a homogenizer (Gaulin corporation, Everett, Mass.). The homogenate was conditioned with 5 mM DTT and flocculated with 0.1% polyethyleneimine for 1-2 hours. The flocculated material was centrifuged by a BTPX205 (Alfa Laval Separation AB, Sweden) continuous feed centrifuge and clarified by depth filtration. The clarified cell lysate (extract) was conditioned with Triton-X100 to a final concentration of 0.05%. The conditioned, clarified cell lysate was then loaded onto a cation exchange column (SP-Sepharose FF cation exchange resin, Amersham Pharmacia, Sweden) equilibrated in 50 mM Hepes (or 50 mM Tris)/0.05% Triton-X 100/1 mM DTT, pH 7.5. Apo2L/TRAIL bound to the column while the non-binding proteins flowed through the column and were removed by washing with equilibration buffer until absorbance at 280 nm reached baseline. The column was then washed with 3 column volumes of 0.1 M NaCl in equilibration buffer. The Apo2L/TRAIL was step-eluted using 0.1 M NaCl (or 0.1M Na$_2$SO$_4$) in 50 mM each of Hepes, Tris and Triethanolamine, 0.05% Triton-X 100 and 1 mM DTT buffer, pH 7.8.

The ambient temperature Apo2L/TRAIL pool collected from the SP column was placed in a stainless steel tank with an insulated jacket for heating and cooling. The tank was outfitted with a conical bottom and a flush bottom valve for maximal recovery of crystallized protein. The pool was agitated using a marine type impeller under modest mixing conditions. A temperature control skid was used to linearly ramp the temperature from approximately 25° C. to approximately 4° C. over the course of 1 hour. Spontaneous crystallization was observed within minutes after the pool reached 4° C. After more than 12 hours under these conditions, crystallization was complete as equilibrium solubility was nearly established. The crystals were then captured on a filtration assembly containing a 20 um polypropylene frit. Following crystal deposition on the filter surface, the crystals were washed with chilled 20-50 mM Tris at pH 7.5. An equal volume of wash buffer compared to the Apo2L/TRAIL SP pool volume was then used to remove residual mother liquor (supernatant) from the deposited crystals. Following the wash, the crystals were dissolved in 100 mM sodium sulfate/20 mM Tris at pH 7.5 by recirculating the dissolution buffer through the crystal bed at approximately 30° C. Dissolution of the crystals was observed within approximately 4 hours. The dissolved, purified Apo2L/TRAIL was then sterile filtered into a container and stored frozen at −70° C.

The purity of the Apo2L/TRAIL preparations was determined by the total *E. coli* protein (ECP) ELISA assays, *Limulus Amebocyte* Lysate (LAL) assay, and SDS-PAGE silver stain. ECP ELISA was performed by immobilizing affinity-purified goat anti-whole ECP antibodies on microtiter plate wells, incubating samples and then horseradish peroxidase-conjugated ECPs. The peroxidase enzymatic activity was then quantified with o-phenylenediamine by reading absorbance at 490 nm in a microtiter plate reader. Endotoxin level was determined using the *Limulus Amebocyte* clot lysis assay. SDS-PAGE silver stain was performed on a 10 to 20% gradient polyacrylamide gel (Daiichi Pure Chemicals) in Tris-glycine buffer containing 0.1% SDS. Electrophoresis was conducted at 50 mA constant current until dye front reached near the bottom of the gel. Gels were fixed and stained by Coomassie Brilliant Blue or Merrill silver stain methods.

Protein quality was assessed by SEC, SDS-SEC, IEX, and bioactivity according to methods described in Examples 1 and 2.

The purity and quality of Apo2L/TRAIL recovered using the above crystallization method at a 60 L fermentation scale is shown in Table 7. For comparison, a reference standard purified by a three-chromatographic step method as described in Example 1 is also shown.

TABLE 7

| Apo2L/ TRAIL Prep. | Protein Purity | | | Protein Quality | | | |
|---|---|---|---|---|---|---|---|
| | ECP (ppm) | LAL (EU/mg) | SDS-PAGE | % Trimer by SEC | % Monomer by SDS-SEC | Bio-activity % of control (±20%) | % IEX main peak |
| Apo2L/TRAIL purified by crystallization | 10 | 0.034 | No band at 10 kDa | 99.0 | 99.0 | 126 | 63 |
| Reference material purified by standard chromatography | 0.82 | 0.023 | Band at ~10 kDa | 98.9 | 98.9 | 86 | 61 |

As shown in Table 7 and FIG. 13, the Apo2L/TRAIL preparation at a manufacturing scale had a high degree of purity suitable for therapeutic use. In particular, a 10 kDa E. coli DNA binding protein that tends to co-purify with Apo2L/TRAIL was removed by the crystallization process. The data indicate that the "one-column" step purified Apo2L/TRAIL protein is amenable to crystallization and has a purity comparable to or better than the Apo2L/TRAIL protein purified by the three-column purification method described in Example 1. FIG. 14 shows the effect of salt type on crystallization of a one-column step purified Apo2L/TRAIL. "Poisoning" of crystallization by divalent cations was observed for partially purified Apo2L/TRAIL (FIG. 14), similar to that observed for >99% purified Apo2L/TRAIL shown in FIG. 9.

The biochemical properties of Apo2L/TRAIL were also not adversely impacted by crystallization of the partially purified Apo2L/TRAIL (see Table 7). The data suggest that crystallization of recombinant-expressed Apo2L/TRAIL, when in a partially purified state, can be an effective, efficient and cost-effective means for its purification. Optionally, such crystals can then be used for preparation of dried bulk for storage or controlled release formulations as described in Examples 8 and 9.

Example 11

Effect of Excipients on the Stability of Dried Apo2L/TRAIL Crystals

Experiments were conducted to examine the effects of adding trehalose, Tween 20, Captisol™, and/or arginine to the slurry supernatant of Apo2L/TRAIL crystals, particularly the effects on the stability of lyophilized product.

Materials: 10 g Apo2L/TRAIL protein (amino acid residues 114-281 of FIG. 1 prepared and purified according to the methods described in Example 1 or Example 10) formulated at 10 mg/mL in 20 mM Tris, 0.1M $Na_2SO_4$ pH 7.2. 188 mg/mL (500 mM) αα-trehalose dihydrate in 20 mM TRIS pH 7.2, 37.6 mg/mL (100 mM) αα-trehalose dihydrate in 20 mM TRIS pH 7.2. 6 mg/mL (5 mM) Tween 20 in 20 mM TRIS pH 7.2. 10.5 (5 mM)mg/mL Captisol™ in 20 mM TRIS pH 7.2. 4.35 mg/mL (25 mM) arginine free base, 20 mM TRIS neutralized to pH 7.2 with succinic acid, 0.87 mg/mL (5 mM) arginine free base, 20 mM TRIS neutralized to pH 7.2 with succinic acid Methods: 10 mg/mL Apo2L/TRAIL in 20 mM TRIS, 0.1M $Na_2SO_4$ pH 7.2 was crystallized utilizing a single step cooling ramp as described above. After crystallization, the supernatant was removed, and the crystals were washed three times with cold water. The crystals were re-slurried to 100 mg/mL (final volume) and filled at 1 mL (100 mg, 1.67 umoles) per 3 cc glass vial. The crystals were allowed to settle to the bottom of the vials, and 1 mL of the supernatant water was removed. 1 mL of each of the following solutions was then added to each of 13 vials and swirled gently to mix the slurry.

TABLE 8

| Formulation # | Excipient | Solution Concentration | umoles excipient added | Excipient: Apo2L molar ratio |
|---|---|---|---|---|
| XF0 | N/A | N/A | 0 | 0 |
| XF1 | Trehalose | 188 mg/mL | 500 | 300 |
| XF2 | Trehalose | 37.6 mg/mL | 100 | 60 |
| XF3 | Tween 20 | 6 mg/mL | 5 | 3 |

TABLE 8-continued

| Formulation # | Excipient | Solution Concentration | umoles excipient added | Excipient: Apo2L molar ratio |
|---|---|---|---|---|
| XF4 | Captisol | 10.5 mg/mL | 5 | 3 |
| XF5 | Arginine | 0.87 mg/mL | 5 | 3 |
| XF6 | Arginine | 4.35 mg/mL | 25 | 15 |

All of the vials were lyophilized as described in Example 8 and stoppered at the end of secondary drying at 0° C. under vacuum.

Three vials of each formulation were placed at 2-8° C., 30° C., 40° C., and 50° C. One vial was analyzed for t=0 comparison. t=0 assays included: TGA (thermogravimetric analysis) for moisture content, SEC for aggregation, SDS-SEC for covalent dimer formation, and IEX for charge variants. SDS-SEC was performed both by the method described previously (Examples 1 and 2) as well as in the presence of a reducing agent (reduced SDS-SEC) to determine the extent of formation of non-thiol, covalently bonded species. Each sample was reconstituted to approximately 20 mg/mL with 20 mM TRIS, 0.5M arginine succinate, 0.02% tween 20 pH 7.2.

Figure 15B:
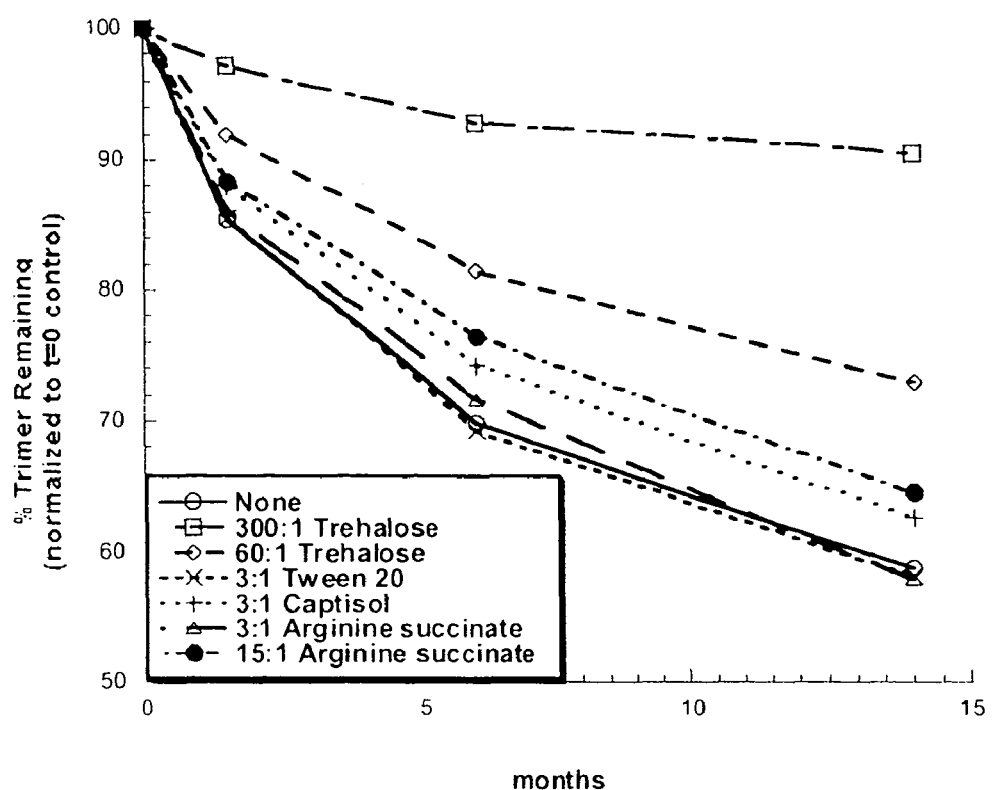
Figure 15C:
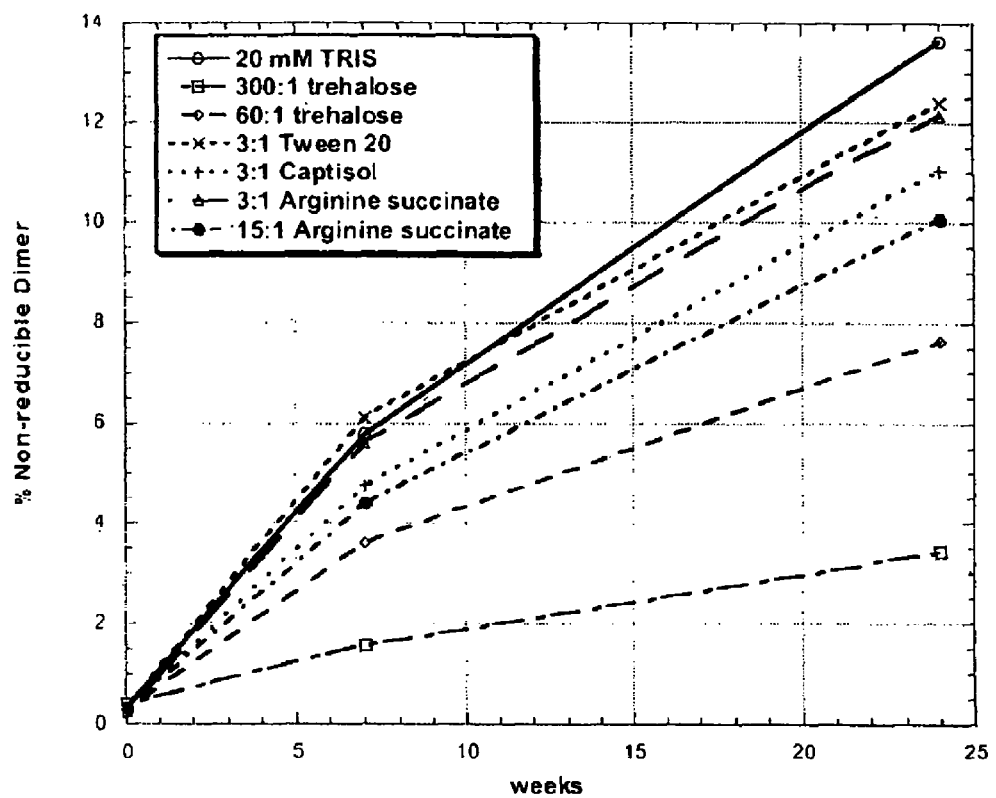

The results are illustrated in FIGS. 15A-15C. Stability of the lyophilized crystal compositions was assessed by determining loss of Apo2L/TRAIL trimer by SEC and SDS-SEC on reduced and non-reduced samples. FIG. 15A shows the results for the samples identified in TABLE 8, tested at Day 0 to 24 weeks at 30° C. FIG. 15B shows the results after storage of the samples at 50° C. over the course of a number of months. The sample "20 mM Tris" was used as a control and consisted of Apo2L/TRAIL crystals co-lyophilized with the excipient carrier buffer (20 mM TRIS) alone. At both temperatures, the results indicate that Apo2L/TRAIL crystals having excipients such as trehalose and arginine added prior to lyophilization have a slower rate of aggregation compared to control. FIG. 15C illustrates the increase in % non-reducible dimer at 50° C. observed in the samples over the course of 24 weeks. These results indicate that addition of excipients such as trehalose, Tween 20, Captisol™, or arginine to Apo2L/TRAIL crystals prior to drying may decrease the formation rate of this species in the protein, thereby leading to greater storage stability.

It is presently believed that the addition of one or more sugars or other excipients to crystalline forms of the Apo2L/TRAIL protein may be useful in decreasing formation of hexameric or higher oligomeric forms of the protein.

Example 12

Effects of Water Content on Crystalline Apo2L/TRAIL

The effects of water content on Apo2L/TRAIL protein crystals was examined using size exclusion chromatography (SEC) and SDS-SEC, on reduced and non-reduced samples, as described in the Examples above. Apo2L/TRAIL protein was crystallized from 20 mM Tris, 0.1M $Na_2SO_4$, pH 7.2, as described above. The crystals were washed three times with cold water, slurried in water to a final concentration of approximately 100 mg/ml, and filled at 1 mL per 3 cc vial. The crystals were lyophilized as previously described with one third of the vials stoppered at each of three timepoints: end of 1° drying, part-way through 2° drying and at the end of 2° drying, corresponding to approximately 5%, 4%, and 2% water, respectively.

The stability of the crystal samples was analyzed over the course of time at 50° C. by measuring loss of trimer using SEC and loss of monomer to covalent dimer by both SDS-SEC and reduced SDS-SEC.

Figure 16A:
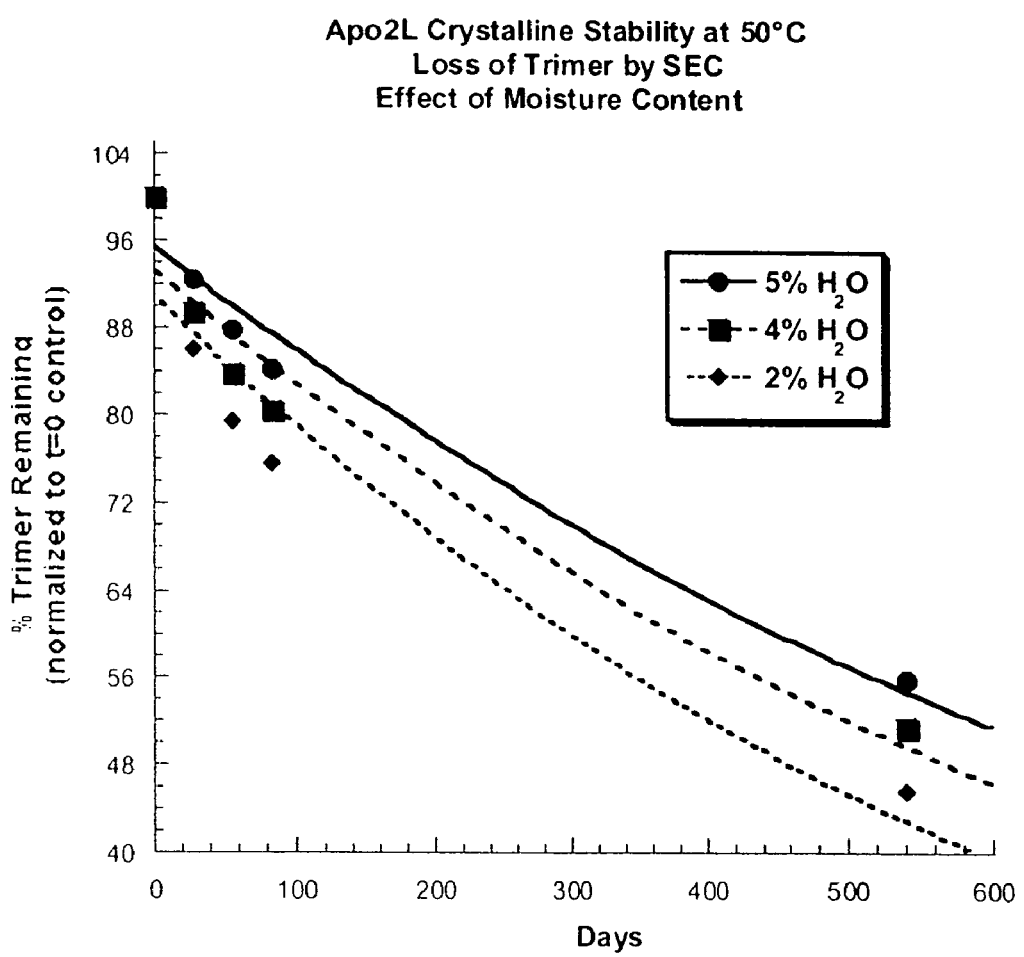
FIGS. 16A-16B show the effects of residual moisture content on the stability of lyophilized Apo2L/TRAIL crystals.
Figure 16B:
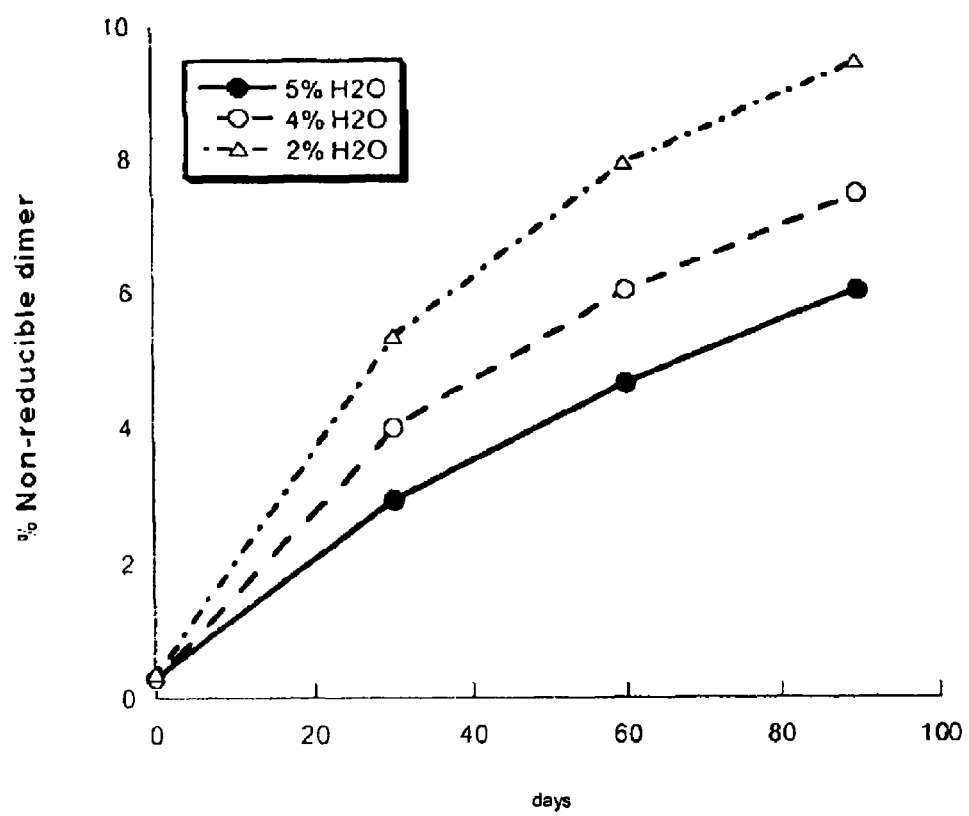

The results are shown in FIGS. 16A and 16B.

These results indicate that partial lyophilization of the Apo2L/TRAIL crystals which results in residual moisture contents greater than 2% decreases the rate of aggregate (FIG. 16A) and covalent dimer (FIG. 16B) formation of the protein.

Example 13

Effects of Water Content on Dimer and Higher Aggregated Formation in Crystalline Apo2L/TRAIL Compositions Apo2L/TRAIL protein (prepared and purified as described in Example 10) was resolubilized in 20 mM Tris, 0.1M $Na_2SO_4$, pH 7.2, and crystallized utilizing a single step temperature decrease as described above. The crystals were slurried in water to a final concentration of approximately 60 mg/ml and filled in vials at 1 ml (60 mg, 0.1 micromole) per 3 cc glass vial. The crystals were lyophilized and the vials stoppered at the end of 2° drying at 0° C. under vacuum, corresponding to approximately 2% water.

Approximately 40 of the vials were opened and placed at ambient temperature in each of four chambers having the following relative humidities ("RH") at 20° C.:

TABLE 9

| Approximate $H_2O$ content | RH @ 20° C. | SATURATED SALT SOLUTION |
|---|---|---|
| 5% | 20 | $KC_2H_3O_2$ |
| 10% | 44 | $K_2CO_3$•$2H_2O$ |
| 15% | 57.9 | NaBr•$2H_2O$ |
| 20% | 75.7 | NaCl |

The vials were then stoppered and placed at 2-8°, 15°, 30°, or 50° C.

At t=0, the actual water content of the samples was determined by thermogravimetric analysis (TGA). The TGA was conducted using a TGA instrument (Q Series™, TA Instruments, New Castle, Del.) and the temperature of the oven was ramped to 120° C. and held until the sample weights equilibrated.

The residual moisture content as measured by TGA is reported below in Table 10. The water content of those samples stored after 7 months at 50° C. was also measured by TGA and is reported in Table 10.

TABLE 10

| Relative Humidity | $H_2O$ Content Expected (t = 0) | $H_2O$ (%) Actual (t = 0) | $H_2O$ Content @ t = 7 mo, 50° C. |
|---|---|---|---|
| N/A | 2% | 2.5 ± 0.2% | 2.7 ± 0.1% |
| 20 | 5% | 6.7 ± 0.0% | 5.7 ± 0.1% |
| 44 | 10% | 8.8 ± 0.2% | 7.1 ± 0.0% |
| 57.9 | 15% | 10.4 ± 0.4% | 8.0 ± 0.0% |
| 75.7 | 20% | 11.8 ± 0.4% | 9.4 ± 0.2% |

Figure 17A:
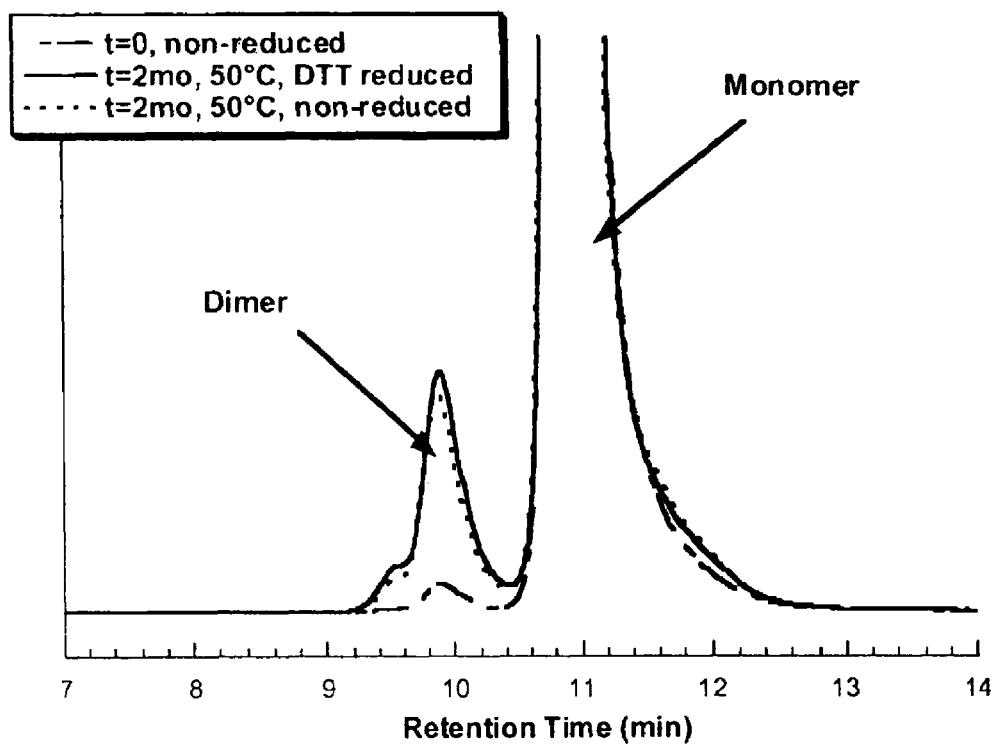
FIGS. 17A-17B show the relative amounts of reducible and non-reducible dimers formed upon storage of lyophilized Apo2L/TRAIL crystals containing 2.5% and 12% water.
Figure 17B:
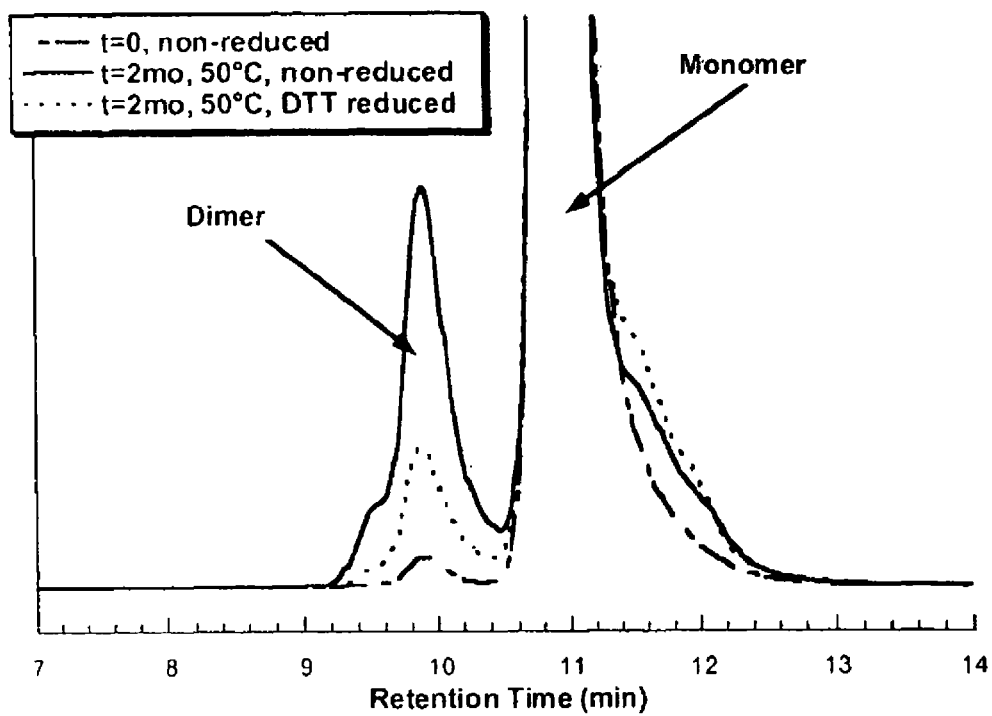

Several of the samples were also assayed using SDS-SEC, on both reduced and non-reduced samples, as previously described to determine the amount of covalent dimer in the samples. The SDS-SEC chromatograms for the samples containing either 2.5% or 12% water and stored for 2 months at 50° C. are illustrated in FIGS. 17A-B, respectively. As shown in FIG. 17A, Apo2L/TRAIL crystals containing 2.5% moisture contain a relatively large amount of covalently linked dimer after storage at 50° C. for 2 months when assayed by SDS-SEC on both reduced and non-reduced samples. This finding suggests the formation of a non-thiol covalent bond as the primary degradation at low moisture contents. While the sample containing 12.5% water also contains a relatively large amount of dimer by non-reduced SDS-SEC after storage under the same conditions, the dimers formed in the higher moisture-containing samples proved to be primarily reducible or thiol-mediated (FIG. 17B). These results suggest a difference in degradation mechanism may occur in those samples having 2.5% or 12.5% residual moisture.

Figure 18A:
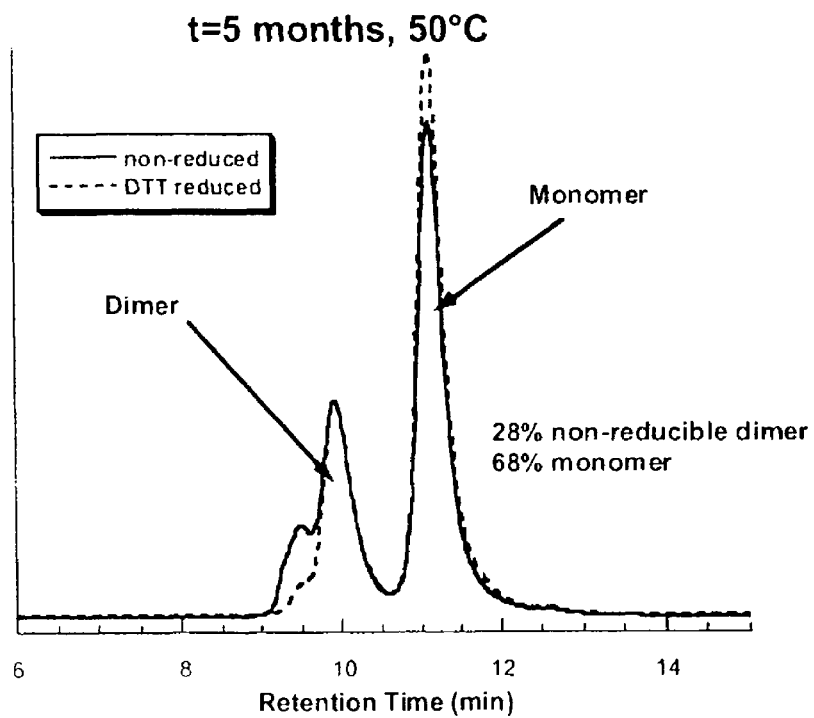
FIGS. 18A-18B show the relative amounts of covalent dimer species, both reducible and non-reducible, contained in the apparent larger molecular weight species formed upon storage of lyophilized Apo2L/TRAIL crystals containing 2.5% and 12% water.
Figure 18B:
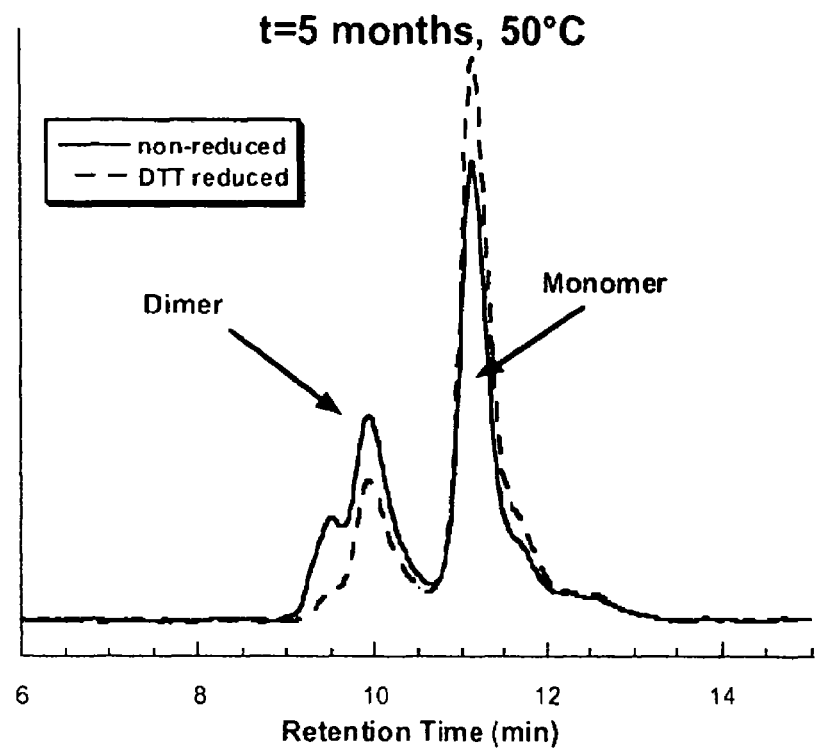

The presence of higher molecular weight aggregrates in the samples was measured using a SEC assay, as described above. The higher molecular weight species from the samples containing either 2.5% or 12% water and stored for 2 months at 50° C. were fraction collected and assayed by reduced and non-reduced SDS-SEC to determine if the covalently linked dimers seen by the denatured SEC methods are a result of inter-trimer covalent bonding. As shown in FIG. 18A, the collected hexamer from the sample stored with 2.5% residual moisture contained an approximate ratio of 2 monomers per non-reducible dimer with no significant amounts of reducible dimer. Conversely, as shown in FIG. 18B, the larger molecular weight aggregates formed in higher water content crystals contained a mixture of both reducible and non-reducible dimer. Taken together, these data indicate that the non-reducible covalent dimer seen by SDS-SEC methods primarily in lower moisture content samples is a result of inter-molecular covalent bonding to form the hexameric structure seen by SEC. The reducible dimer seen by reduced SDS-SEC in the higher moisture samples is thought to be a result of intra-molecular disulfide bonding between two of the three cysteine residues contained within the trimer.

Figure 19A:
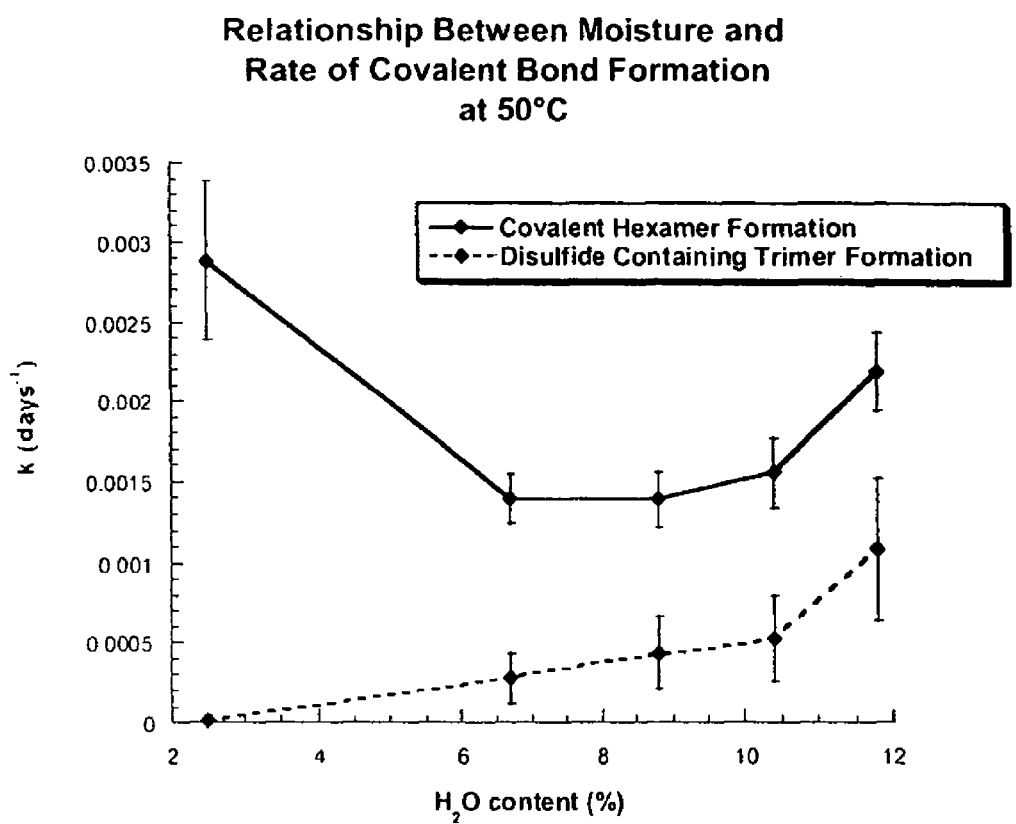
FIGS. 19A-19B show the relationship between the residual moisture content of the crystals and the pseudo-first order rate constants of covalent hexamer and disulfide-linked dimer formation at 50° C. and 40° C.
Figure 19B:
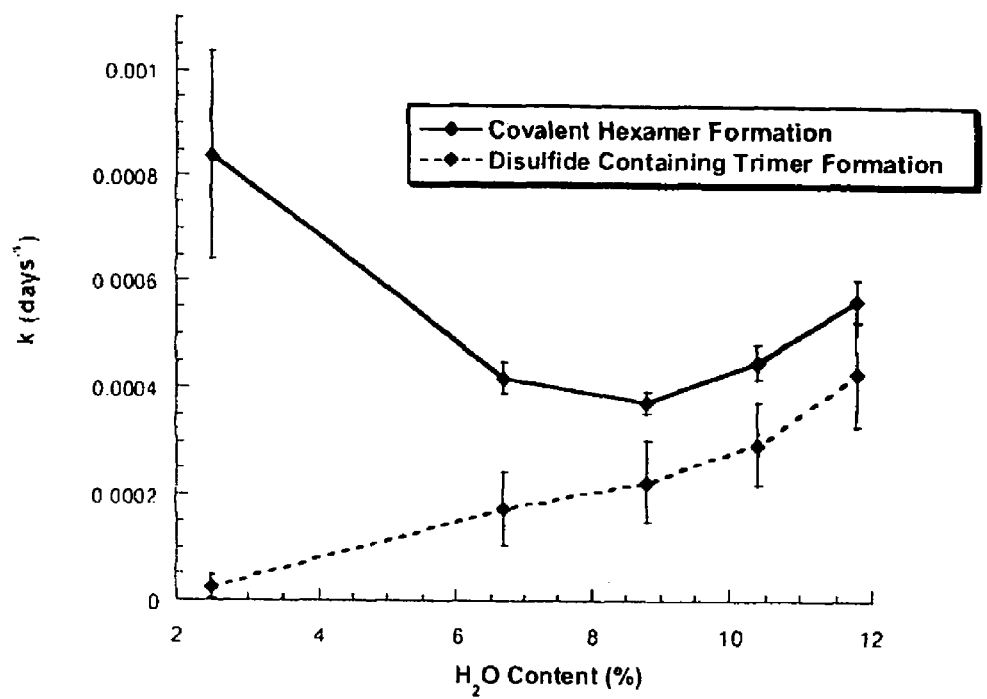

These results suggest that there may be a degradation mechanism present when the Apo2L/TRAIL crystal composition contains either too low of a water or moisture content or alternatively, too high of a water or moisture content. At low moisture content, the protein tended to form a covalently linked hexamer species but not intra-molecular disulfide bonds. As the moisture content was increased, the rate of formation of this species decreased, however, the rate of intra-molecular disulfide bonds increased. It is believed that it may be desirable to achieve a balance between hexamer formation and thiol mediated intra-molecular dimer formation, and that a range of about 5% to about 10% water in the protein crystal composition may optimally achieve such a balance. (See, e.g., FIGS. 19A-B)

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of making a stable formulation of Apo-2 ligand, comprising steps of (a) providing about 1 mg/ml to about 20 mg/ml Apo-2 ligand, about 0.2 M to about 0.5M arginine salt, buffer, and surfactant, (b) combining or mixing the ingredients of step (a) to make a formulation, and (c) adjusting the pH of the formulation of step (b) to about 6 to about 9.

2. The method of claim 1, wherein said arginine salt is arginine succinate.

3. The method of claim 2, wherein the concentration of said arginine succinate is about 0.4M to about 0.5M.

4. The method of claim 1, wherein said buffer is Tris buffer.

5. The method of claim 1, wherein said surfactant is a polysorbate.

6. The method of claim 1, wherein said Apo-2 ligand comprises amino acids 114 to 281 of SEQ. ID. NO: 1.

7. The method of claim 1, wherein the arginine salt is selected from the group consisting of arginine succinate, arginine sulphate, arginine malate, arginine citrate, arginine tartrate, and arginine phosphate.

8. The method of claim 1, wherein said formulation is lyophilized.

9. The method of claim 1, wherein the pH of said formulation is about 6.5 to about 8.5.

10. The method of claim 9, wherein the pH of said formulation is about 7 to about 7.5.

11. The method of claim 1, wherein said Apo-2 ligand is not linked or fused to an epitope tag.

12. The method of claim 1, wherein step (a) further comprises providing a preservative.

13. The method of claim 1, wherein said formulation is storage-stable for at least 12 months.

14. The method of claim 13, wherein said formulation is storage-stable for at least 24 months.

* * * * *